United States Patent
Yen et al.

(10) Patent No.: US 10,428,269 B2
(45) Date of Patent: Oct. 1, 2019

(54) INDENOTRIPHENYLENE DERIVATIVE AND ORGANIC ELECTROLUMINESCENCE DEVICE USING THE SAME

(71) Applicants: Feng-Wen Yen, Taipei (TW); Shu-Hua Yeh, Hsinchu (TW)

(72) Inventors: Feng-Wen Yen, Taipei (TW); Shu-Hua Yeh, Hsinchu (TW)

(*) Notice: Subject to any disclaimer, the term of this patent is extended or adjusted under 35 U.S.C. 154(b) by 173 days.

(21) Appl. No.: 15/854,770

(22) Filed: Dec. 27, 2017

(65) Prior Publication Data
US 2019/0194534 A1   Jun. 27, 2019

(51) Int. Cl.
| H01L 51/50 | (2006.01) |
| C09K 11/06 | (2006.01) |
| C07C 13/62 | (2006.01) |
| C07D 209/82 | (2006.01) |
| C07D 307/91 | (2006.01) |
| C07D 333/76 | (2006.01) |
| H01L 51/00 | (2006.01) |

(52) U.S. Cl.
CPC ............ *C09K 11/06* (2013.01); *C07C 13/62* (2013.01); *C07D 209/82* (2013.01); *C07D 307/91* (2013.01); *C07D 333/76* (2013.01); *H01L 51/0054* (2013.01); *H01L 51/0058* (2013.01); *H01L 51/0085* (2013.01); *H01L 51/5012* (2013.01); *C07C 2603/18* (2017.05); *C07C 2603/54* (2017.05); *C09K 2211/1011* (2013.01); *C09K 2211/1029* (2013.01); *C09K 2211/1088* (2013.01)

(58) Field of Classification Search
None
See application file for complete search history.

(56) References Cited

U.S. PATENT DOCUMENTS

| 9,260,363 | B2 | 2/2016 | Yen et al. |
| 9,537,103 | B1 | 1/2017 | Yen |
| 9,812,649 | B2 | 11/2017 | Yen et al. |

FOREIGN PATENT DOCUMENTS

KR    102010113688 A  * 5/2010  ............ H01L 51/50

* cited by examiner

*Primary Examiner* — Gregory D Clark

(57) ABSTRACT

The present invention discloses an indenotriphenylene phosphine oxide derivative and an organic electroluminescence device employing the derivative as the phosphorescent host material in the light emitting layer, and/or the hole blocking material and/or the electron transporting material in the organic EL device, which thereby exhibits improved performance.

12 Claims, 1 Drawing Sheet

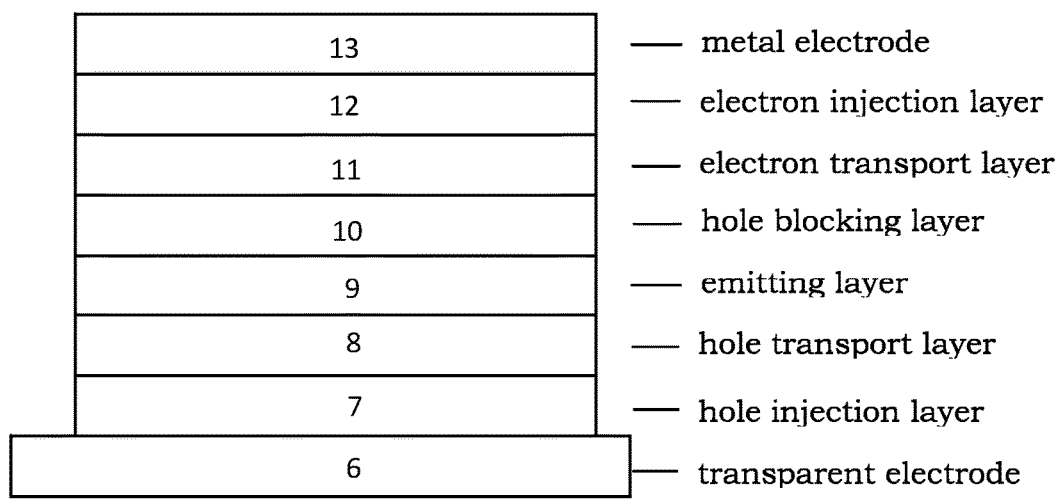

INDENOTRIPHENYLENE DERIVATIVE AND ORGANIC ELECTROLUMINESCENCE DEVICE USING THE SAME

FIELD OF INVENTION

The present invention generally relates to an indenotriphenylene derivative and, more specifically, to an indenotriphenylene phosphine oxide derivative and an organic electroluminescence device using the indenotriphenylene phosphine oxide derivative.

BACKGROUND OF THE INVENTION

An organic electroluminescence (hereinafter referred to as organic EL) device is an organic light-emitting diode (OLED) in which the light emitting layer is a film made from organic compounds, which emits light in response to the electric current. The organic EL device is applied to flat panel displays due to its high illumination, low weight, ultra-thin profile, self-illumination without back light, low power consumption, wide viewing angle, high contrast, simple fabrication methods and rapid response time.

The first diode device was reported by Ching W. Tang and Steven Van Slyke at Eastman Kodak in 1987. The device used a two-layer structure with separate hole transporting and electron transporting layers such that recombination and light emission occurred in the middle of the organic layer. This resulted in reduction of operating voltage and improvement of the efficiency, thereby leading to the current area of organic EL device research and device production.

Typically, the organic EL device is composed of organic material layers sandwiched between two electrodes. The organic material layers include the hole transporting layer, the light emitting layer, and the electron transporting layer. The basic mechanism of organic EL involves the injection, transport, and recombination of carriers as well as exciton formation for emitting light. When an external voltage is applied across the organic EL device, electrons and holes are injected from the cathode and the anode, respectively. Electrons will be injected from the cathode into a LUMO (lowest unoccupied molecular orbital) and holes will be injected from the anode into a HOMO (highest occupied molecular orbital). Subsequently, the electrons recombine with holes in the light emitting layer to form excitons, which then deactivate to emit light. When luminescent molecules absorb energy to achieve an excited state, the exciton may either be in a singlet state or a triplet state, depending on how the spins of the electrons and holes have been combined. It is well known that the excitons formed under electrical excitation typically include 25% singlet excitons and 75% triplet excitons. In the fluorescence materials, however, the electrically generated energy in the 75% triplet excitons will be dissipated as heat for decay from the triplet state is spin forbidden. Therefore, a fluorescent electroluminescence device has only 25% internal quantum efficiency, which leads to the theoretically highest external quantum efficiency (EQE) of only 5% due to only ~20% of the light outcoupling efficiency of the device. In contrast to fluorescent electroluminescence devices, phosphorescent organic EL devices make use of spin-orbit interactions to facilitate intersystem crossing between singlet and triplet states, thus obtaining emission from both singlet and triplet states and the internal quantum efficiency of electroluminescence devices from 25% to 100%.

The phosphorescent organic EL device utilizes both triplet and singlet excitions. Cause of longer lifetime and diffusion length of triplet excitions compared to those of singlet excitions, the phosphorescent organic EL device generally needs an additional hole blocking layer (HBL) between the emitting layer (EML) and the electron transporting layer (ETL) or the electron transporting layer with hole blocking ability (HBETL) instead of the typical ETL. The purpose of the use of HBL or HBETL is to confine the recombination of injected holes and electrons and the relaxation of created excitons within the EML, hence the device's efficiency can be improved. To meet such roles, the hole blocking materials must have HOMO (highest occupied molecular orbital) and LUMO (lowest unoccupied molecular orbital) energy levels suitable to block holes transport from the EML to the ETL and to pass electrons from the ETL to the EML. In addition, good thermal stability of the phosphorescent emitting host material is also needed.

In the present invention, we develop an indenotriphenylene derivative to improve the performance of the organic EL devices.

SUMMARY OF THE INVENTION

Accordingly, an object of the invention is to provide an indenotriphenylene derivative and an organic EL device using the same, which can operate under reduced voltage, increase current efficiency, and extend half-life time.

Another object of the present invention is to provide an indenotriphenylene phosphine oxide derivative, which can be used as a phosphorescent host material in the light emitting layer, and/or an electron transporting material or a hole blocking material in an organic EL device to improve the power consumption, current efficiency, and lifetime.

The present invention has the economic advantages for industrial practice. According to the present invention, an indenotriphenylene derivative which can be used in organic EL device is disclosed. The indenotriphenylene derivative is represented by the following formula (A):

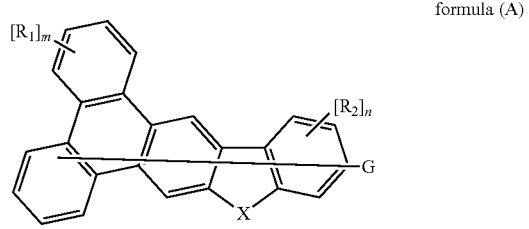

formula (A)

wherein m is 0 to 10; n is 0 to 4; X is O, S, $C(R_3)(R_4)$, $N(R_5)$, or $Si(R_6)(R_7)$; $R_1$ to $R_7$ are each independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms; and G represents formula (B) below:

formula (B)

wherein L represents a single bond, a substituted or unsubstituted arylene group having 6 to 30 ring carbon atoms, or a substituted or unsubstituted heteroarylene group having 3 to 30 ring carbon atoms; P is a phosphorus atom; Q is an oxygen atom, a sulfur atom, or a selenium atom; $Ar_1$ and $Ar_2$ are each independently a substituted or unsubstituted aryl group having 6 to 60 ring carbon atoms, or a substituted or unsubstituted heteroaryl group having 3 to 60 ring carbon atoms; and $Ar_1$ and $Ar_2$ are optionally connected to each other to form an aromatic or heteroaromatic ring.

The present invention further discloses an organic electroluminescence device. The organic electroluminescence device comprises a pair of electrodes composed of a cathode and an anode, and a light emitting layer and one or more organic thin film layers between the pair of electrodes. At least one of the light emitting layer and the organic thin film layer comprises the indenotriphenylene derivative of formula (A).

BRIEF DESCRIPTION OF THE DRAWINGS

The FIGURE shows one embodiment of the organic EL device of the present invention. In the device, hole injection layer 7 is deposited onto transparent electrode 6, hole transport layer 8 is deposited onto hole injection layer 7, phosphorescence emitting layer 9 is deposited onto hole transport layer 8, hole blocking layer 10 is deposited onto emitting layer 9, electron transport layer 11 is deposited onto hole blocking layer 10, electron injection layer 12 is deposited onto electron transport layer 11, and metal electrode 13 is deposited onto electron injection layer 12.

DESCRIPTION OF THE PREFERRED EMBODIMENTS

What probed into the invention is the indenotriphenylene derivative and organic EL device using the indenotriphenylene derivative. Detailed descriptions of the production, structure and elements will be provided as follows such that the invention can be fully understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In one embodiment of the present invention, an indenotriphenylene derivative which can be used as the phosphorescent host material of the light emitting layer, and/or the electron transporting material or hole blocking material in the organic EL device is disclosed. The indenotriphenylene derivative is represented by the following formula (A):

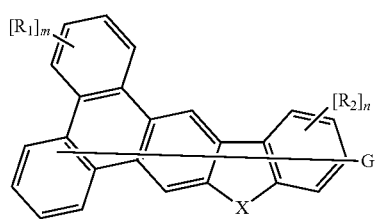

formula (A)

wherein m is 0 to 10; n is 0 to 4; X is O, S, $C(R_3)(R_4)$, $N(R_5)$, or $Si(R_6)(R_7)$; $R_1$ to $R_7$ are each independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms; and G represents formula (B) below:

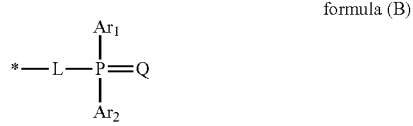

formula (B)

wherein L represents a single bond, a substituted or unsubstituted arylene group having 6 to 30 ring carbon atoms, or a substituted or unsubstituted heteroarylene group having 3 to 30 ring carbon atoms; P is a phosphorus atom; Q is an oxygen atom, a sulfur atom, or a selenium atom; $Ar_1$ and $Ar_2$ are each independently a substituted or unsubstituted aryl group having 6 to 60 ring carbon atoms, or a substituted or unsubstituted heteroaryl group having 3 to 60 ring carbon atoms; and $Ar_1$ and $Ar_2$ are optionally connected to each other to form an aromatic or heteroaromatic ring.

Preferably, the indenotriphenylene derivative is represented by the following formula (C) or formula (D):

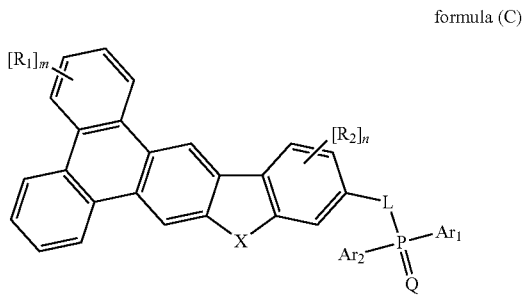

formula (C)

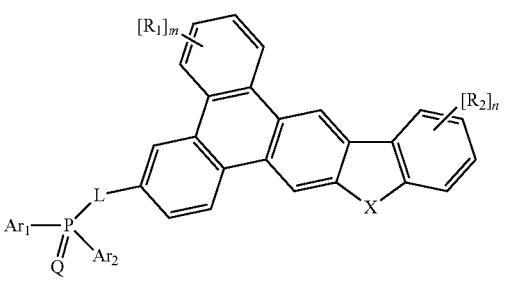

formula (D)

wherein m is 0 to 10; n is 0 to 4; X is O, S, $C(R_3)(R_4)$, $N(R_5)$, or $Si(R_6)(R_7)$; $R_1$ to $R_7$ are each independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms; L represents a single bond, a substituted or unsubstituted arylene group having 6 to 30 ring carbon atoms, or a substituted or unsubstituted heteroarylene group having 3 to 30 ring carbon atoms; P is a phosphorus atom; Q is an oxygen atom, a sulfur atom, or a selenium atom; and $Ar_1$ and $Ar_2$ are each independently a substituted or unsubstituted aryl group having 6 to 60 ring carbon atoms, or a substituted or unsubstituted heteroaryl group having 3 to 60 ring carbon atoms.

In some embodiments, $Ar_1$ or $Ar_2$ represents one of the following substituents:

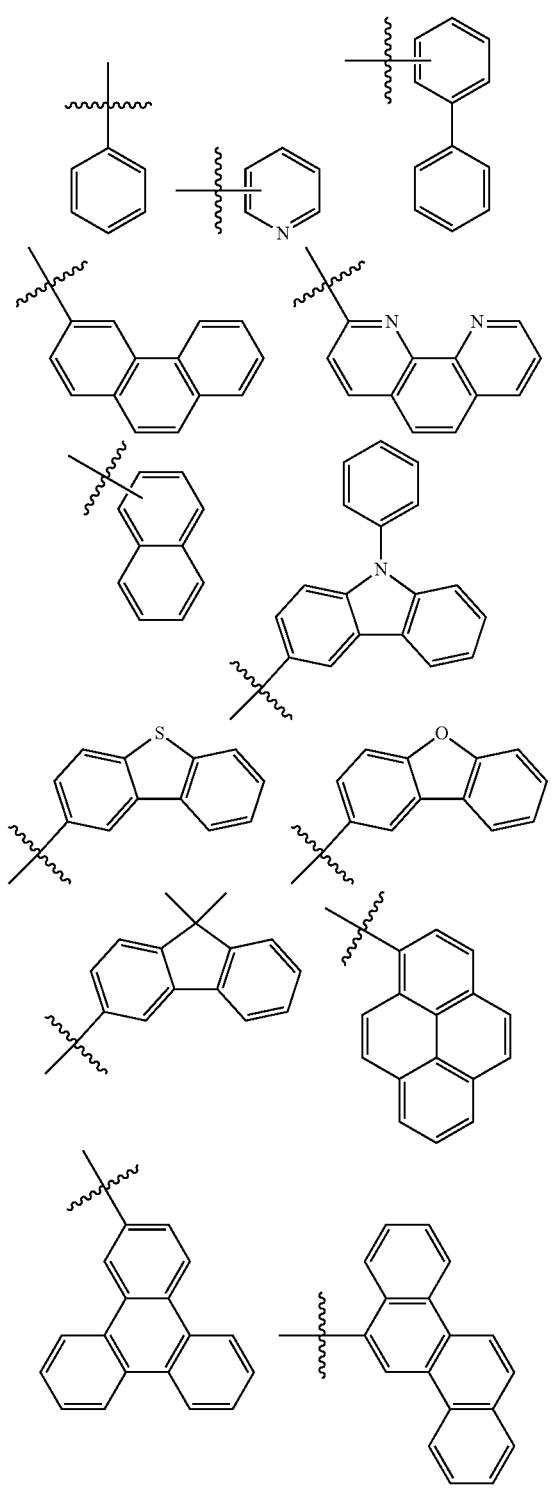

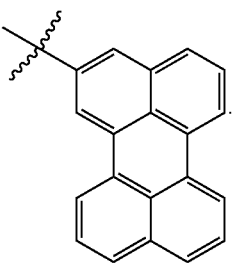 [SMILES: *c1cc2cccc3c4cccc5cccc(c(c1)c23)c54]

Preferably, the indenotriphenylene derivative is one of the following compounds:

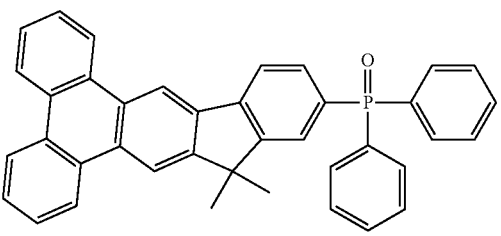

A1

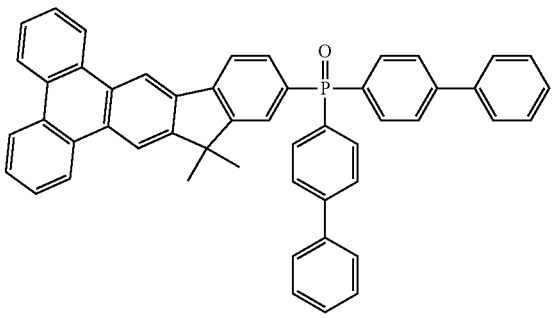

A2

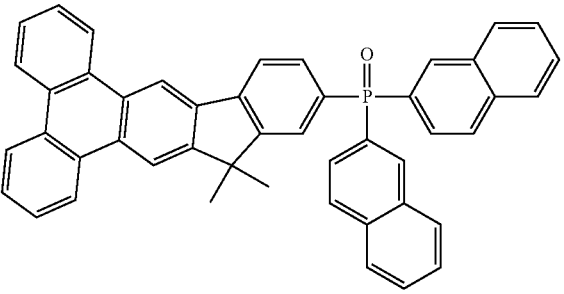

A3

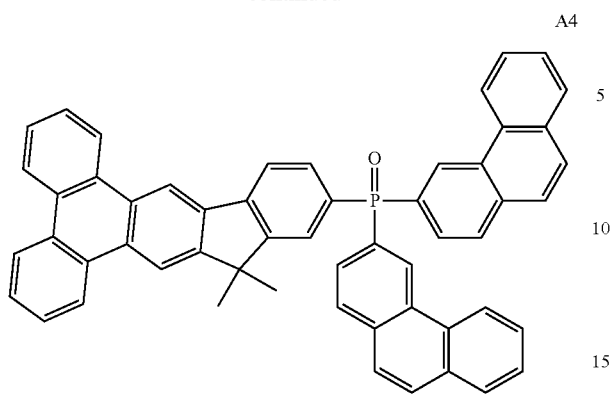
A4
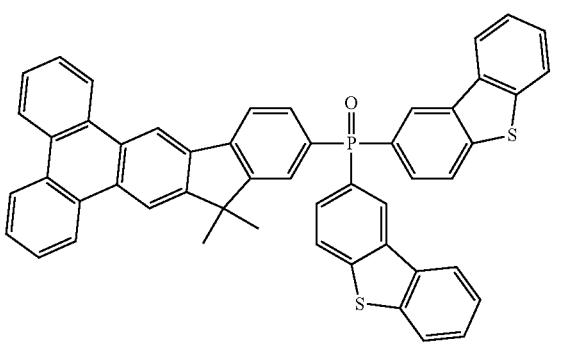
A8
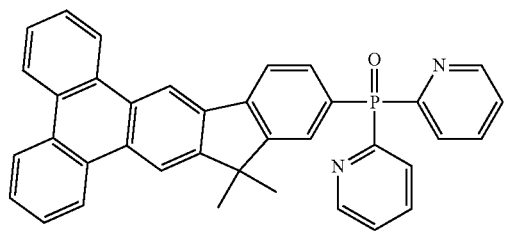
A5
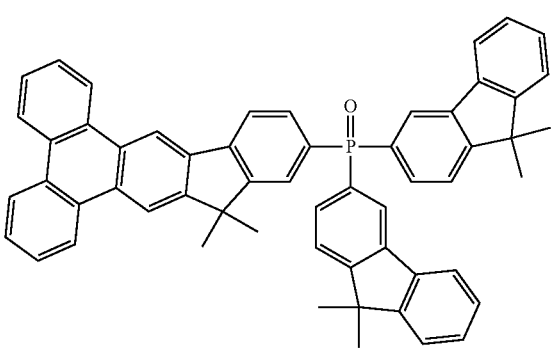
A9
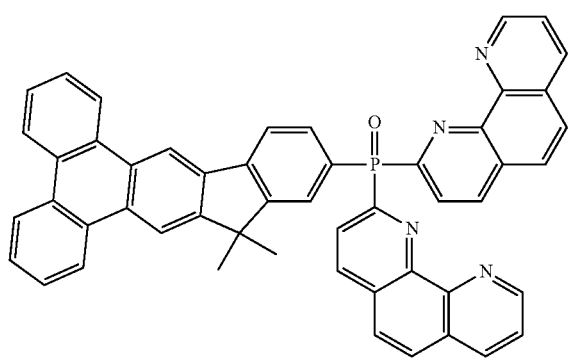
A6
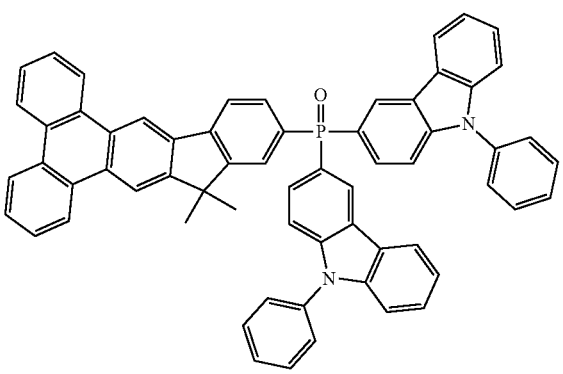
A10
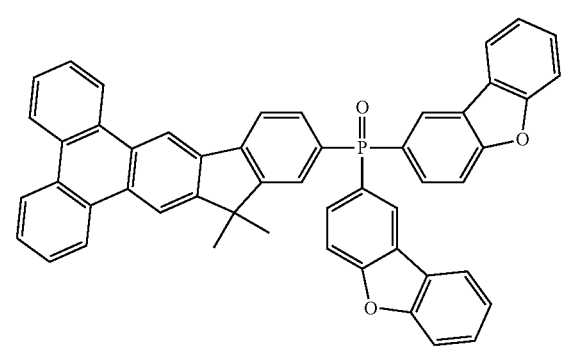
A7
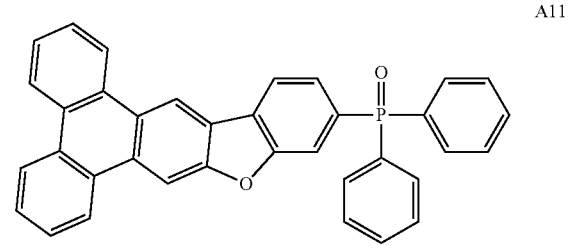
A11

A12
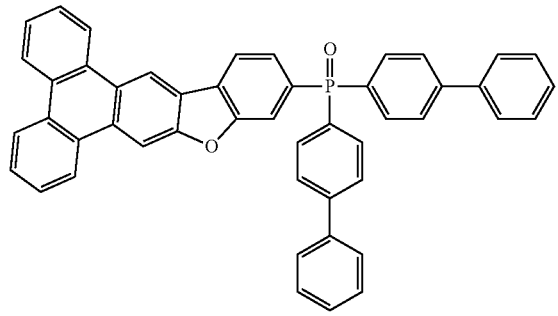
A13
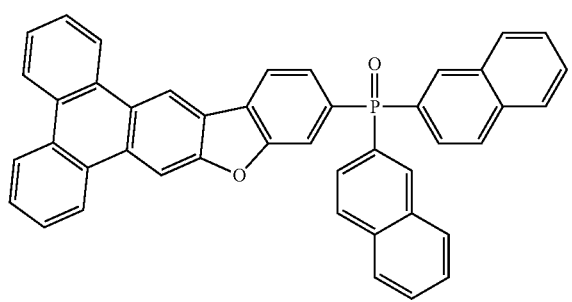
A14
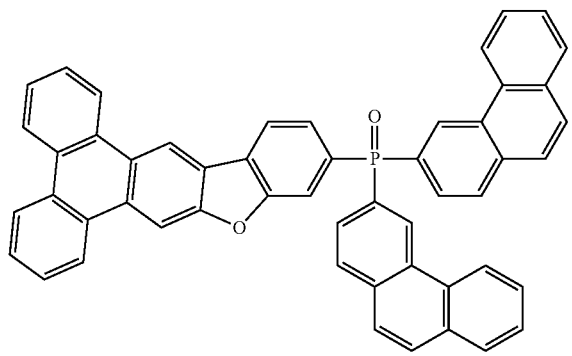
A15
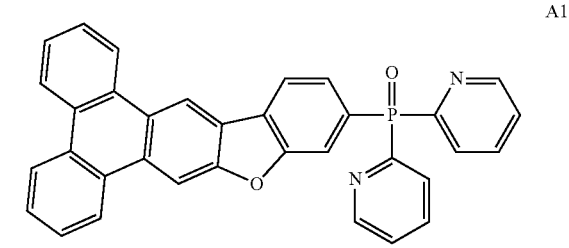
A16
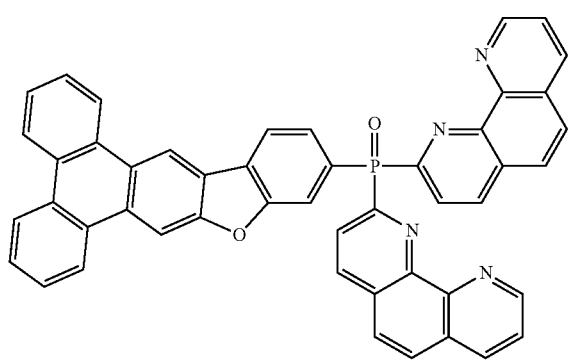
A17
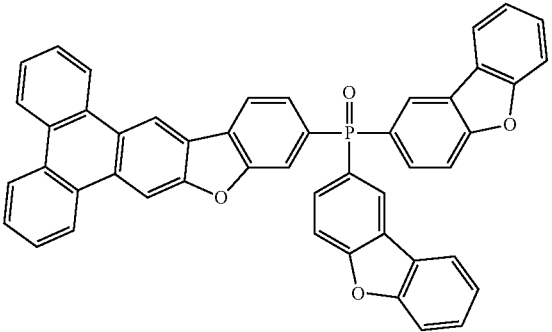
A18
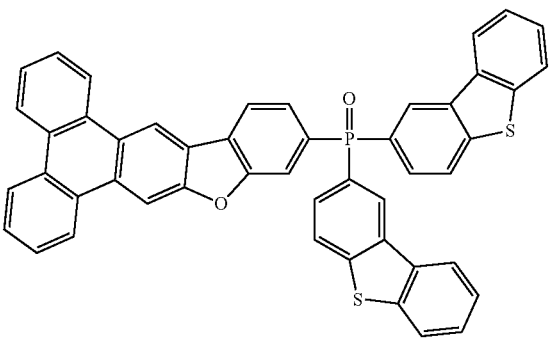
A19
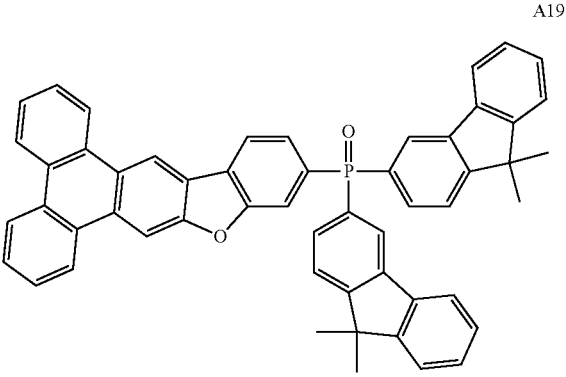
A20
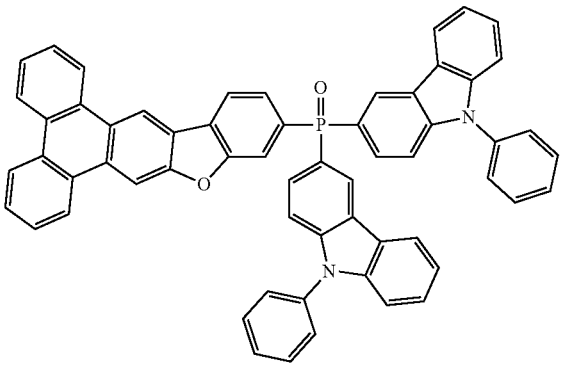

A21
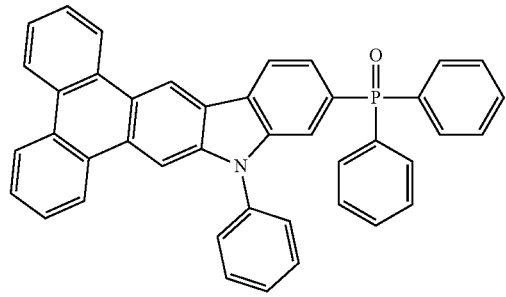
A22
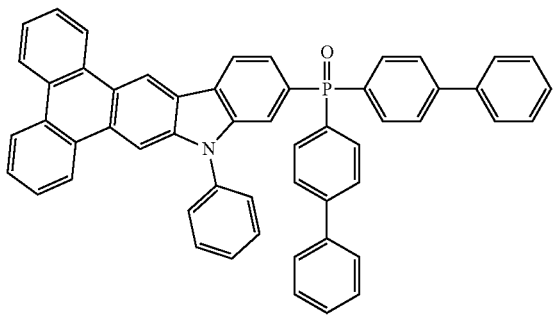
A23
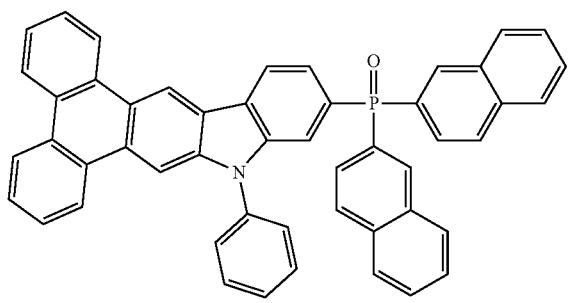
A24
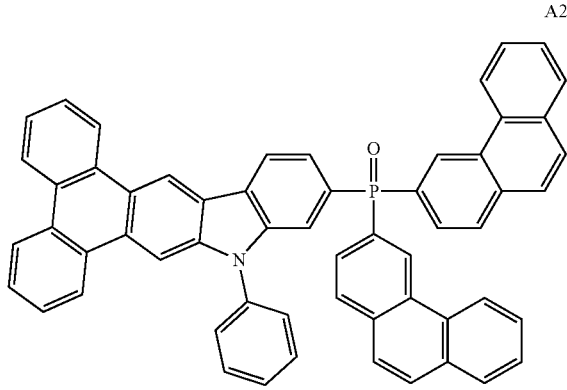
A25
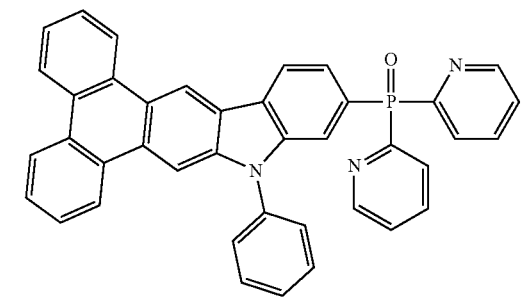
A26
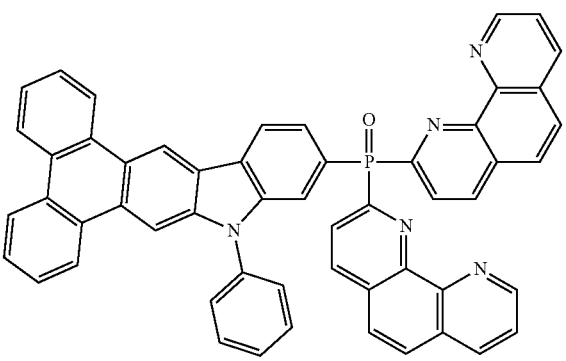
A27
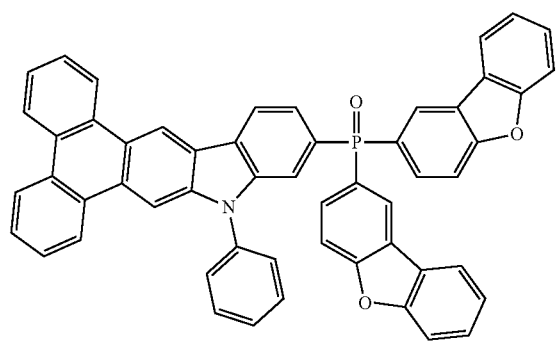
A28
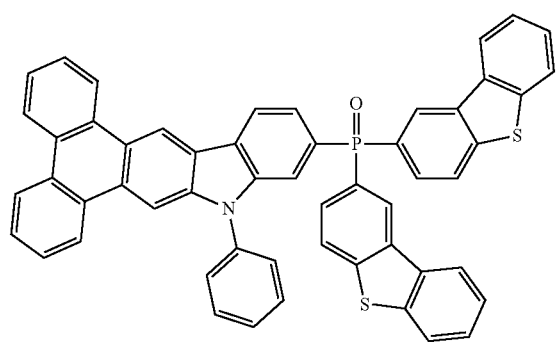
A29
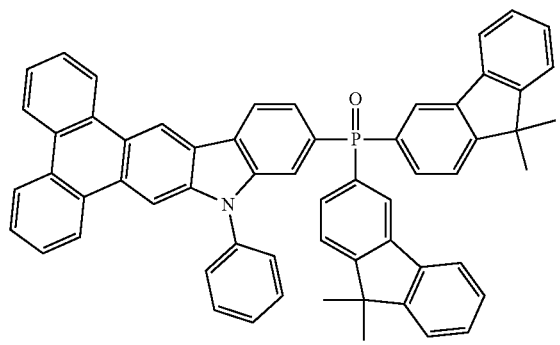

A30

A31

A32

A33

A34

A35

A36

A37

A38
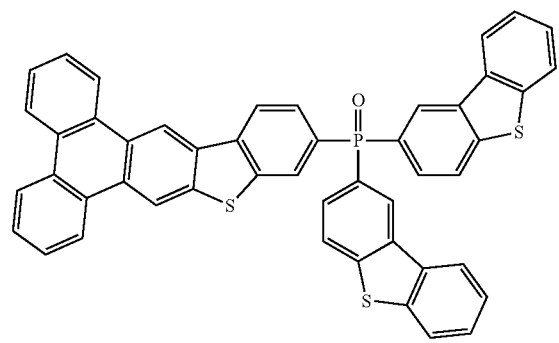
A39
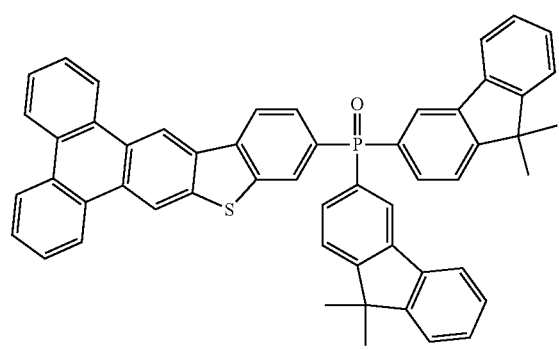
A40
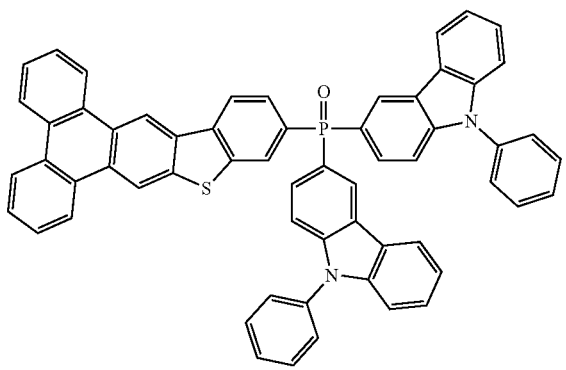
A41
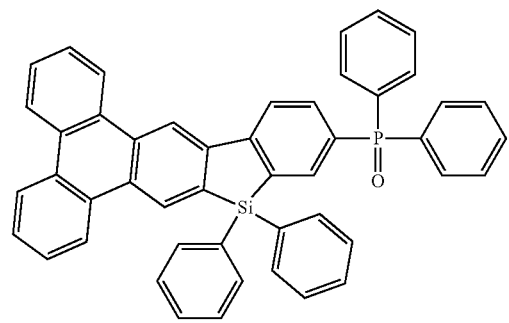
A42
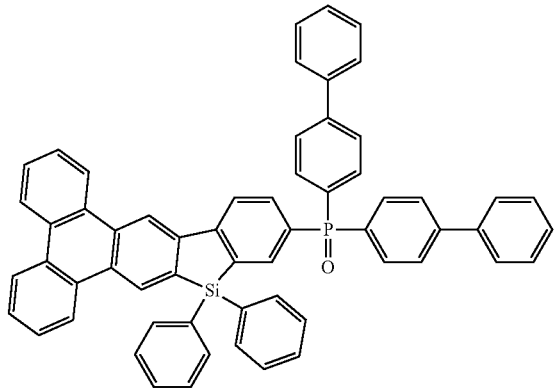
A43
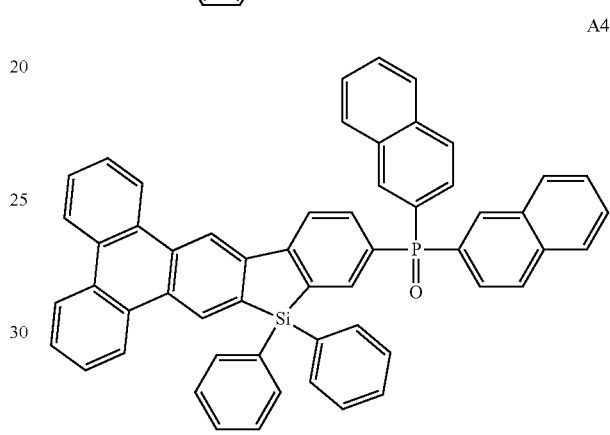
A44
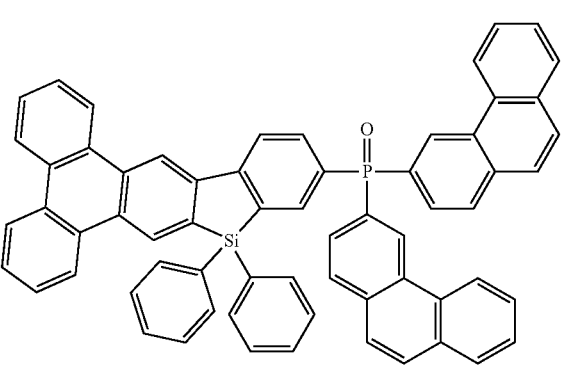
A45
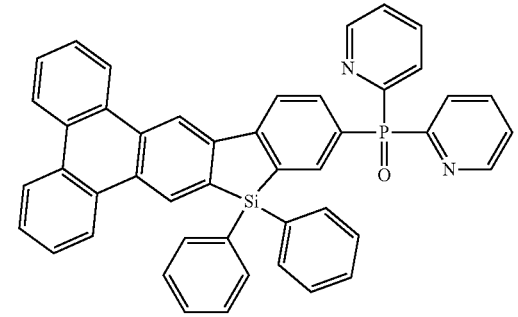

A46
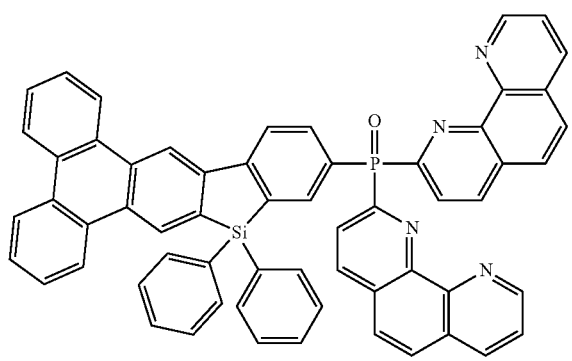
A47
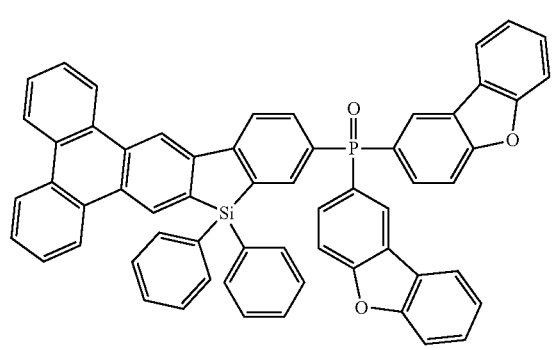
A48
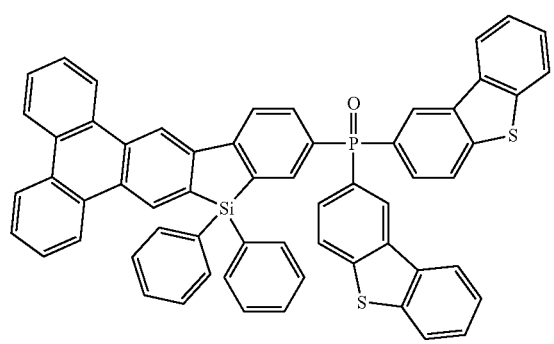
A49
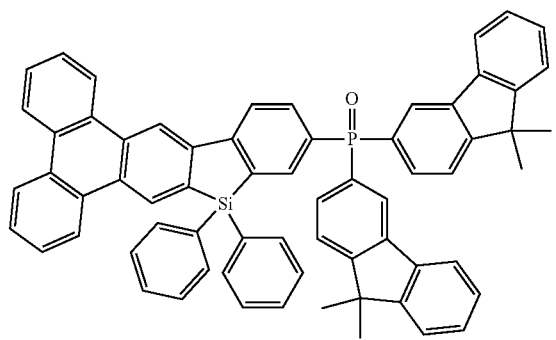
A50
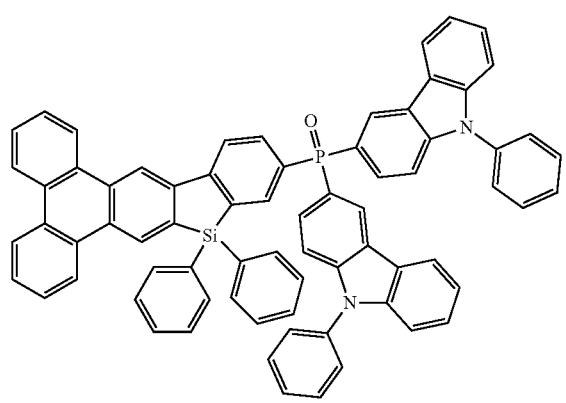
A51
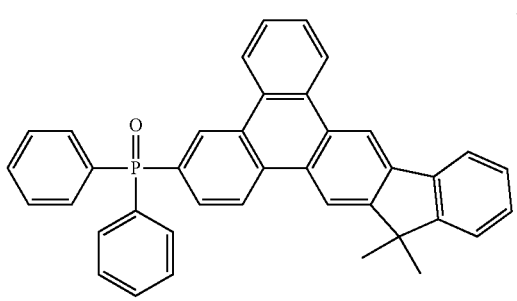
A52
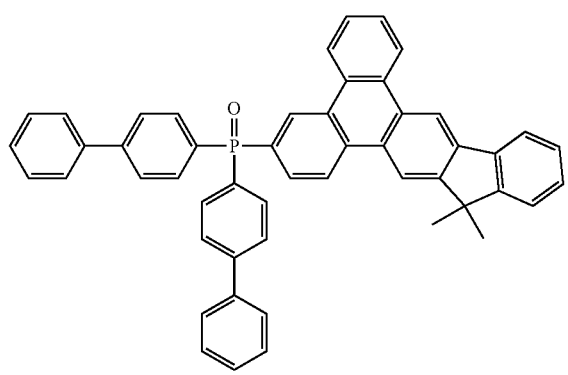
A53
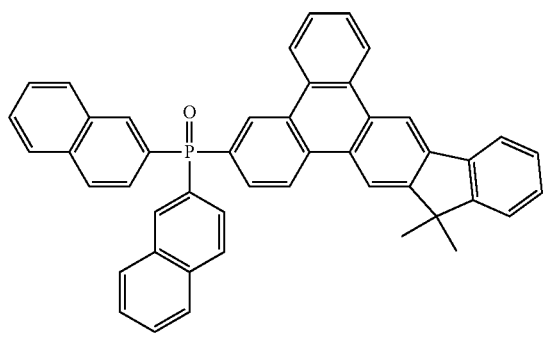

-continued
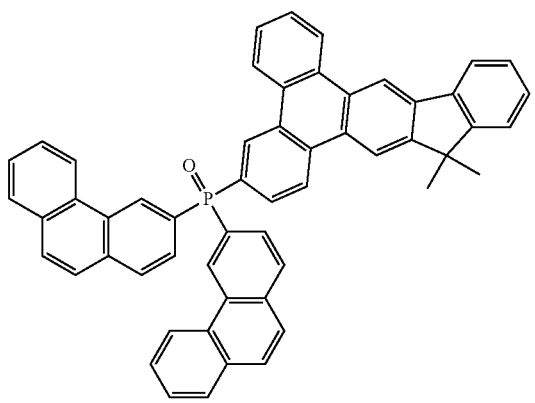
A54
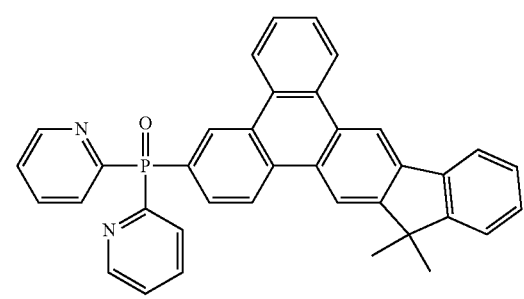
A55
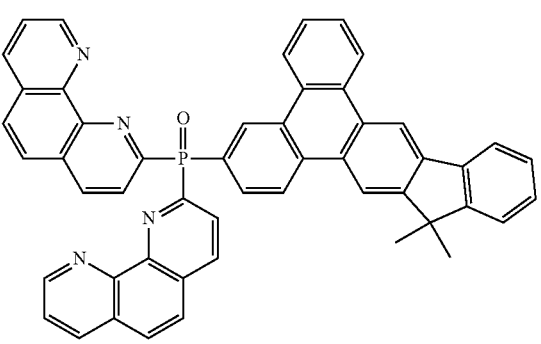
A56
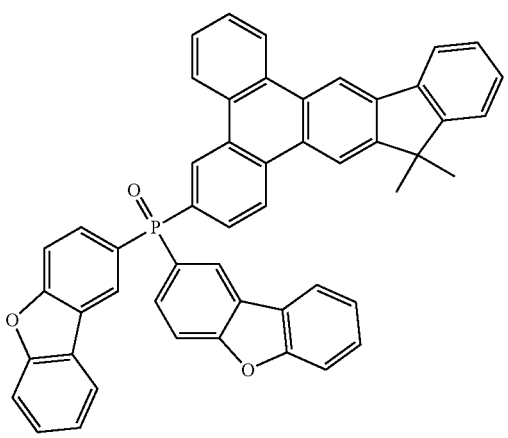
A57
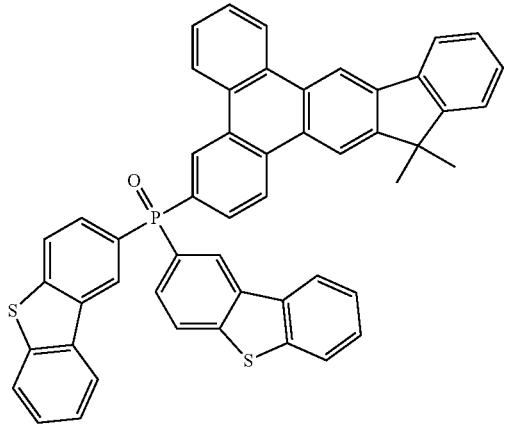
A58
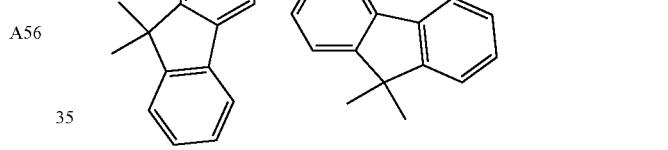
A59
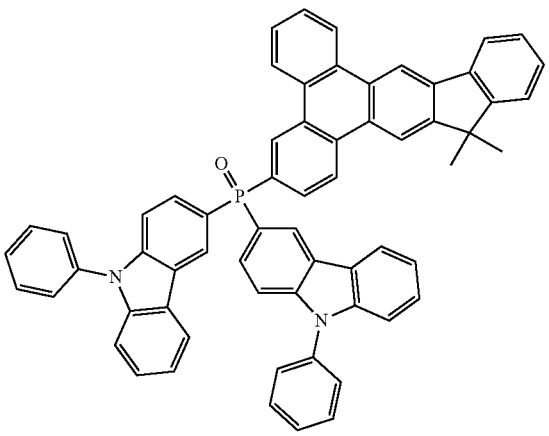
A60
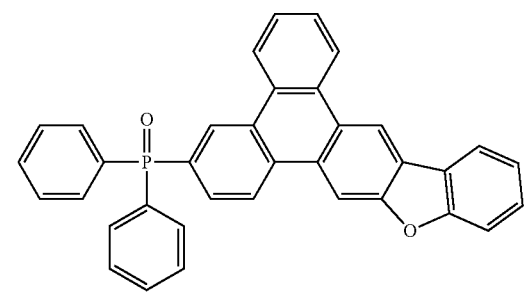
A61

A62
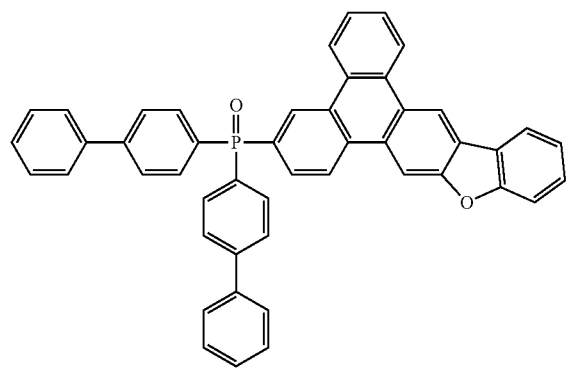
A63
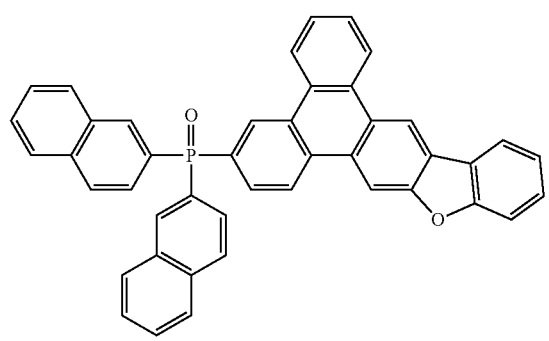
A64
A65
A66
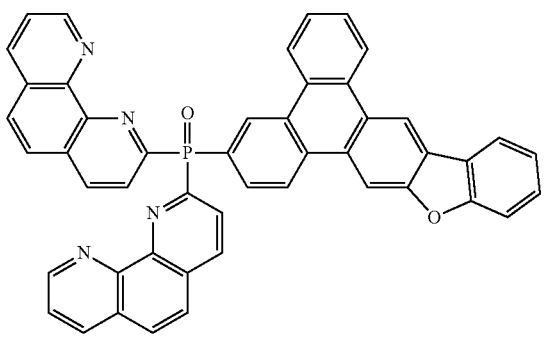
A67
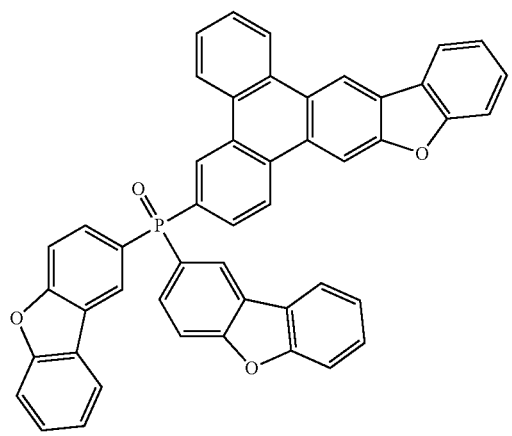
A68
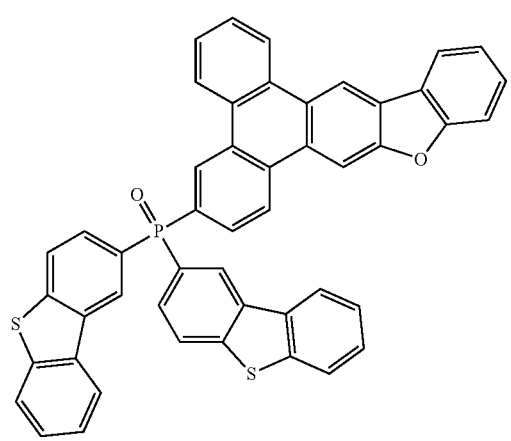

A69
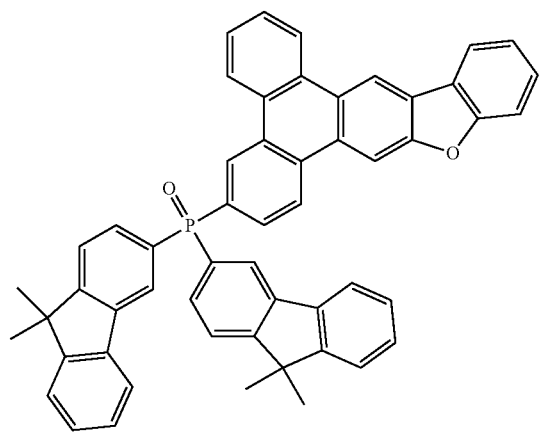
A70
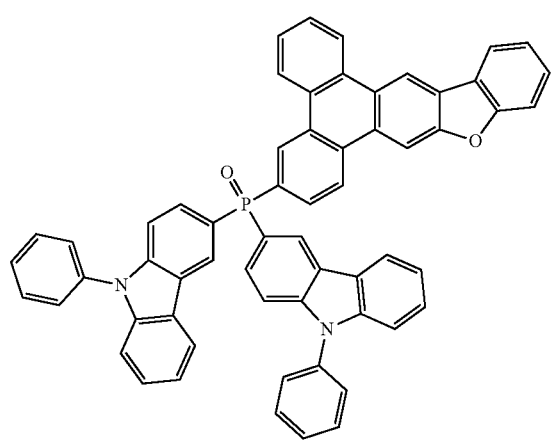
A71
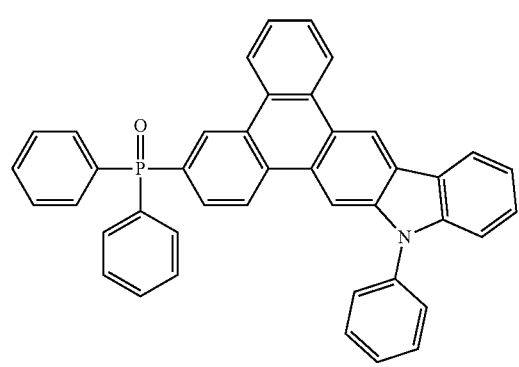
A72
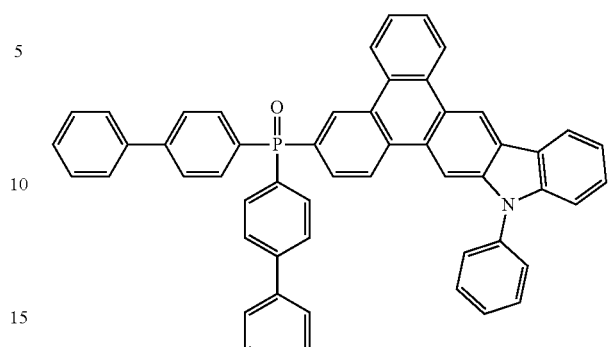
A73
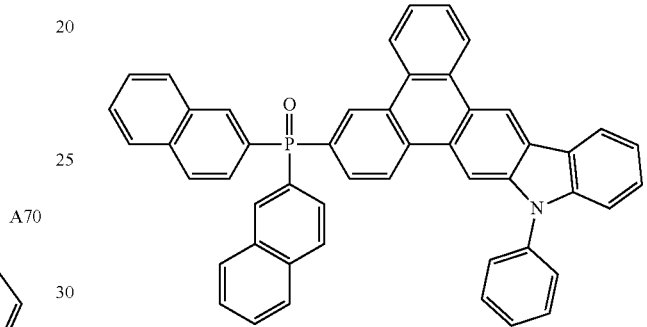
A74
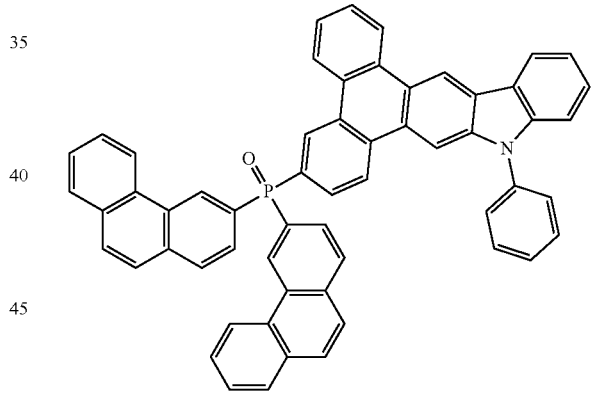
A75
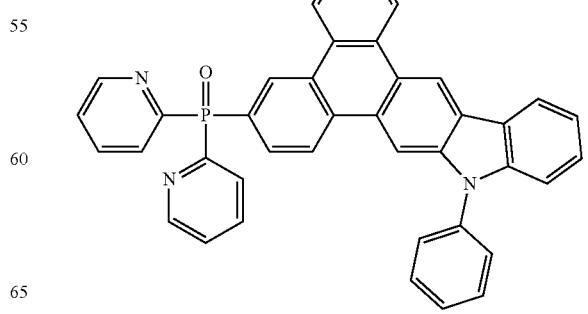

A76
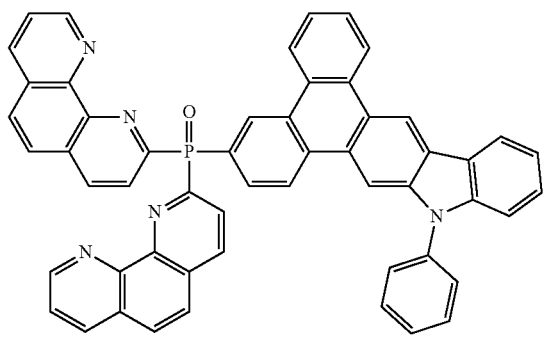
A77
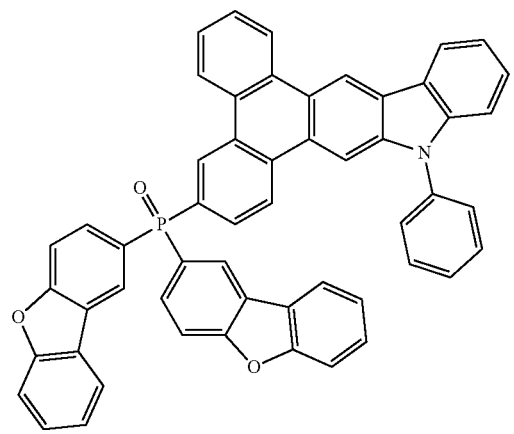
A78
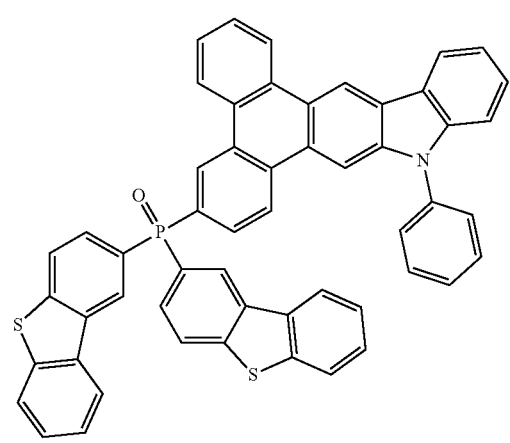
A79
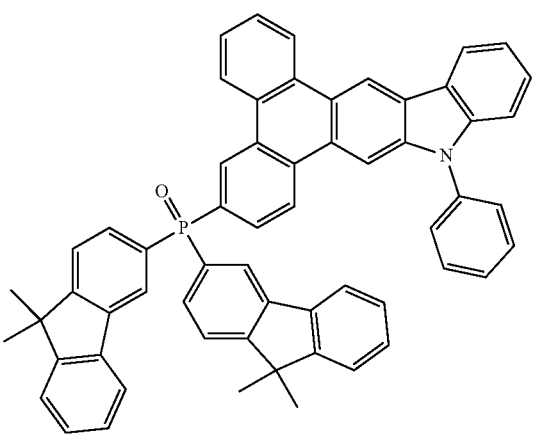
A80
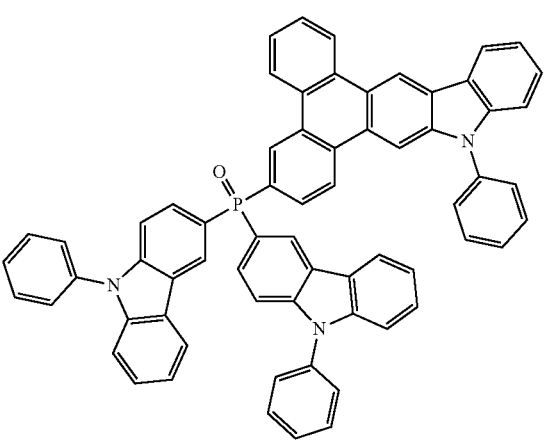
A81
A82
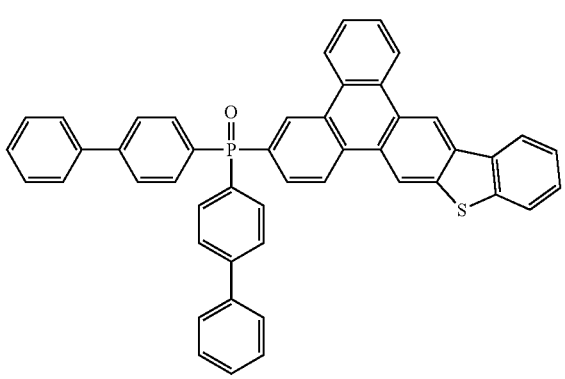

A83
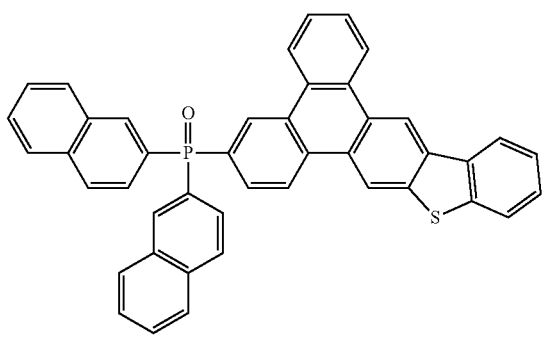
A84
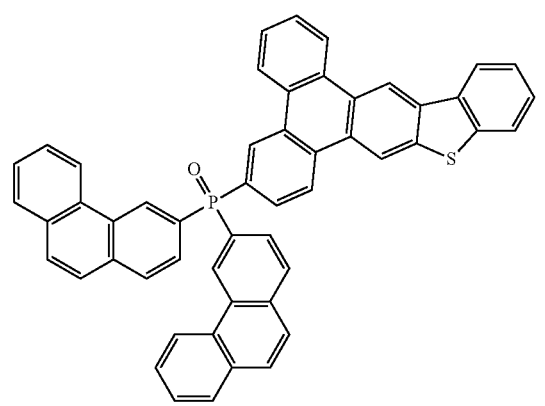
A85
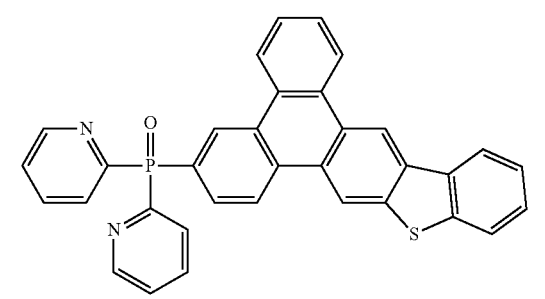
A86
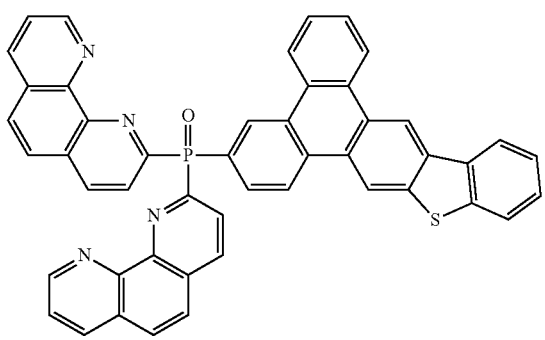
A87
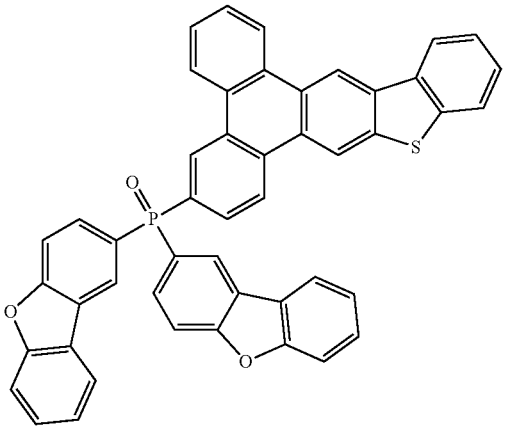
A88
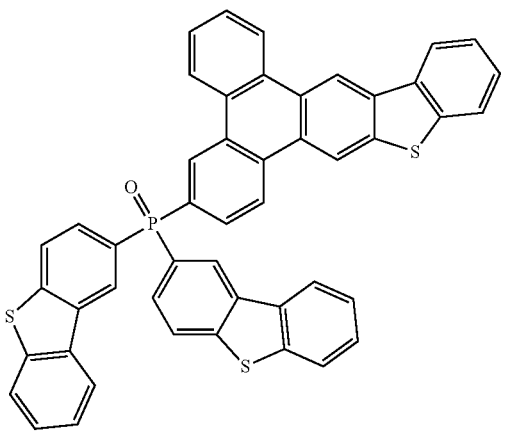
A89
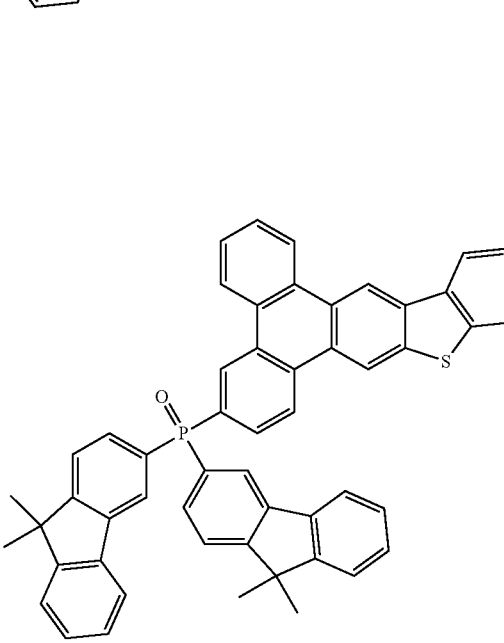

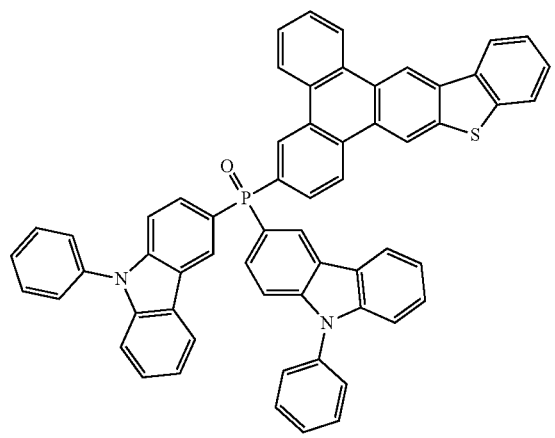
A90
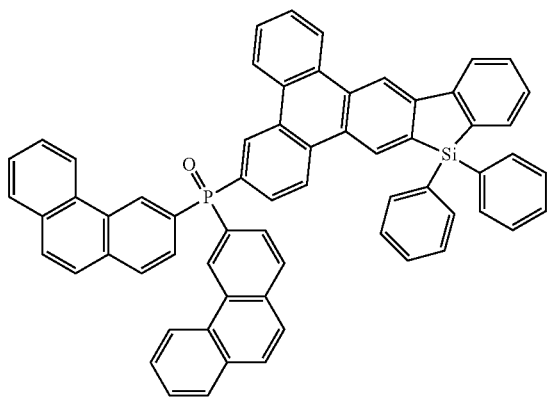
A94
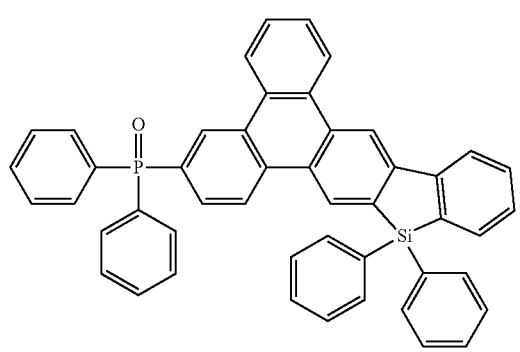
A91
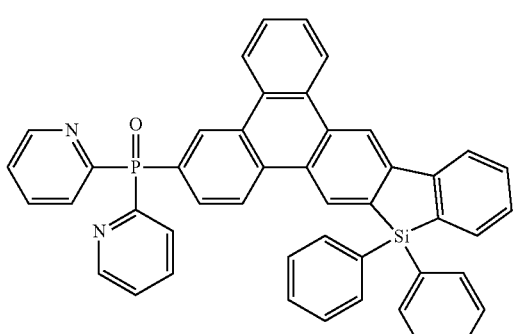
A95
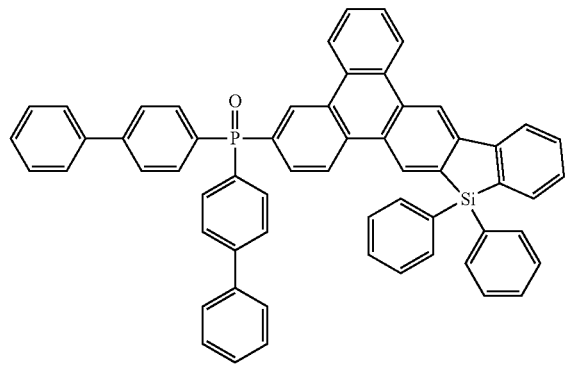
A92
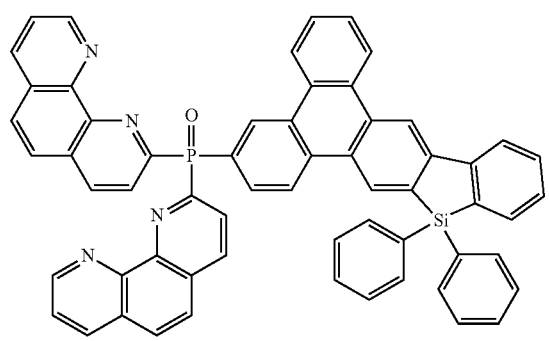
A96
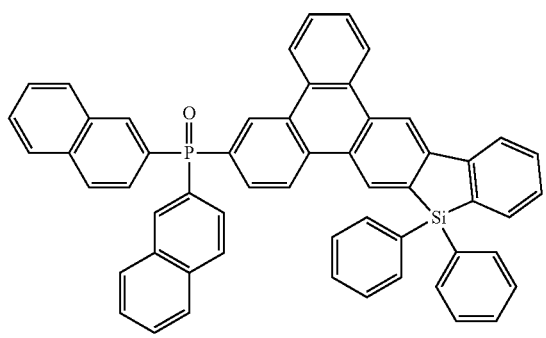
A93
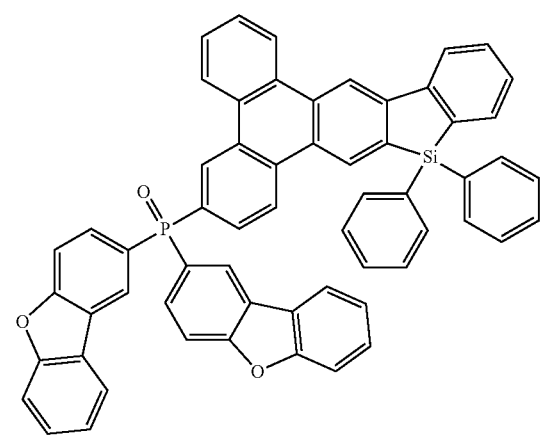
A97

-continued
A98
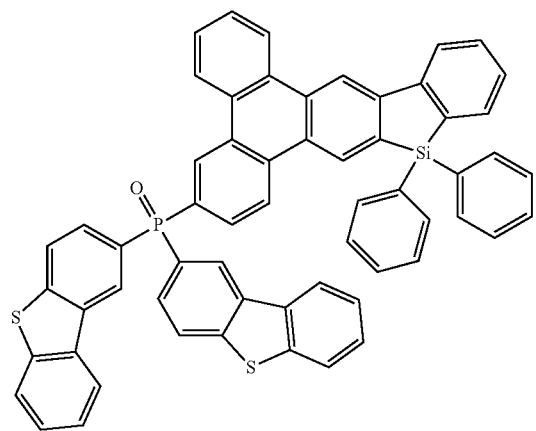
A99
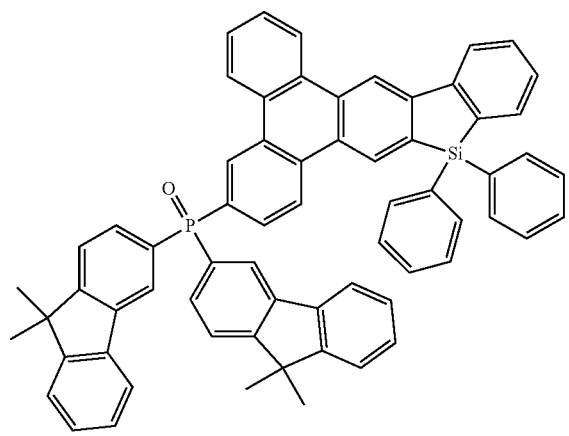
A100
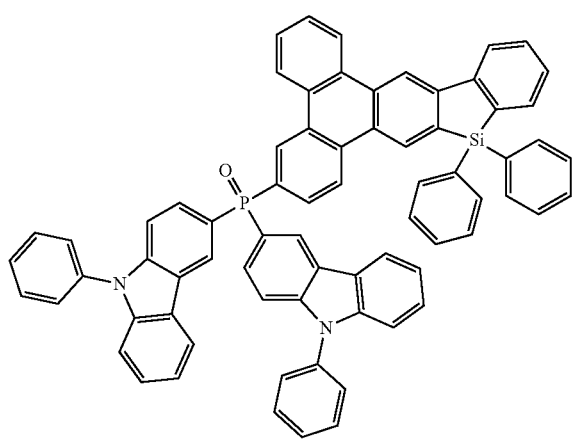
-continued
A101
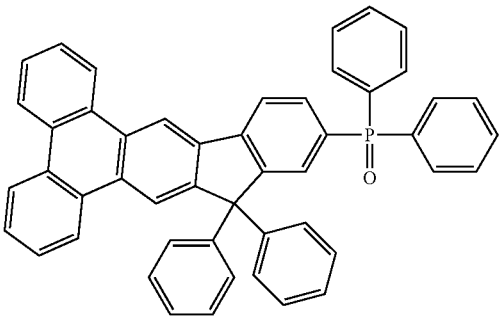
A102
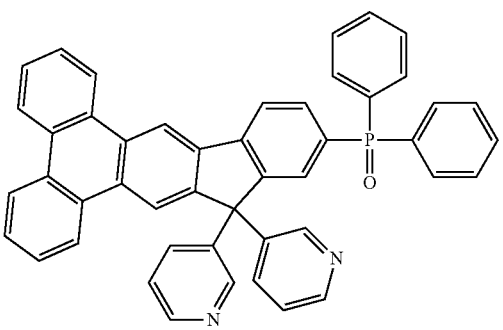
A103
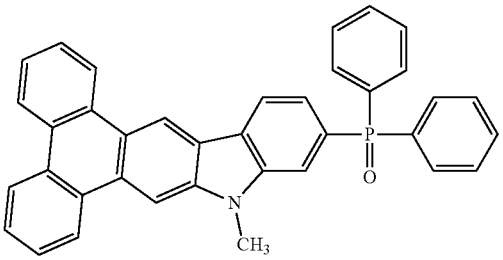
A104
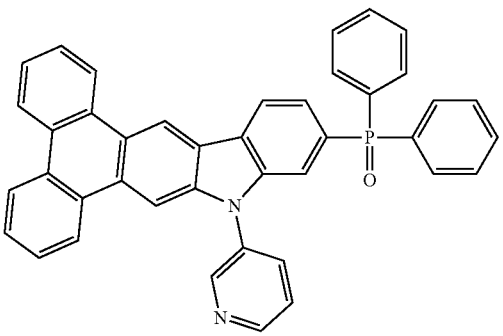
A105
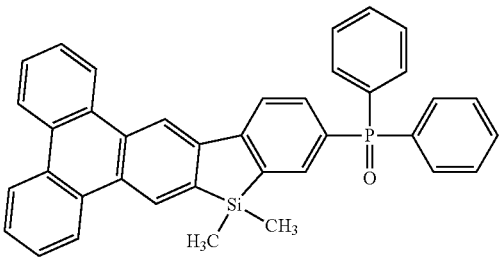

A106
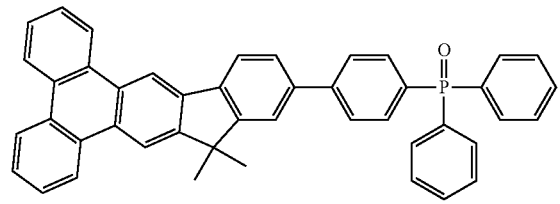
A107
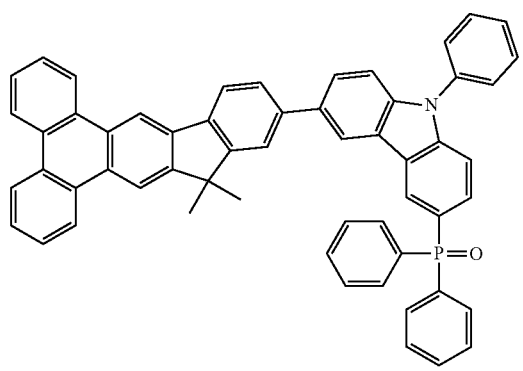
A108
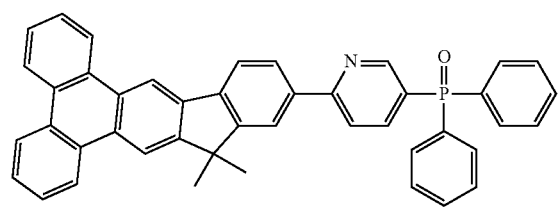
A109
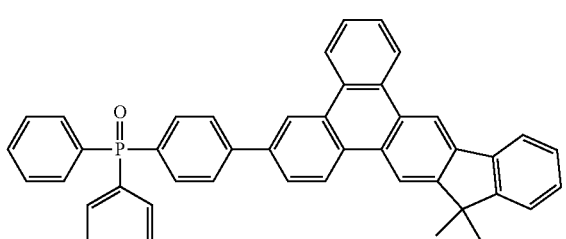
A110
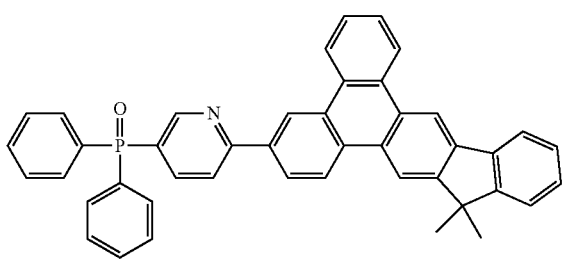
A111
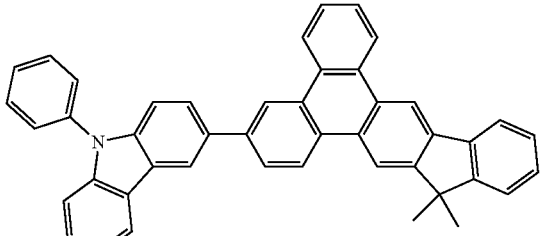
A112
A113
A114
A115

A116
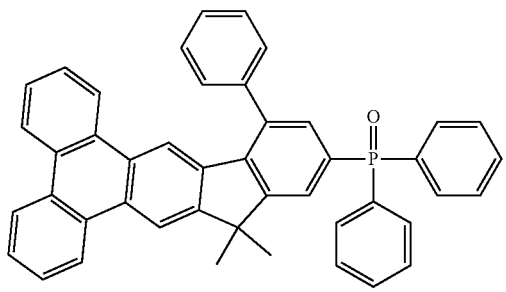
A117
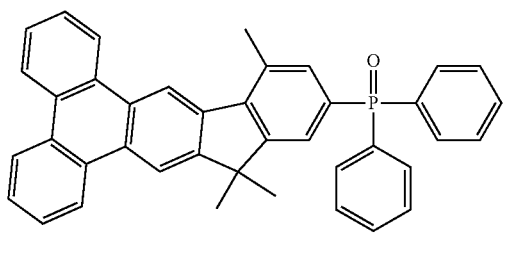
A118
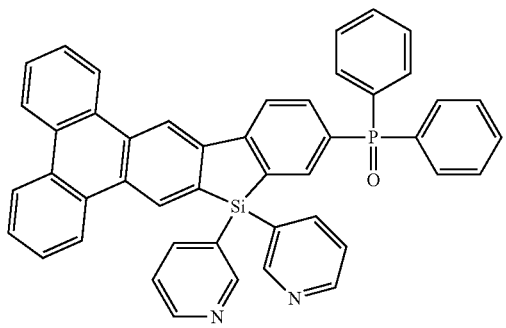
A119
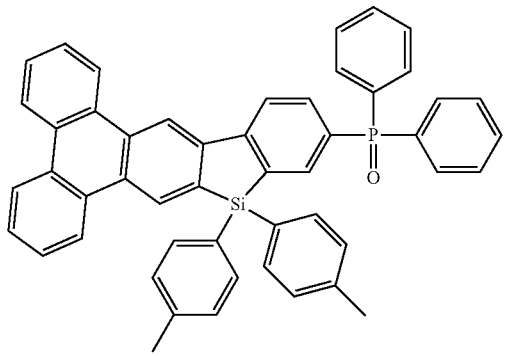
A120
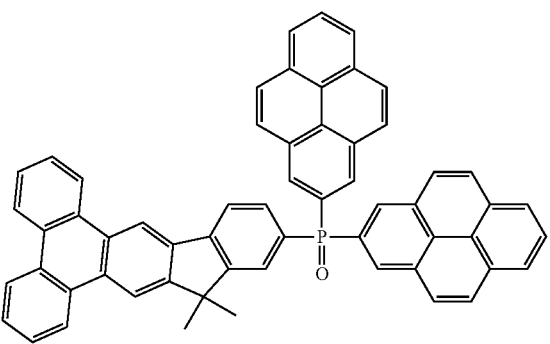
A121
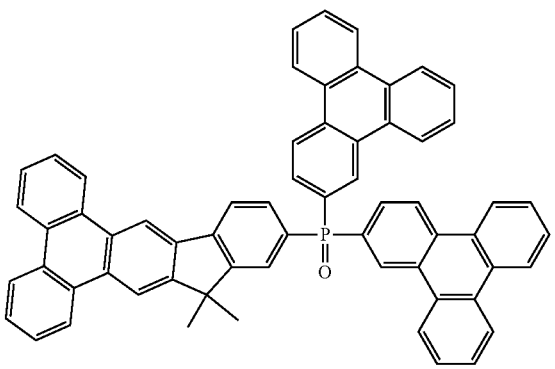
A122
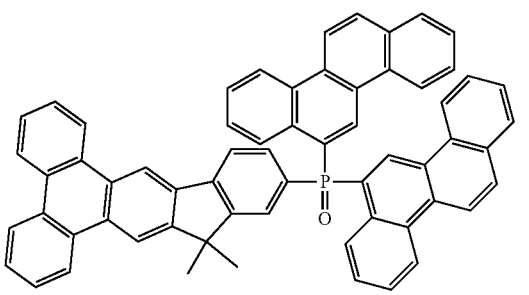
A123
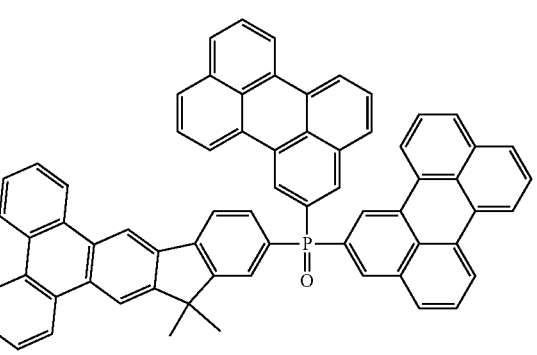
A124
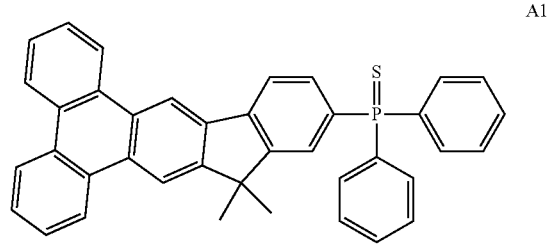
A125
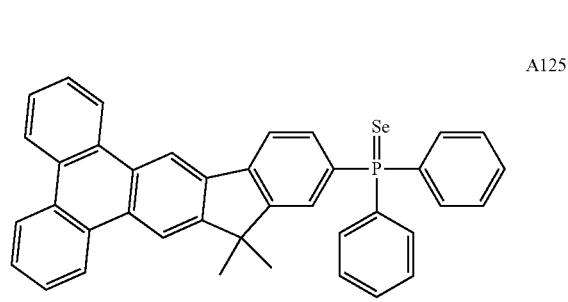

A126
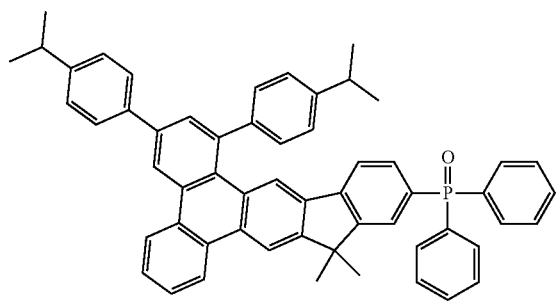
A127
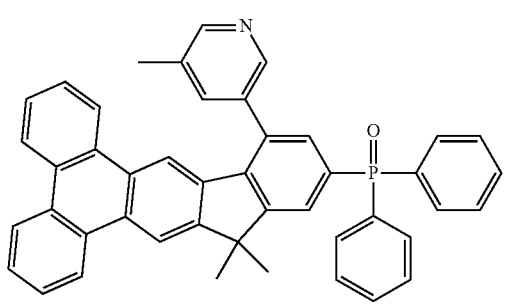
A128
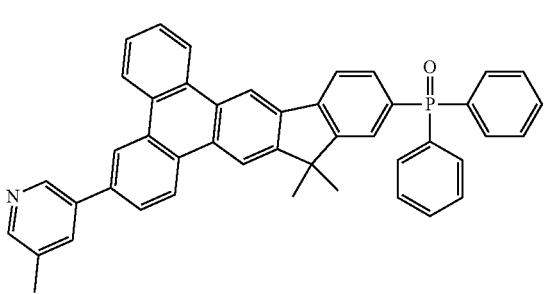
A129
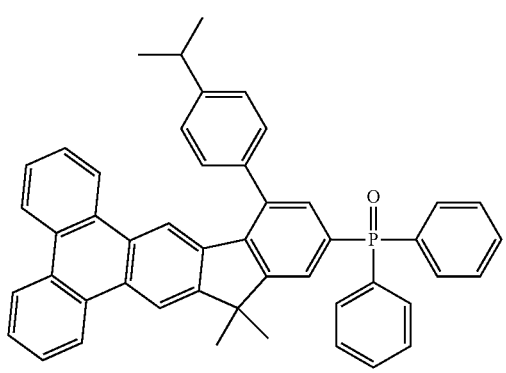
A130
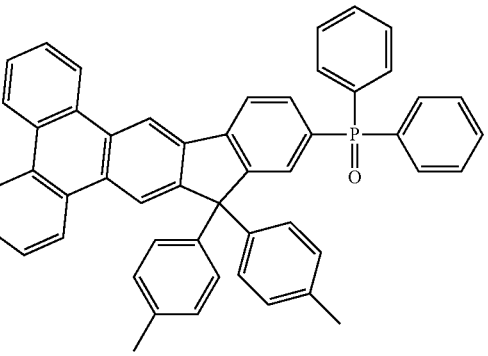
A131
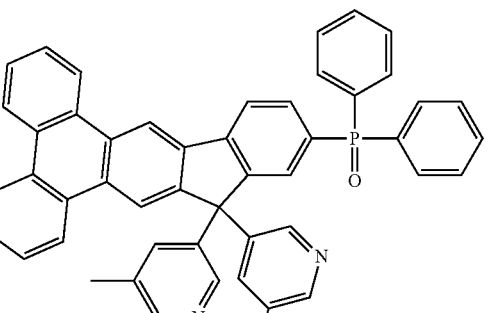
A132
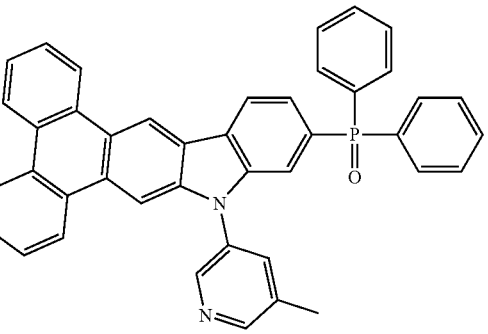
A133
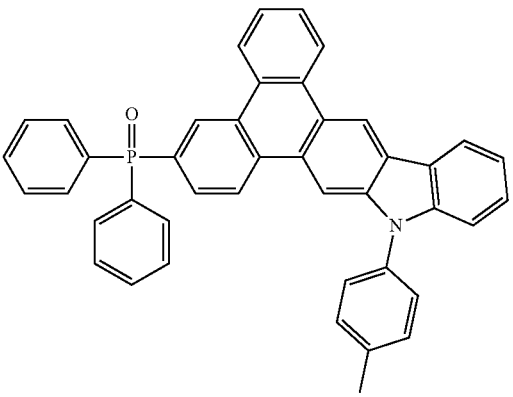

A134
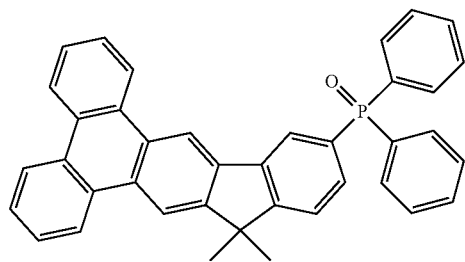
A135
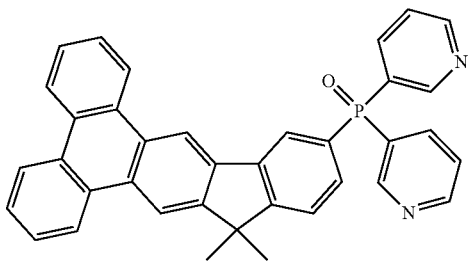
A136
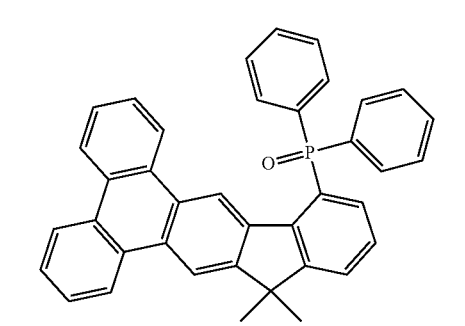
A137
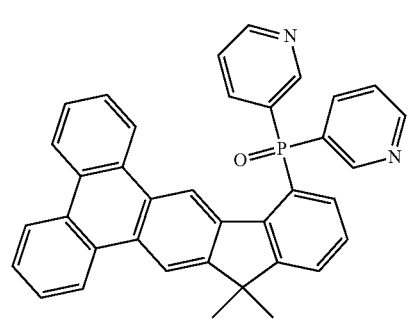
A138
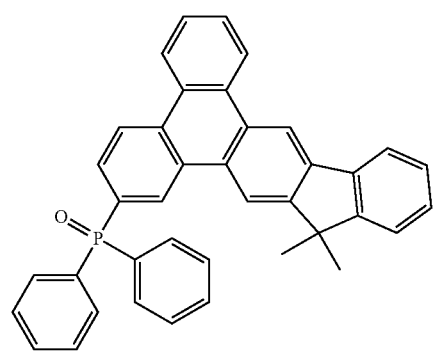
A139
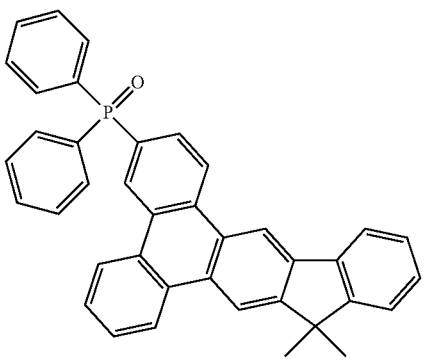
A140
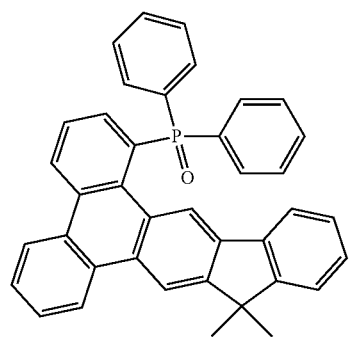
A141
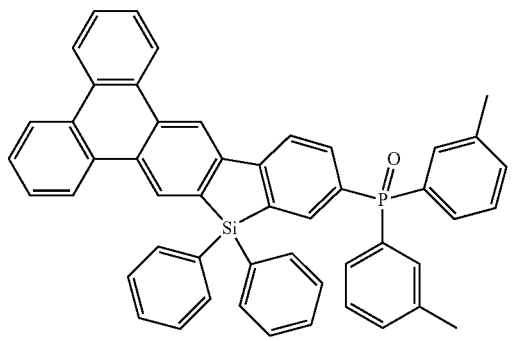
A142
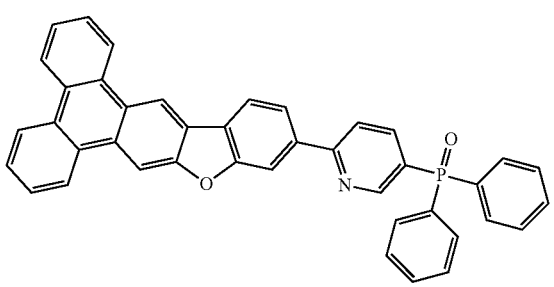

-continued

A143

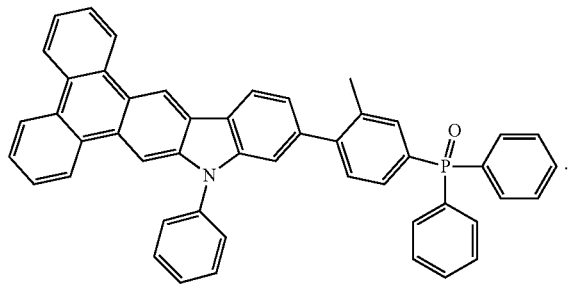

In another embodiment of the present invention, an organic electroluminescence device is disclosed. The organic electroluminescence device comprises a pair of electrodes composed of a cathode and an anode, and a light emitting layer and one or more organic thin film layers between the pair of electrodes. At least one of the light emitting layer and the organic thin film layer comprises the indenotriphenylene derivative of formula (A).

In some embodiments, the light emitting layer comprising the indenotriphenylene derivative of formula (A) is a phosphorescent host material. The light emitting layer may further comprise a phosphorescent dopant material. The phosphorescent dopant material may be any well-known dopant material used in the phosphorescence emitting organic EL device. Preferably, the phosphorescent dopant material is an iridium (Ir) complex.

In some embodiments, the organic thin film layer comprising the indenotriphenylene derivative of formula (A) is an electron transporting layer. In certain embodiments, the organic thin film layer comprising the indenotriphenylene derivative of formula (A) is a hole blocking layer.

In a further embodiment of the present invention, the organic electroluminescence device is a lighting panel. In other embodiment of the present invention, the organic electroluminescence device is a backlight panel.

Detailed preparation of the indenotriphenylene derivatives of the present invention will be clarified by exemplary embodiments below, but the present invention is not limited thereto. EXAMPLES 1-8 show the preparation of the indenotriphenylene derivatives of the present invention, and EXAMPLES 9-10 show the fabrication and test report of the organic EL devices.

SYNTHESIS EXAMPLES

Synthesis of 2-(biphenyl-2-yl)-7-bromo-9,9-dimethyl-9H-fluorene

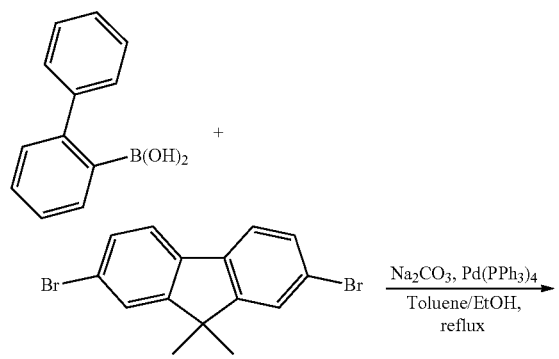

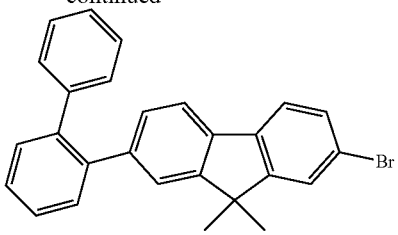

A mixture of 35.2 g (100 mmol) of 2,7-dibromo-9,9-dimethyl-9H-fluorene, 21.8 g (110 mmol) of 2-biphenylboronic acid, 2.31 g (2 mmol) of Pd(PPh$_3$)$_4$, 75 ml of 2 M Na$_2$CO$_3$, 150 ml of EtOH, and 300 ml of toluene was degassed and placed under nitrogen, and then heated at 100° C. for 12 hrs. After the reaction finished, the mixture was allowed to cool to room temperature. The organic layer was extracted with ethyl acetate and water, and then dried with anhydrous magnesium sulfate. Subsequently, the solvent was removed and then the residue was purified by column chromatography on silica to give the product (26.8 g, 63.0 mmol, 63%) as a white solid.

Synthesis of 12-bromo-10,10-dimethyl-10H-indeno[2,1-b]-triphenylene

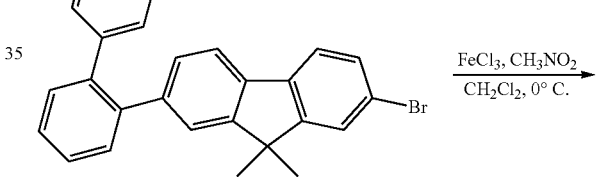

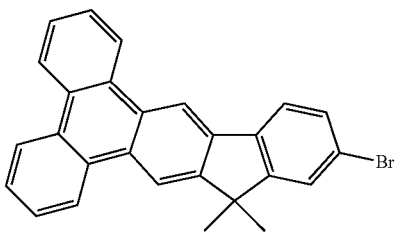

In a 3000 ml three-necked flask that had been degassed and filled with nitrogen, 26.8 g (60 mmol) of 2-(biphenyl-2-yl)-7-bromo-9,9-dimethyl-9H-fluorene was dissolved in anhydrous dichloromethane (1500 ml), and then 97.5 g (600 mmol) of Iron(III) chloride was added thereto. After stirring for one hour at 0° C., 500 ml of nitromathane was added thereto. Subsequently, the organic layer was separated, and then the solvent was removed in vacuum. The residue was purified by column chromatography on silica (hexane-dichloromethane) to afford a white solid (10.7 g, 25.3 mmol, 40%). $^1$H NMR (CDCl$_3$, 400 MHz): chemical shift (ppm) 8.95 (s, 1H), 8.79~8.74 (m, 2H), 8.69~8.68 (m, 3H), 7.84 (d, J=8.0 Hz, 1H), 7.72~7.65 (m, 5H), 7.57 (d, J=8.0 Hz, 1H), 1.66 (s, 6H).

Synthesis of 2-(10,10-dimethyl-10H-indeno[2,1-b]triphenylen-12-yl)-4,4,5,5-tetramethyl-1,3,2-dioxaborolane

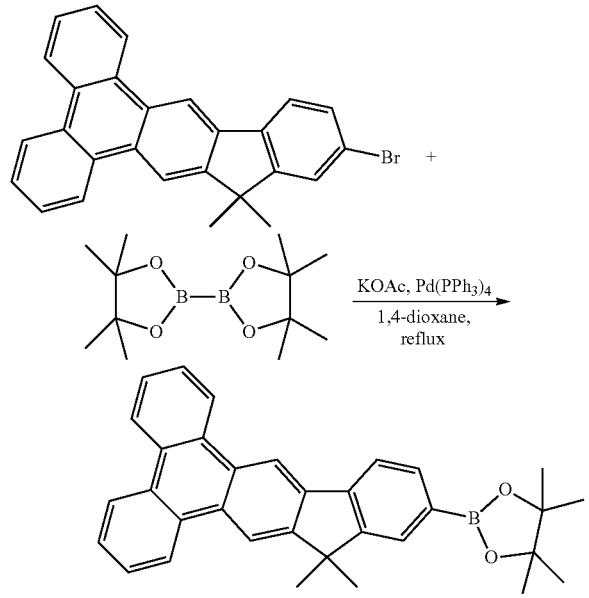

A mixture of 10.7 g (25.3 mmol) of 12-bromo-10,10-dimethyl-10H-indeno-[2,1-b]triphenylene, 7.7 g (30.3 mmol) of bis(pinacolato)diboron, 0.3 g (0.26 mmol) of Pd(PPh₃)₄, 7.4 g (75.4 mmol) of potassium acetate, and 300 ml of 1,4-dioxane was degassed and placed under nitrogen, and then heated at 90° C. for 16 hrs. After the reaction finished, the mixture was allowed to cool to room temperature. The organic phase was separated, washed with ethyl acetate and water, and then dried over magnesium sulfate. The solvent was removed in vacuum. The residue was purified by column chromatography on silica (hexane-dichloromethane) to give the target product (9.5 g, 20.2 mmol, 80%) as a light-yellow solid; ¹HNMR (CDCl₃, 400 MHz): chemical shift (ppm) 9.03 (s, 1H), 8.81 (d, J=7.84 Hz, 1H), 8.77 (d, J=7.88 Hz, 1H), 8.70~8.67 (m, 3H), 8.02~7.93 (m, 3H), 7.71~7.67 (m, 4H), 1.69 (s, 6H), 1.42 (s, 12H).

Synthesis of 9,9-dimethyl-2-(5-nitrobiphenyl-2-yl)-9H-fluorene

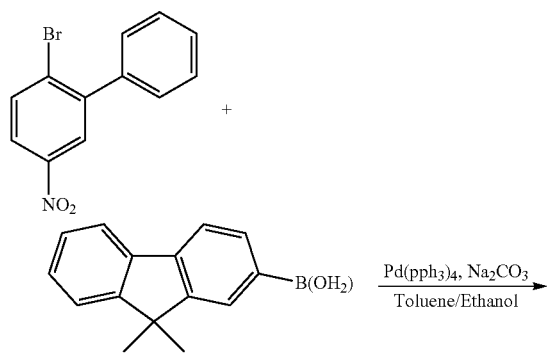

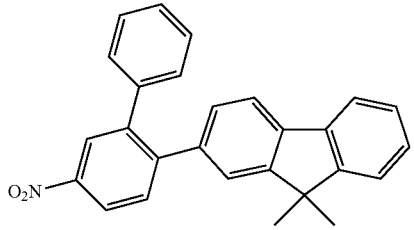

A mixture of 40 g (14.38 mmol) of 2-bromo-5-nitrobiphenyl, 27.7 g (15.82 mmol) of 9,9-dimethyl-9H-fluoren-2-ylboronic acid, 1.8 g (0.16 mmol) of Pd(PPh₃)₄, 119 ml of 2 M Na₂CO₃, 150 ml of EtOH, and 450 ml of toluene was degassed and placed under nitrogen, and then heated at 100° C. overnight. After the reaction finished, the mixture was allowed to cool to room temperature. The solution was extracted with dichloromethane and water. The organic layer was dried with anhydrous magnesium sulfate and the solvent was evaporated under reduced pressure. The residue was purified by column chromatography on silica to give the product (43.1 g, 110.1 mmol, 69.6%). ¹H NMR (CDCl₃, 400 MHz): chemical shift (ppm) 7.93 (s, 1H), 7.71 (d, 1H), 7.50 (d, 1H), 7.38~7.21 (m, 6H), 7.16~6.92 (m, 4H), 6.83~6.65 (m, 2H), 1.15 (s, 6H).

Synthesis of 6-(9,9-dimethyl-9H-fluoren-2-yl)biphenyl-3-amine

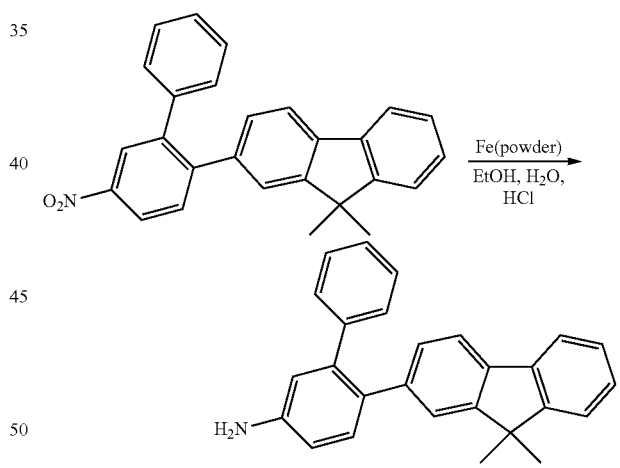

A mixture of 10.4 g (26.56 mmol) of 9,9-dimethyl-2-(5-nitrobiphenyl-2-yl)-9H-fluorene, 8.5 g (159.36 mmol) of iron powder, and 10 ml of conc. HCl was refluxed in aqueous ethanol (100 mL of alcohol and 30 mL of water) at 85° C. for 2 hrs. Afterwards, the reaction mixture was filtered, and then the filtrate was extracted with ethyl acetate and water. The organic layer was dried with anhydrous magnesium sulfate and the solvent was evaporated under reduced pressure. The resulting solid was washed with hexane to give the product (8.2 g, 22.68 mmol, 85%). ¹H NMR (CDCl₃, 400 MHz): chemical shift (ppm) 7.71 (d, 1H), 7.64 (d, 1H), 7.42 (d, 1H), 7.29~7.12 (m, 7H), 7.06 (d, 2H), 6.89 (s, 1H), 6.80 (d, 1H), 6.78 (s, 1H), 4.47 (s, 2H), 1.12 (s, 6H).

Synthesis of
2-(5-bromobiphenyl-2-yl)-9,9-dimethyl-9H-fluorene

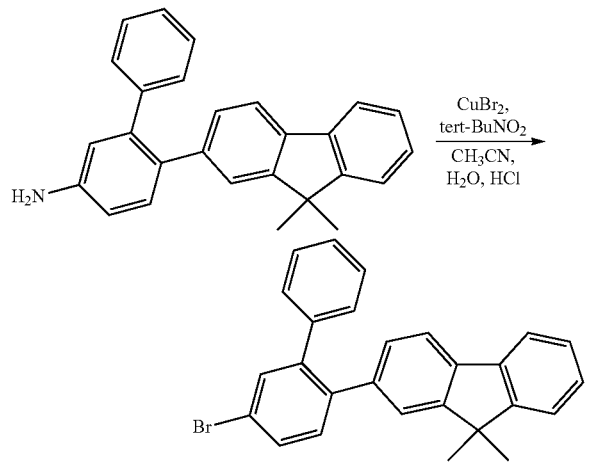

To a refluxing mixture of 0.34 g (3.32 mmol) of tert-butyl nitrite, 0.6 g (2.76 mmol) of anhydrous copper(II) bromide, and anhydrous acetonitrile (46 mL), 1 g (2.76 mmol) of 6-(9,9-dimethyl-9H-fluoren-2-yl)biphenyl-3-amine was added slowly over a period of 1 hr, giving rise to a reaction with vigorous foaming and evolution of nitrogen gas. After completion of the reaction, the mixture was cooled to room temperature and then poured into the aqueous HCl solution. The crude precipitate was purified by column chromatography on silica to give the product (0.3 g, 0.70 mmol, 25%). $^1$H NMR (CDCl$_3$, 400 MHz): chemical shift (ppm) 7.81 (d, 1H), 7.68~7.66 (m, 1H), 7.63~7.61 (m, 1H), 7.37~7.35 (m, 1H), 7.32~7.24 (m, 4H), 7.22~7.16 (m, 4H), 7.12~7.09 (m, 2H), 6.93 (d, 1H), 1.20 (s, 6H).

Synthesis of 6-bromo-10,10-dimethyl-10H-indeno
[2,1-b]triphenylene

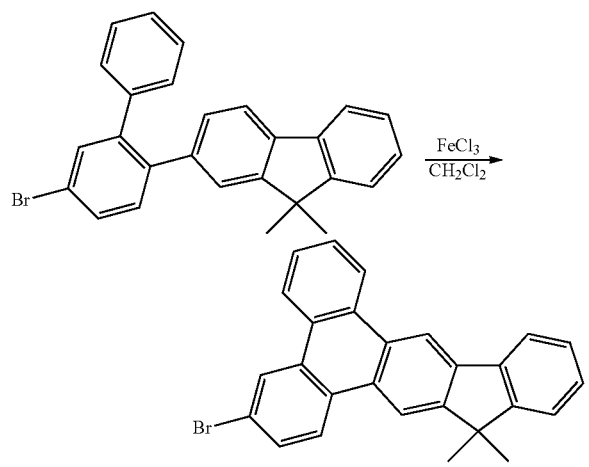

In a 100 ml three-necked flask that had been degassed and filled with nitrogen, 2.9 g (0.68 mmol) of 2-(5-bromobiphenyl-2-yl)-9,9-dimethyl-9H-fluorene was dissolved in anhydrous dichloromethane (180 ml), and then 5.5 g (3.40 mmol) of iron(III) chloride was added thereto. After stirring for one hour at 0° C., the reaction was quenched with methanol and water. Subsequently, the organic layer was separated, and then the solvent was removed. The residue was purified by column chromatography on silica to afford a white solid (1.7 g, 0.81 mmol, 58.6%). $^1$H NMR (CDCl$_3$, 400 MHz): chemical shift (ppm) 9.01 (s, 1H), 8.94 (d, 2H), 8.78 (s, 1H), 8.58 (s, 1H), 8.49 (s, 1H), 7.98 (d, 1H), 7.85~7.78 (m, 2H), 7.63~7.43 (m, 4H), 1.69 (s, 6H).

Synthesis of 2-(10,10-dimethyl-10H-indeno[2,1-b]
triphenylen-6-yl)-4,4,5,5-tetramethyl-1,3,2-dioxa-
borolane

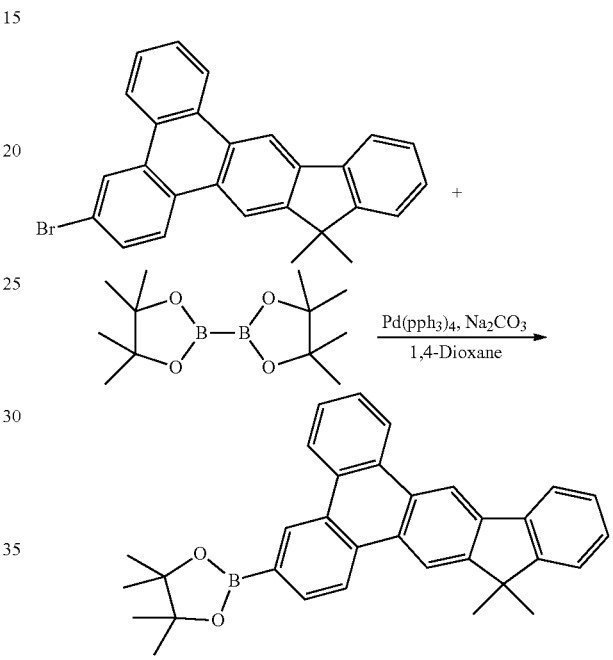

A mixture of 3 g (7 mmol) of 6-bromo-10,10-dimethyl-10H-indeno [2,1-b]triphenylene, 2.16 g (8.4 mmol) of bis(pinacolato)diboron, 0.16 g (0.14 mmol) of Pd(PPh$_3$)$_4$, 30 ml of 2 M Na$_2$CO$_3$, and 50 ml of 1,4-dioxane was degassed and placed under nitrogen, and then heated at 100° C. for 12 hrs. After the reaction finished, the mixture was allowed to cool to room temperature. The organic layer was extracted with ethyl acetate and water, and then dried with anhydrous magnesium sulfate. Subsequently, the solvent was removed, and then the residue was purified by column chromatography on silica to give the product (2.27 g, 4.8 mmol, 69%) as a white solid.

Synthesis of 3-(biphenyl-2-yl)-7-bromodibenzo[b,d]
furan

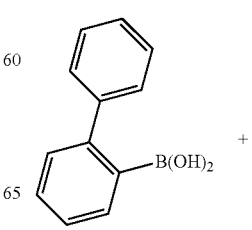

-continued

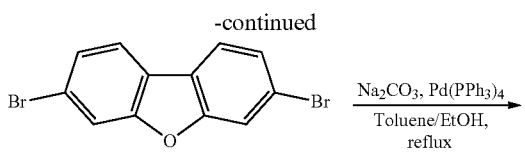

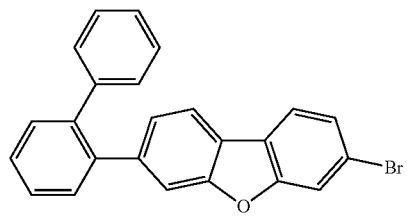

A mixture of 30 g (92 mmol) of 3,7-dibromodibenzo[b,d]furan, 20 g (110 mmol) of 2-biphenylboronic acid, 2.13 g (2 mmol) of Pd(PPh$_3$)$_4$, 75 ml of 2 M Na$_2$CO$_3$, 150 ml of EtOH, and 300 ml of toluene was degassed and placed under nitrogen, and then heated at 100° C. for 12 hrs. After the reaction finished, the mixture was allowed to cool to room temperature. The organic layer was extracted with ethyl acetate and water, and then dried with anhydrous magnesium sulfate. Subsequently, the solvent was removed and then the residue was purified by column chromatography on silica to give the product (23.9 g, 59.8 mmol, 65%) as a white solid.

Synthesis of 12-bromobenzo[d]triphenyleno[2,3-b]furan

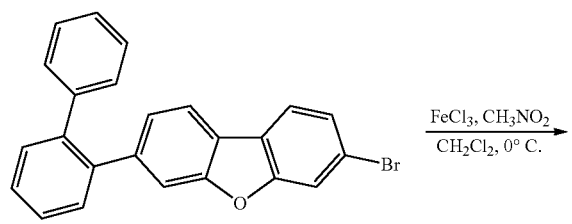

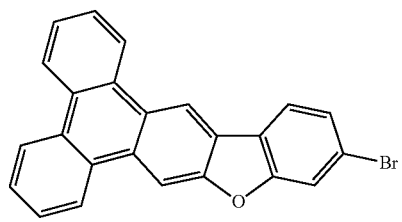

In a 3000 ml three-necked flask that had been degassed and filled with nitrogen, 23.9 g (59.8 mmol) of 3-(biphenyl-2-yl)-7-bromodibenzo[b,d]-furan was dissolved in anhydrous dichloromethane (1500 ml), and then 97 g (598 mmol) of Iron(III) chloride was added thereto. After stirring for one hour at 0° C., 500 ml of nitromathane was added thereto. Subsequently, the organic layer was separated, and then the solvent was removed in vacuum. The residue was purified by column chromatography on silica (hexane-dichloromethane) to afford a white solid (10.2 g, 25.6 mmol, 42%).

Synthesis of 2-(benzo[d]triphenyleno[2,3-b]furan-12-yl)-4,4,5,5-tetramethyl-1,3,2-dioxaborolane

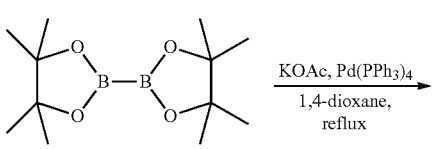

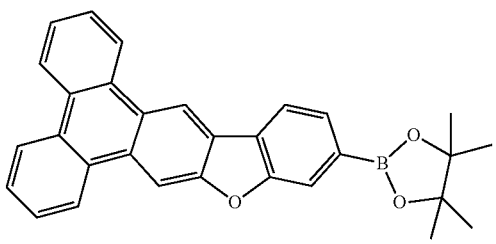

A mixture of 10.2 g (25.6 mmol) of 12-bromobenzo[d]triphenyleno-[2,3-b]furan, 7.8 g (30.7 mmol) of bis(pinacolato)diboron, 0.6 g (0.51 mmol) of Pd(PPh$_3$)$_4$, 7.5 g (76.8 mmol) of potassium acetate, and 300 ml of 1,4-dioxane was degassed and placed under nitrogen, and then heated at 90° C. for 16 hrs. After the reaction finished, the mixture was allowed to cool to room temperature. Subsequently, the organic phase was separated, washed with ethyl acetate and water, and then dried over magnesium sulfate. The solvent was removed in vacuum. The residue was purified by column chromatography on silica (hexane-dichloromethane) to give the target product (9.4 g, 21.1 mmol, 83%) as a light-yellow solid.

Synthesis of 3-(biphenyl-2-yl)-7-bromodibenzo[b,d]thiophene

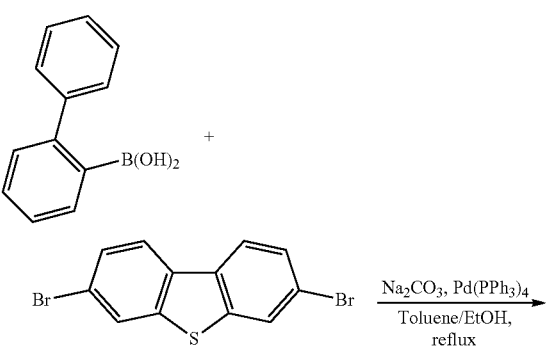

-continued

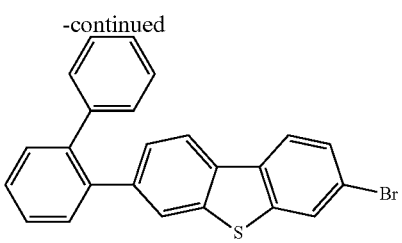

A mixture of 30 g (87.7 mmol) of 3,7-dibromodibenzo[b,d]thiophene, 19.1 g (96.4 mmol) of 2-biphenylboronic acid, 2.0 g (1.8 mmol) of Pd(PPh$_3$)$_4$, 75 ml of 2 M Na$_2$CO$_3$, 150 ml of EtOH, and 300 ml of toluene was degassed and placed under nitrogen, and then heated at 100° C. for 12 hrs. After the reaction finished, the mixture was allowed to cool to room temperature. The organic layer was extracted with ethyl acetate and water, and then dried with anhydrous magnesium sulfate. Subsequently, the solvent was removed and then the residue was purified by column chromatography on silica to give the product (22.9 g, 55.2 mmol, 63%) as a white solid.

Synthesis of 12-bromobenzo[d]triphenyleno[2,3-b]thiophene

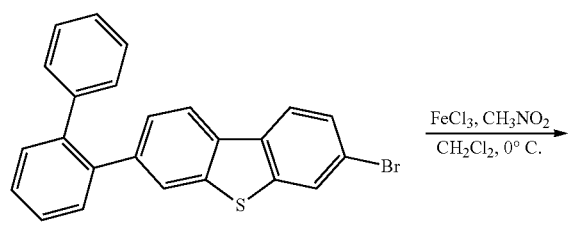

In a 3000 ml three-necked flask that had been degassed and filled with nitrogen, 22.9 g (55.2 mmol) of 3-(biphenyl-2-yl)-7-bromodibenzo[b,d]-thiophene was dissolved in anhydrous dichloromethane (1500 ml), and then 89.5 g (552 mmol) of Iron(III) chloride was added thereto. After stirring for one hour, 500 ml of nitromathane was added thereto. Subsequently, the organic layer was separated, and then the solvent was removed in vacuum. The residue was purified by column chromatography on silica (hexane-dichloromethane) to afford a white solid (12 g, 29.2 mmol, 53%).

Synthesis of 2-(benzo[d]triphenyleno[2,3-b]thiophen-12-yl)-4,4,5,5-tetramethyl-1,3,2-dioxaborolane

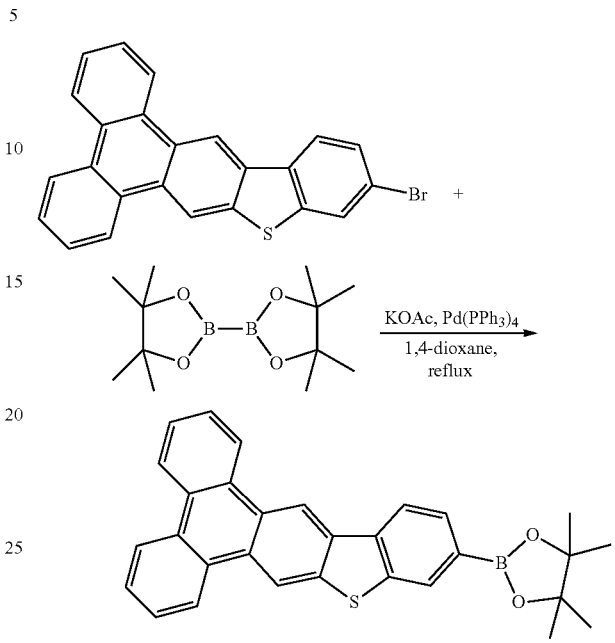

A mixture of 12 g (29.2 mmol) of 12-bromobenzo[d]triphenyleno[2,3-b]thiophene, 8.9 g (35.0 mmol) of bis(pinacolato)diboron, 0.6 g (0.58 mmol) of Pd(PPh$_3$)$_4$, 8.6 g (87.6 mmol) of potassium acetate, and 300 ml of 1,4-dioxane was degassed and placed under nitrogen, and then heated at 90° C. for 16 hrs. After the reaction finished, the mixture was allowed to cool to room temperature. The organic phase was separated, washed with ethyl acetate and water, and then dried over magnesium sulfate. The solvent was removed in vacuum. The residue was purified by column chromatography on silica (hexane-dichloromethane) to give the target product (10.4 g, 22.6 mmol, 78%) as a light-yellow solid.

Synthesis of 2-(4-bromo-2-nitrophenyl)triphenylene

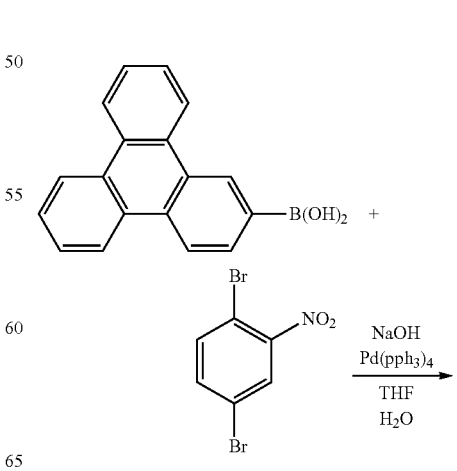

-continued

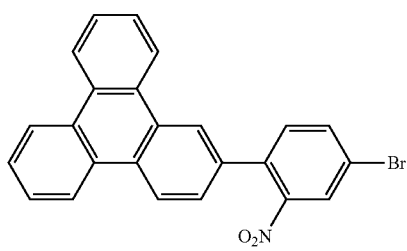

A mixture of 15 g (55.1 mmol) of triphenylen-2-ylboronic acid, 15.5 g (55.1 mmol) of 1,4-dibromo-2-nitrobenzene, 1.3 g (1.12 mmol) of Pd(PPh$_3$)$_4$, 6.6 g (0.17 mol) of sodium hydroxide, 150 ml of H$_2$O, and 300 ml of THF was degassed and placed under nitrogen, and then heated at 90° C. for 16 hrs. After the reaction finished, the mixture was allowed to cool to room temperature. Subsequently, the organic phase was separated, washed with ethyl acetate and water, and then dried over magnesium sulfate. The solvent was removed in vacuum. The residue was purified by column chromatography on silica (hexane-dichloromethane) to give the target product (16.7 g, 38.9 mmol, 71%) as a yellow solid.

Synthesis of
12-bromo-10H-phenanthro[9,10-b]carbazole

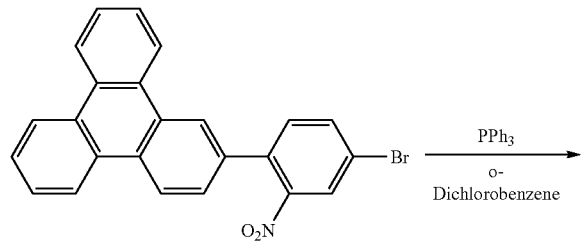

A mixture of 16.7 g (38.9 mmol) of 2-(4-bromo-2-nitrophenyl)-triphenylene, 20.4 g (77.7 mmol) of triphenylphosphine, and 200 ml of o-Dichlorobenzene was degassed and placed under nitrogen, and then heated at 180° C. for 6 hrs. After the reaction finished, the mixture was allowed to cool to room temperature. Afterwards, the organic phase was separated, washed with ethyl acetate and water, and then dried over magnesium sulfate. The solvent was removed in vacuum. The residue was purified by column chromatography on silica (hexane-dichloromethane) to give the target product (9.4 g, 23.7 mmol, 61%) as a yellow solid.

Synthesis of 12-bromo-10-phenyl-10H-phenanthro
[9,10-b]carbazole

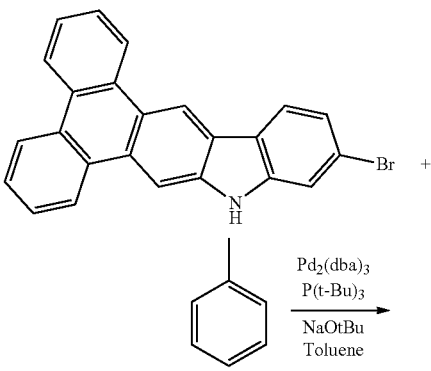

A mixture of 9.4 g (23.7 mmol) of 12-bromo-10H-phenanthro[9,10-b]carbazole, 5.3 g (26.0 mmol) of Iodobenzene, 2.31 g (2 mmol) of Pd$_2$(dba)$_3$, 10 ml of P(t-Bu)$_3$ in Toluene, 6.8 g (70.7 mmol) of NaOtBu, and 150 ml of toluene was degassed and placed under nitrogen, and then heated at 110° C. for 12 hrs. After the reaction finished, the mixture was allowed to cool to room temperature. The organic layer was extracted with ethyl acetate and water, and then dried with anhydrous magnesium sulfate. Subsequently, the solvent was removed and then the residue was purified by column chromatography on silica to give the product (5.2 g, 11.1 mmol, 47.1%) as a white solid.

Synthesis of 10-phenyl-12-(4,4,5,5-tetramethyl-1,3,
2-dioxaborolan-2-yl)-10H-phenanthro[9,10-b]carbazole

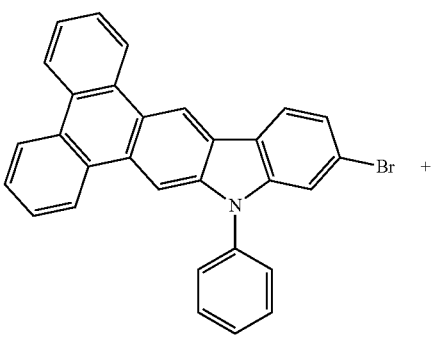

-continued

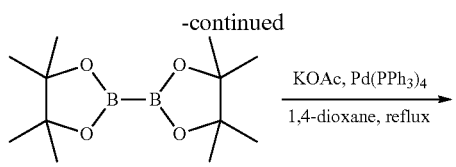

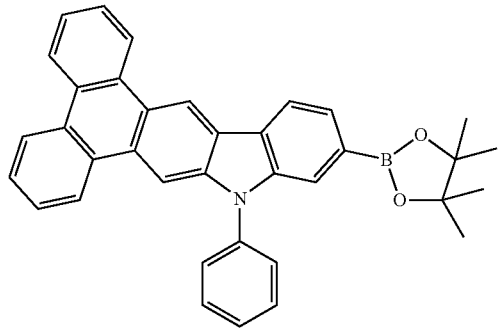

A mixture of 5.2 g (11.1 mmol) of 12-bromo-10-phenyl-10H-phenanthro[9,10-b]carbazole, 4.2 g (16.6 mmol) of bis(pinacolato)diboron, 0.26 g (0.22 mmol) of Pd(PPh$_3$)$_4$, 2.1 g (22.2 mmol) of potassium acetate, and 60 ml of 1,4-dioxane was degassed and placed under nitrogen, and then heated at 90° C. for 16 hrs. After the reaction finished, the mixture was allowed to cool to room temperature. Subsequently, the organic phase was separated, washed with ethyl acetate and water, and then dried over magnesium sulfate. The solvent was removed in vacuum. The residue was purified by column chromatography on silica (hexane-dichloromethane) to give the target product (4.9 g, 9.4 mmol, 85%) as a light-yellow solid.

Synthesis of 3,7-dibromo-5,5-diphenyl-5H-dibenzo[b,d]silole

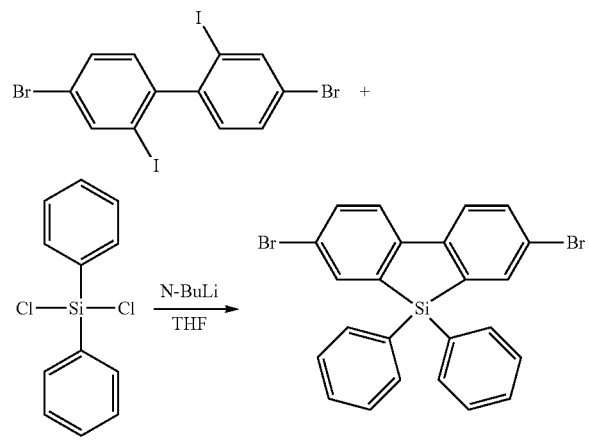

In a 500 ml three-necked flask that had been degassed and filled with nitrogen, 20 g (35.4 mmol) of 4,4'-dibromo-2,2'-diiodobiphenyl was dissolved in anhydrous THF (200 ml) at −70° C., and then 31.2 ml (77.9 mmol) of 2.5 M N-butyllithium solution was added thereto. The solution was stirred for 30 mins, followed by addition of 9.9 g (39.0 mmol) of dichlorodiphenylsilane. After stirring for one hour, the reaction was quenched by adding H$_2$O (20 mL). Subsequently, the organic layer was separated, and then the solvent was removed in vacuum. The residue was purified by column chromatography on silica (hexane-dichloromethane) to afford a light yellow solid (9.2 g, 18.6 mmol, 52.1%).

Synthesis of 3-(biphenyl-2-yl)-7-bromo-5,5-diphenyl-5H-dibenzo-[b,d]silole

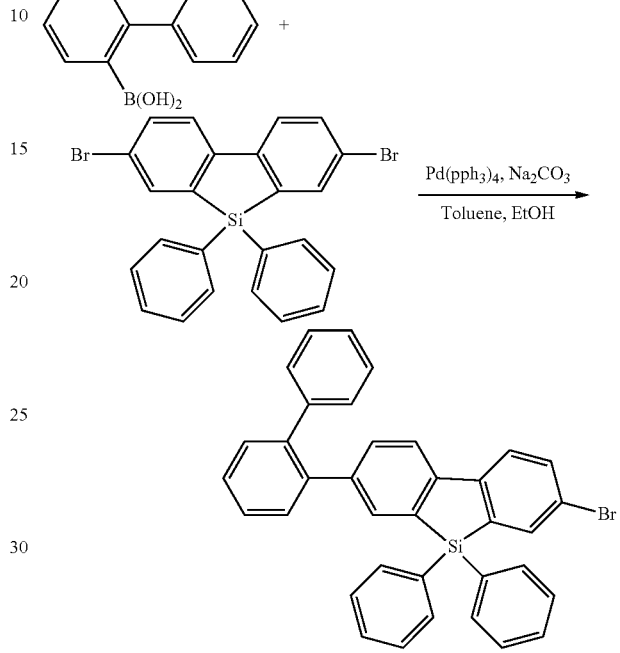

A mixture of 10 g (20.3 mmol) of 3,7-dibromo-5,5-diphenyl-5H-dibenzo[b,d]silole, 4.4 g (22.3 mmol) of 2-biphenylboronic acid, 0.23 g (0.2 mmol) of Pd(PPh$_3$)$_4$, 30 ml of 2 M Na$_2$CO$_3$, 75 ml of EtOH, and 150 ml of toluene was degassed and placed under nitrogen, and then heated at 100° C. for 12 hrs. After the reaction finished, the mixture was allowed to cool to room temperature. The organic layer was extracted with ethyl acetate and water, and then dried with anhydrous magnesium sulfate. Subsequently, the solvent was removed, and then the residue was purified by column chromatography on silica to give the product (7.6 g, 11.8 mmol, 66%) as a white solid.

Synthesis of 12-bromo-10,10-diphenyl-10H-benzo[d]triphenyleno-[2,3-b]silole

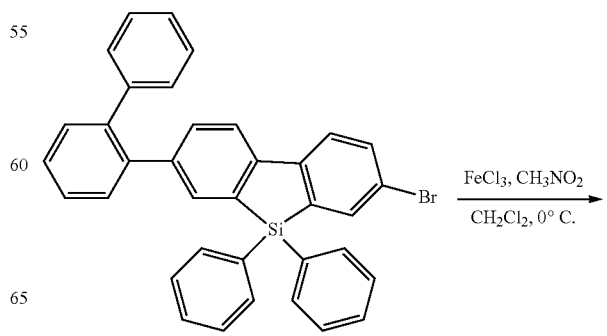

-continued

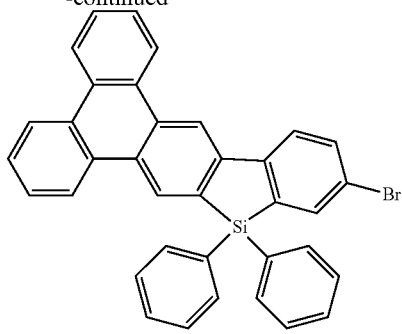

In a 3000 ml three-necked flask that had been degassed and filled with nitrogen, 7.6 g (11.8 mmol) of 3-(biphenyl-2-yl)-7-bromo-5,5-diphenyl-5H-dibenzo-[b,d]silole was dissolved in anhydrous dichloromethane (300 ml), and then 19.2 g (118 mmol) of Iron(III) chloride was added thereto. After stirring for one hour at 0° C., 150 ml of nitromathane was added thereto. Subsequently, the organic layer was separated, and then the solvent was removed in vacuum. The residue was purified by column chromatography on silica (hexane-dichloromethane) to afford a white solid (4.2 g, 6.6 mmol, 56%). MS (m/z, EI$^+$): 63911.

Example 1

Synthesis of Compound A1

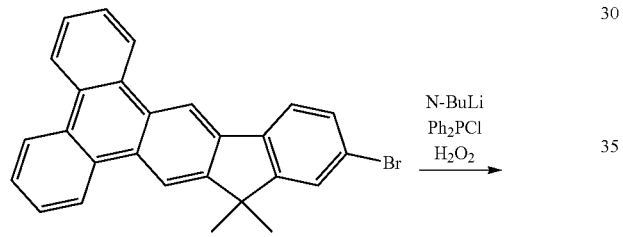

-continued

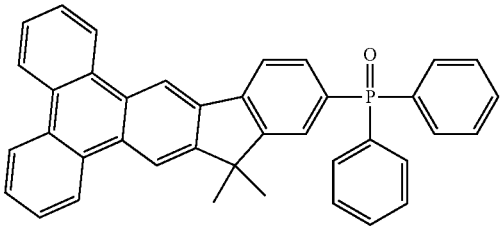

In a 100 ml three-necked flask that had been degassed and filled with nitrogen, 3 g (7.08 mmol) of 12-bromo-10,10-dimethyl-10H-indeno[2,1-b]-triphenylene was dissolved in THF (50 mL). After the solution was cooled to −78° C., n-butyllithium (2.5 M, 4.8 mL, 12.0 mmol) was added dropwise over 30 mins. After stirring for 1 hr, chlorodiphenylphosphine (Ph$_2$PCl, 1.3 g, 7.08 mmol) was added thereto. The mixture was stirred for 7 hrs and cooled to room temperature. Subsequently, the reaction was quenched by adding methanol (50 mL), and then the solvent was distilled off under reduced pressure to obtain a residue.

The residue was dissolved in DCM (100 mL), and then hydrogen peroxide solution (15 mL) was added thereto. This mixture was stirred for 7 hrs and then cooled to room temperature. The organic layer was extracted with DCM and water, and then dried with anhydrous magnesium sulfate. Afterwards, the solvent was removed and the residue was purified by column chromatography on silica to give the product (1.9 g, 3.48 mmol, 50%) as a white solid. MS (m/z, EI$^+$): 544.23.

Example 2

Synthesis of Compound A106

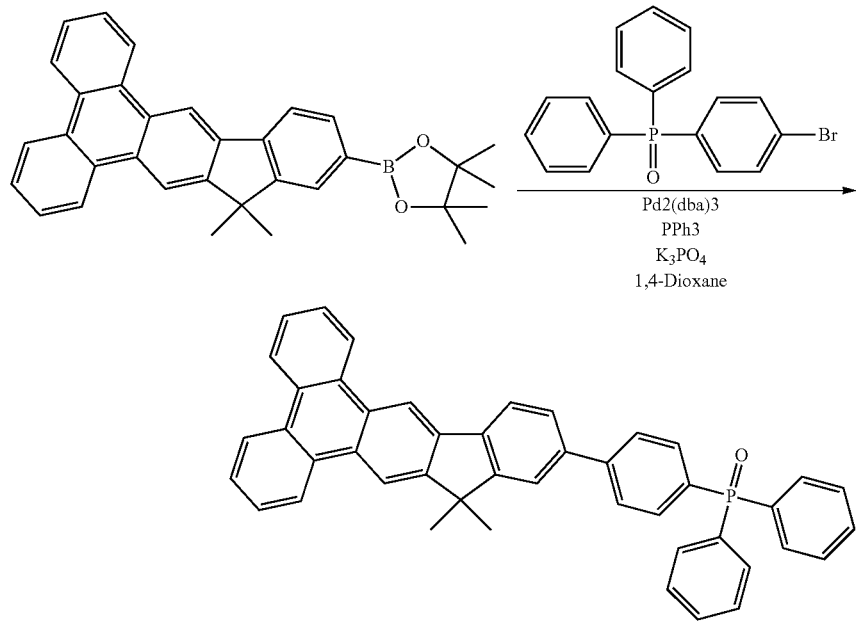

A mixture of 3 g (6.38 mmol) of 2-(10,10-dimethyl-10H-indeno[2,1-b]triphenylen-12-yl)-4,4,5,5-tetramethyl-1,3,2-dioxaborolane, 2.28 g (6.38 mmol) of (4-bromophenyl)diphenylphosphine oxide, 0.11 g (0.13 mmol) of Pd$_2$(dba)$_3$, 0.16 g (0.63 mmol) of PPh$_3$, 8.1 g (38.2 mmol) of K$_3$PO$_4$, and 100 ml of 1,4-dioxane was degassed and placed under nitrogen, and then heated to reflux for 12 hrs. After the reaction finished, the mixture was allowed to cool to room temperature. The organic layer was extracted with ethyl acetate and water, and then dried with anhydrous magnesium sulfate. Subsequently, the solvent was removed, and then the residue was purified by column chromatography on silica to give the product (2.4 g, 4.8 mmol, 62.1%) as an off-white solid. MS (m/z, EI$^+$): 620.12.

Example 3

Synthesis of Compound A51

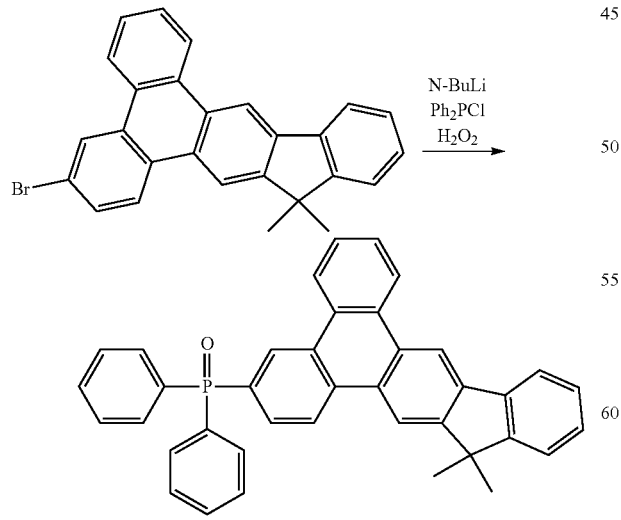

The same synthesis procedure as in EXAMPLE 1 was used, except that 6-bromo-10,10-dimethyl-10H-indeno[2,1-b]triphenylene was used instead of 12-bromo-10,10-dimethyl-10H-indeno[2,1-b]triphenylene to obtain the desired compound A51. MS (m/z, EI$^+$): 544.21.

Example 4

Synthesis of Compound A109

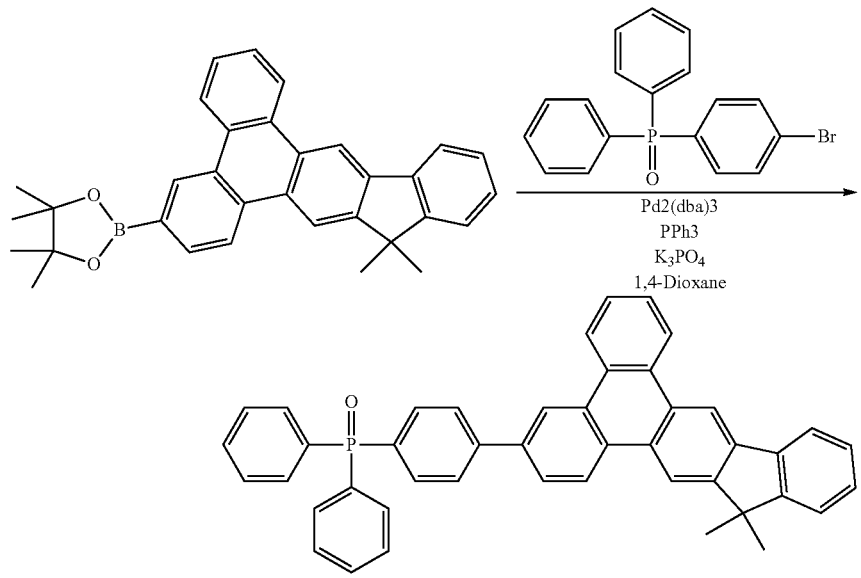

The same synthesis procedure as in EXAMPLE 2 was used, except that 2-(10,10-dimethyl-10H-indeno[2,1-b]triphenylen-6-yl)-4,4,5,5-tetramethyl-1,3,2-dioxaborolane was used instead of 2-(10,10-dimethyl-10H-indeno[2,1-b]triphenylen-12-yl)-4,4,5,5-tetramethyl-1,3,2-dioxaborolane to obtain the desired compound A109. MS (m/z, EI$^+$): 620.21.

Example 5

Synthesis of Compound A141

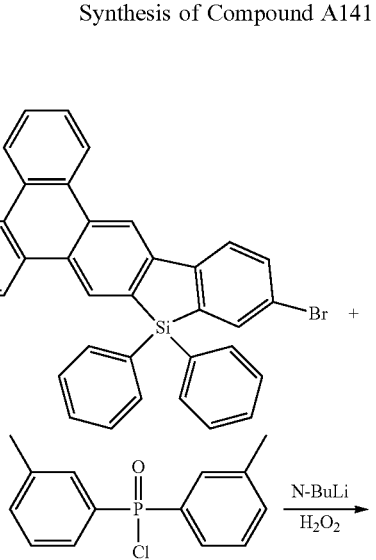

59

-continued

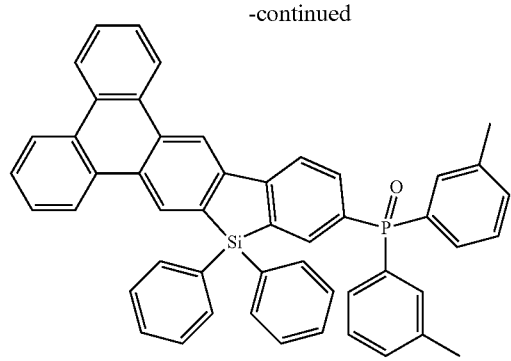

The same synthesis procedure as in EXAMPLE 1 was used, except that 12-bromo-10,10-diphenyl-10H-benzo[d]triphenyleno[2,3-b]silole was used instead of 12-bromo-10,10-dimethyl-10H-indeno[2,1-b]triphenylene, and bis(m-tolyl)phosphinyl chloride was used instead of chlorodiphenylphosphine to obtain the desired compound A141. MS (m/z, EI$^+$): 712.23.

Example 6

Synthesis of Compound A142

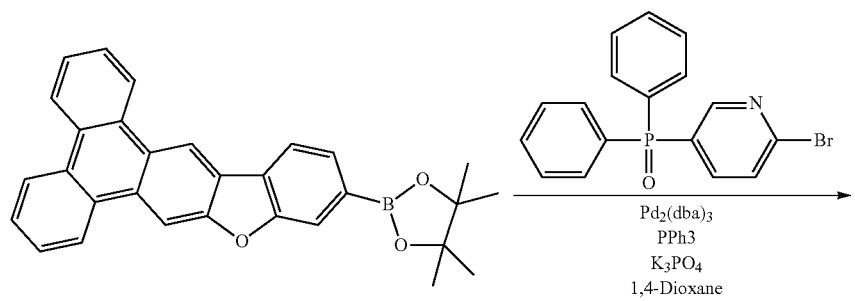

The same synthesis procedure as in EXAMPLE 2 was used, except that 2-(benzo[d]triphenyleno[2,3-b]furan-12-yl)-4,4,5,5-tetramethyl-1,3,2-dioxaborolane was used instead of 2-(10,10-dimethyl-10H-indeno[2,1-b]triphenylen-12-yl)-4,4,5,5-tetramethyl-1,3,2-dioxaborolane, and 2-bromo-5-(diphenylphosphinyl)-pyridine was used instead of (4-bromophenyl)-diphenylphosphine oxide to obtain the desired compound A142. MS (m/z, EI$^+$): 595.13.

60

Example 7

Synthesis of Compound A35

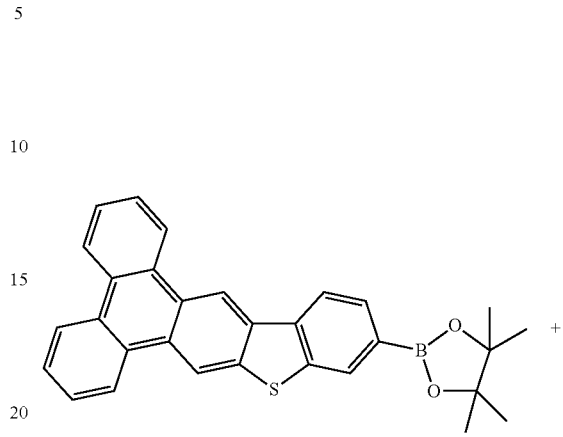

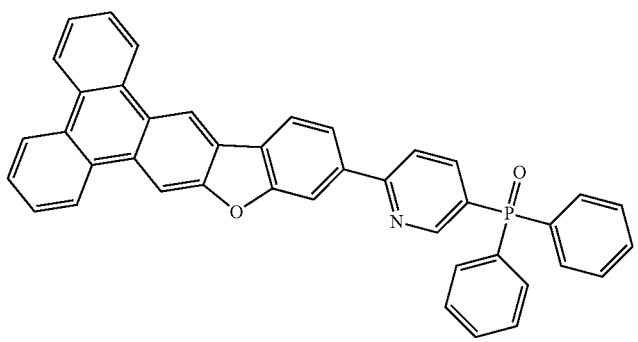

-continued

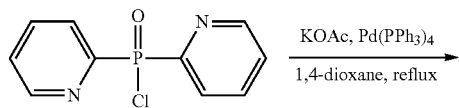

-continued

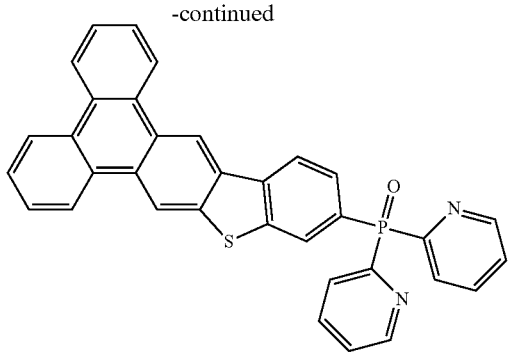

The same synthesis procedure as in EXAMPLE 2 was used, except that 2-(benzo[d]triphenyleno[2,3-b]thiophen-12-yl)-4,4,5,5-tetramethyl-1,3,2-dioxaborolane was used instead of 2-(10,10-dimethyl-10H-indeno[2,1-b]triph-enylen-12-yl)-4,4,5,5-tetramethyl-1,3,2-dioxaborolane, and dipyridin-2-ylphosphinic chloride was used instead of (4-bromophenyl)diphenylphosphine oxide to obtain the desired compound A35. MS (m/z, EI$^+$): 536.13.

Example 8

Synthesis of Compound A143

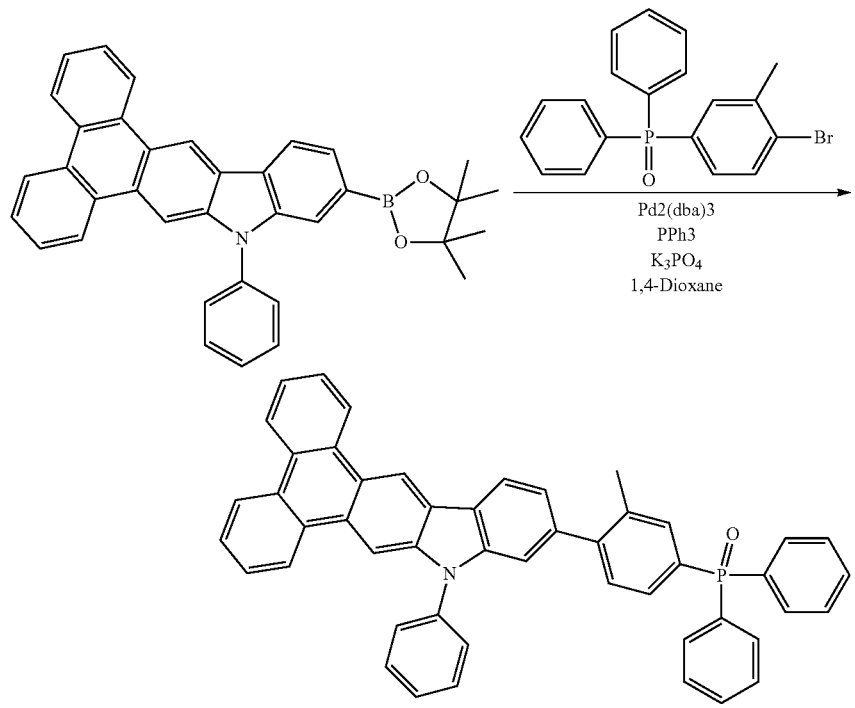

The same synthesis procedure as in EXAMPLE 2 was used, except that 10-phenyl-12-(4,4,5,5-tetramethyl-1,3,2-dioxaborolan-2-yl)-10H-phenanthro[9,10-b]carbazole was used instead of 2-(10,10-dimethyl-10H-indeno[2,1-b]triph-enylen-12-yl)-4,4,5,5-tetramethyl-1,3,2-dioxaborolane, and (4-bromo-3-methylphenyl)diphenylphosphine oxide was used instead of (4-bromophenyl)diphenylphosphine oxide to obtain the desired compound A143. MS (m/z, EI$^+$): 683.29.

General Method of Producing Organic EL Device

ITO-coated glasses with 9~12 ohm/square in resistance and 120~160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit ($10^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material. This is successfully achieved by co-vaporization from two or more sources, which means the poly-heteroaromatic compounds of the present invention are thermally stable.

Dipyrazino[2,3-f:2,3-]quinoxaline-2,3,6,7,10,11-hexacarbonitrile (HAT-CN) is used to form the hole injection layer of the organic EL device. N,N-bis(naphthalene-1-yl)-N,N-bis(phenyl)-benzidine (NPB) is used to form the hole transporting layer. 10,10-Dimethyl-12-(4-(pyren-1-yl)phenyl)-10H-indeno[1,2-b]triphenylene (PT-312, US20140175384) is used as the fluorescent host material, and N1,N1,N6,N6-tetram-tolylpyrene-1,6-diamine (D1) is used as the fluorescent dopant. Comparative Compound 1 (US 2017/0012209 A1) is used as the electron transporting material (ETM) in the organic EL devices. Bis(2-methyl-8-quinolinolate)-4-(phenylphenolato) aluminium (BAlq) is used as the hole blocking material (HBM) and phosphorescent host material. Bis(2-phenylpyridinato) (2,4-diphenyl-pyridinato)iridium (III) (D2) is used as the phosphorescent dopant. The chemical structures of conventional OLED materials and the exemplary indenotriphenylene derivatives of the present invention for producing control and exemplary organic EL devices in the present invention are shown as follows:
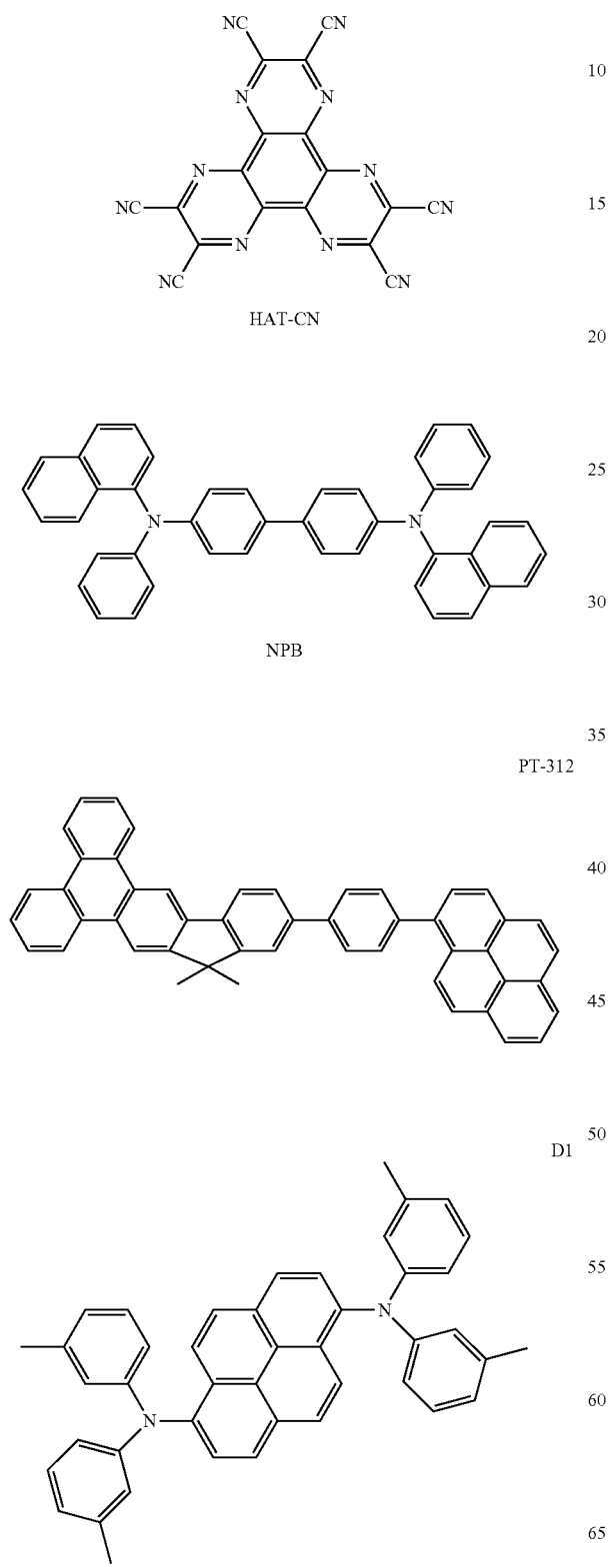
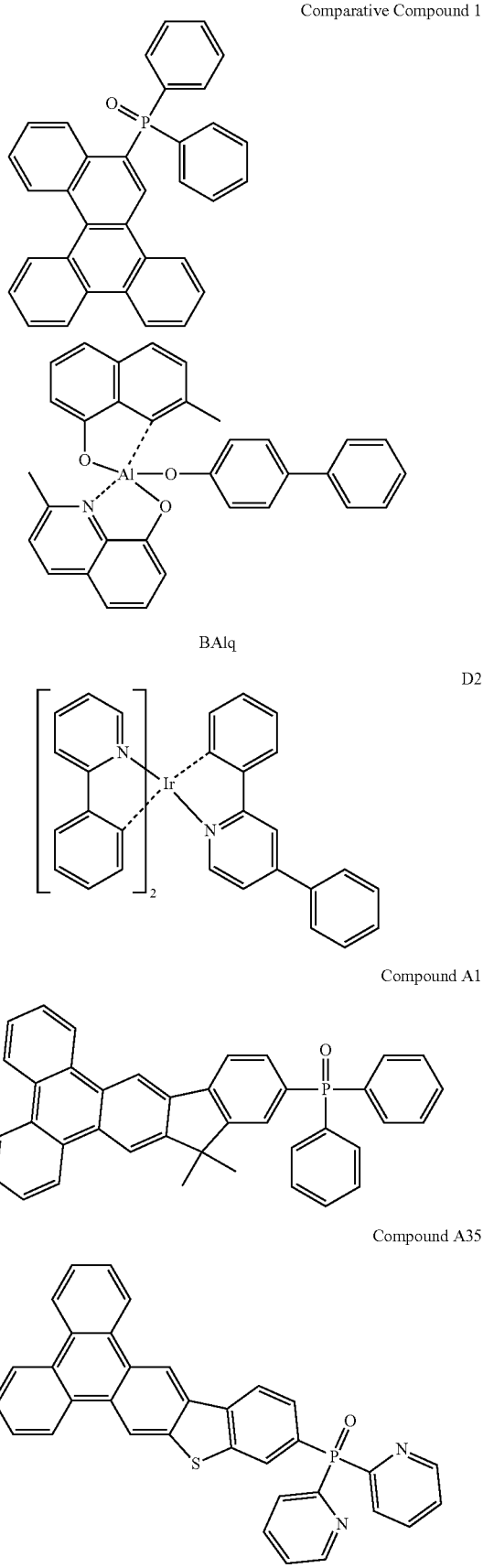

Compound A51

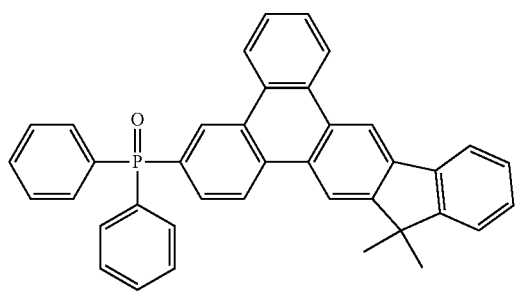

Compound A106

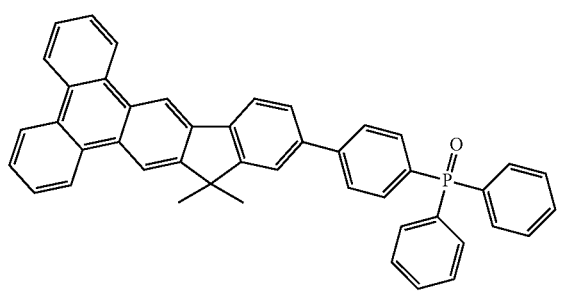

Compound A109

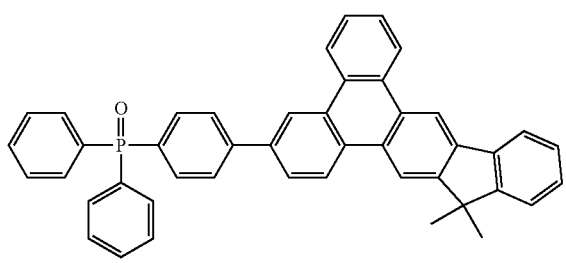

Compound A141

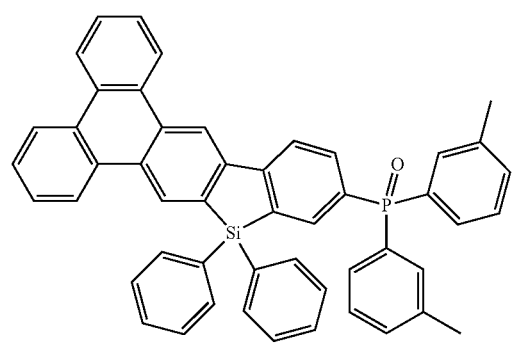

Compound A142

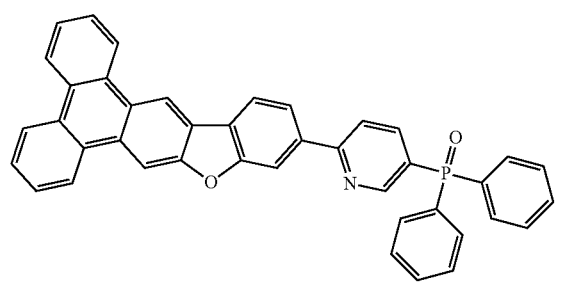

Compound A143

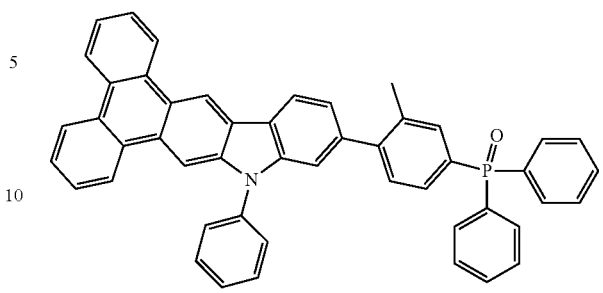

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ (as shown below), MgO, or $Li_2O$. On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

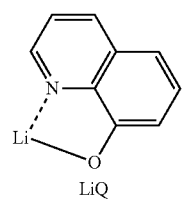

LiQ

Example 9

Using a procedure analogous to the above mentioned general method, organic EL devices emitting blue fluorescence and having the following device structure as shown in the FIGURE were produced: ITO/HAT-CN (20 nm)/NPB (130 nm)/PT-312 doped with 5% D1 (30 nm)/BAlq (10 nm)/ETM co-deposited with LiQ (ETM:LiQ=1:1; 40 nm)/LiQ (1 nm)/Al (160 nm). The I-V-B (at 1000 nits) and half-life time test reports of these blue fluorescence-emitting organic EL devices are summarized in Table 1 below. The half-life time is defined as the time the initial luminance of 1000 $cd/m^2$ has dropped to half.

TABLE 1

| ETM | Voltage (V) | Efficiency (cd/A) | CIE (y) | Half-life time (hour) |
|---|---|---|---|---|
| Comparative Compound 1 | 5.5 | 3.5 | 0.187 | 280 |
| A1 | 4.3 | 6.8 | 0.180 | 450 |
| A35 | 4.4 | 6.0 | 0.188 | 390 |

TABLE 1-continued

| ETM | Voltage (V) | Efficiency (cd/A) | CIE (y) | Half-life time (hour) |
|---|---|---|---|---|
| A51 | 4.8 | 5.1 | 0.187 | 320 |
| A106 | 4.6 | 6.3 | 0.181 | 360 |
| A109 | 5.6 | 5.6 | 0.183 | 300 |
| A141 | 4.9 | 5.2 | 0.185 | 310 |
| A142 | 4.8 | 5.5 | 0.184 | 330 |
| A143 | 5.1 | 4.9 | 0.186 | 290 |

From the above test report summary of the organic EL devices, it is obvious that the indenotriphenylene derivative of formula (A) used as the electron transporting material exhibits better performance than the prior art material Comparative Compound 1. In particular, the organic EL devices of the present invention employing the indenotriphenylene derivative of formula (A) as the electron transporting material to collocate with the host material PT-312 and the dopant material D1 have lower power consumption, higher current efficiency, and longer half-life time.

Example 10

Using a procedure analogous to the above mentioned general method, organic EL devices emitting phosphorescence and having the following device structure as shown in the FIGURE were produced: ITO/HAT-CN (20 nm)/NPB (130 nm)/co-phosphorescent host (PHhost, 1:1)+15% D2 (30 nm)/HBM (15 nm)/Compound A106 co-deposited with LiQ (Compound A106:LiQ=1:1) (40 nm)/LiQ (1 nm)/Al (160 nm). The I-V-B (at 1000 nits) and half-life time test reports of these phosphorescence-emitting organic EL devices are summarized in Table 2 below. The half-life time is defined as the time the initial luminance of 3000 cd/m² has dropped to half.

TABLE 2

| PHhost | HBM | Voltage (V) | Efficiency (cd/A) | CIE (x, y) | Half-life time (hour) |
|---|---|---|---|---|---|
| BAlq | BAlq | 5.3 | 15 | 0.45, 0.58 | 330 |
| A1 + A106 | BAlq | 5.3 | 26 | 0.43, 0.58 | 420 |
| A1 + A51 | A106 | 4.8 | 21 | 0.42, 0.56 | 400 |
| A1 + A106 | A106 | 4.4 | 38 | 0.41, 0.56 | 680 |
| A1 + A109 | A106 | 4.2 | 18 | 0.42, 0.56 | 350 |
| A35 + A106 | BAlq | 4.4 | 30 | 0.41, 0.57 | 490 |
| A51 + A106 | BAlq | 4.7 | 22 | 0.42, 0.56 | 410 |
| A109 + A106 | BAlq | 4.9 | 17 | 0.42, 0.56 | 330 |
| A141 + A106 | BAlq | 4.8 | 18 | 0.43, 0.56 | 370 |
| A142 + A106 | BAlq | 4.8 | 19 | 0.43, 0.57 | 380 |
| A143 + A106 | BAlq | 5.1 | 23 | 0.42, 0.58 | 420 |

In the above test report summary of the organic EL devices, we show that the indenotriphenylene derivative of formula (A) used as the phosphorescent host material or hole blocking material exhibits improved performance, as compared with the prior art material BAlq. In particular, the organic EL devices of the present invention employing the indenotriphenylene derivatives of formula (A) as the co-phosphorescent host materials, and/or the hole blocking material, and the electron transporting material can operate under reduced voltage, exhibit increased efficiency, and extend half-life time.

To sum up, the present invention discloses an indenotriphenylene derivative, which can be used as the phosphorescent host material of the light emitting layer, or the electron transporting material or the hole blocking material in organic EL devices. The mentioned indenotriphenylene derivative is represented by the following formula (A):

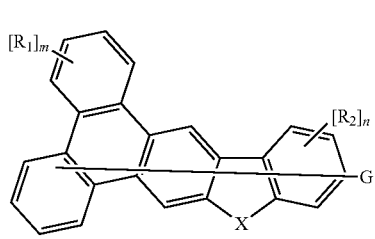

formula (A)

wherein m is 0 to 10; n is 0 to 4; X is O, S, $C(R_3)(R_4)$, $N(R_5)$, or $Si(R_6)(R_7)$; $R_1$ to $R_7$ are each independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms; and G represents formula (B) below:

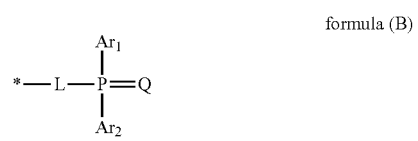

formula (B)

wherein L represents a single bond, a substituted or unsubstituted arylene group having 6 to 30 ring carbon atoms, or a substituted or unsubstituted heteroarylene group having 3 to 30 ring carbon atoms; P is a phosphorus atom; Q is an oxygen atom, a sulfur atom, or a selenium atom; $Ar_1$ and $Ar_2$ are each independently a substituted or unsubstituted aryl group having 6 to 60 ring carbon atoms, or a substituted or unsubstituted heteroaryl group having 3 to 60 ring carbon atoms; and $Ar_1$ and $Ar_2$ are optionally connected to each other to form an aromatic or heteroaromatic ring.

What is claimed is:

1. An indenotriphenylene derivative of formula (A) below:

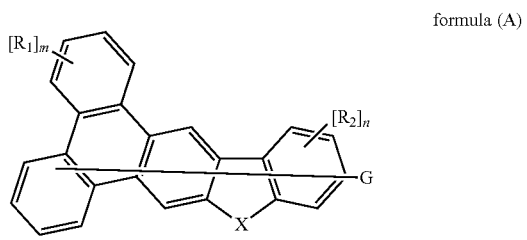

formula (A)

wherein m is 0 to 10; n is 0 to 4; X is O, S, $C(R_3)(R_4)$, $N(R_5)$, or $Si(R_6)(R_7)$; $R_1$ to $R_7$ are each independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms; and G represents formula (B) below:

formula (B)

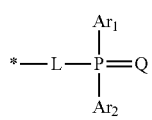

wherein L represents a single bond, a substituted or unsubstituted arylene group having 6 to 30 ring carbon atoms, or a substituted or unsubstituted heteroarylene group having 3 to 30 ring carbon atoms; P is a phosphorus atom; Q is an oxygen atom, a sulfur atom, or a selenium atom; $Ar_1$ and $Ar_2$ are each independently a substituted or unsubstituted aryl group having 6 to 60 ring carbon atoms, or a substituted or unsubstituted heteroaryl group having 3 to 60 ring carbon atoms; and $Ar_1$ and $Ar_2$ are optionally connected to each other to form an aromatic or heteroaromatic ring.

2. The indenotriphenylene derivative of claim 1, wherein the indenotriphenylene derivative is represented by the following formula (C) or formula (D):

formula (C)

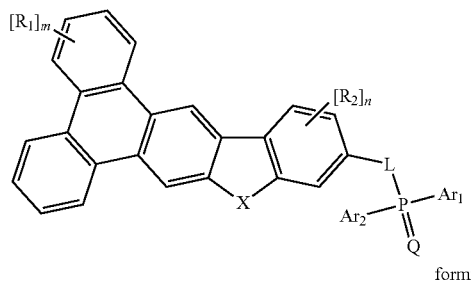

formula (D)

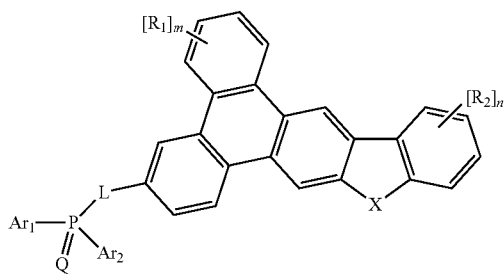

wherein m is 0 to 10; n is 0 to 4; X is O, S, $C(R_3)(R_4)$, $N(R_5)$, or $Si(R_6)(R_7)$; $R_1$ to $R_7$ are each independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms; L represents a single bond, a substituted or unsubstituted arylene group having 6 to 30 ring carbon atoms, or a substituted or unsubstituted heteroarylene group having 3 to 30 ring carbon atoms; P is a phosphorus atom; Q is an oxygen atom, a sulfur atom, or a selenium atom; and $Ar_1$ and $Ar_2$ are each independently a substituted or unsubstituted aryl group having 6 to 60 ring carbon atoms, or a substituted or unsubstituted heteroaryl group having 3 to 60 ring carbon atoms.

3. The indenotriphenylene derivative of claim 1, wherein $Ar_1$ or $Ar_2$ represents one of the following substituents:

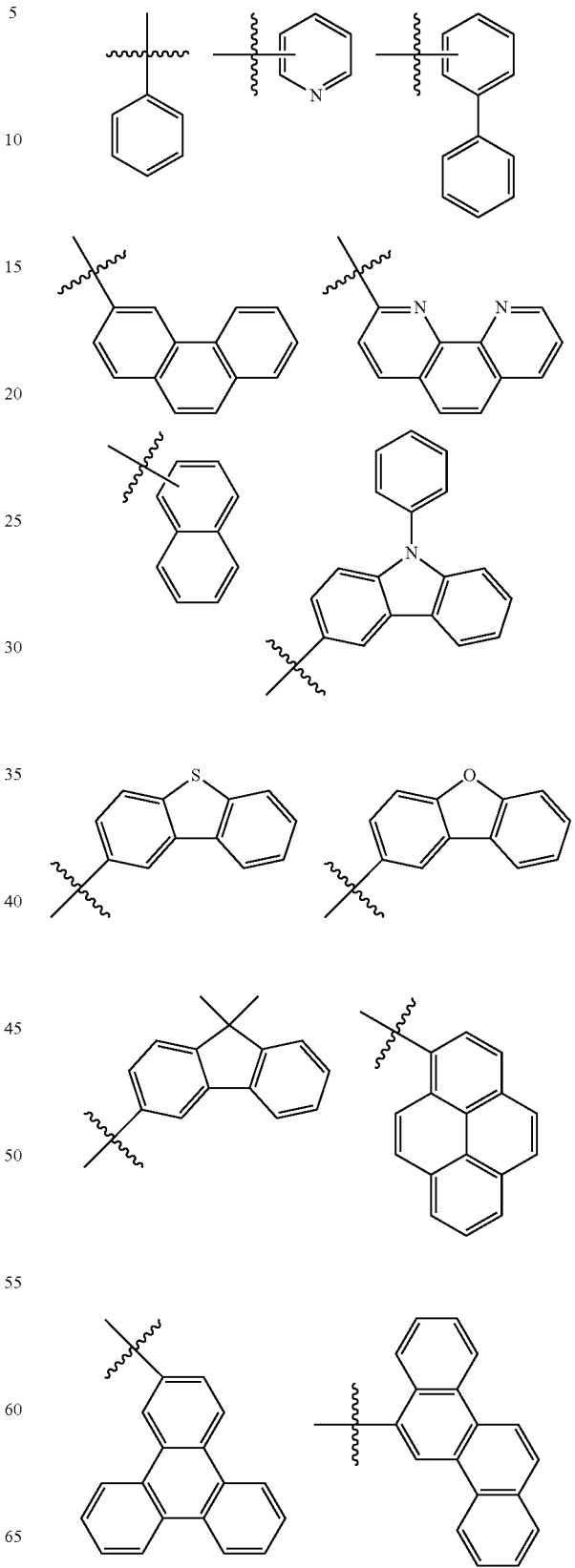

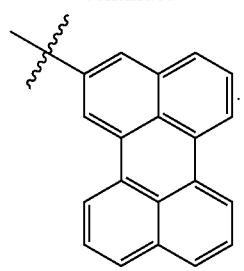
4. The indenotriphenylene derivative of claim 1, wherein the indenotriphenylene derivative is one of the following compounds:
A1
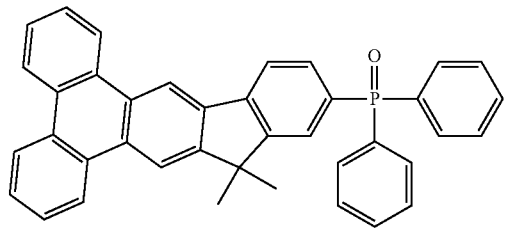
A2
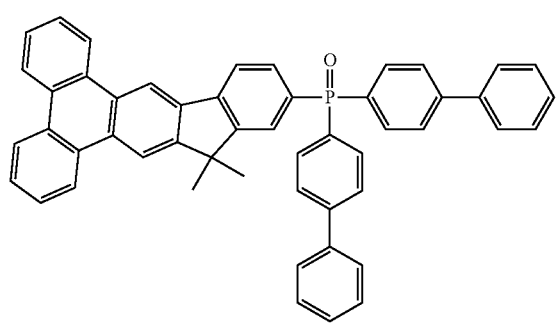
A3
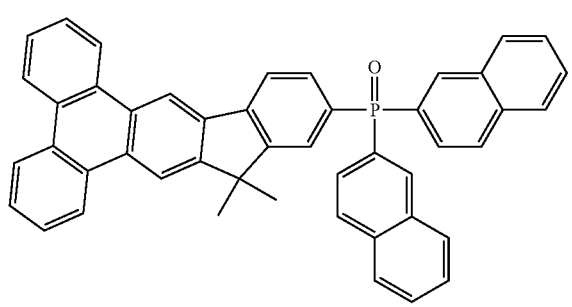
A4
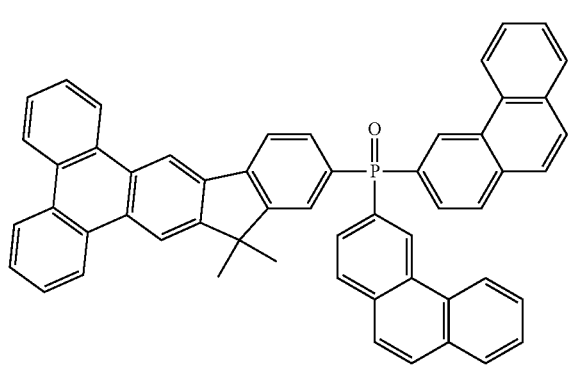
A5
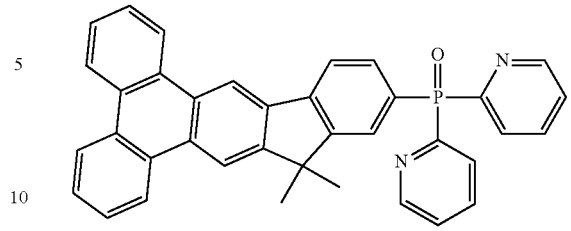
A6
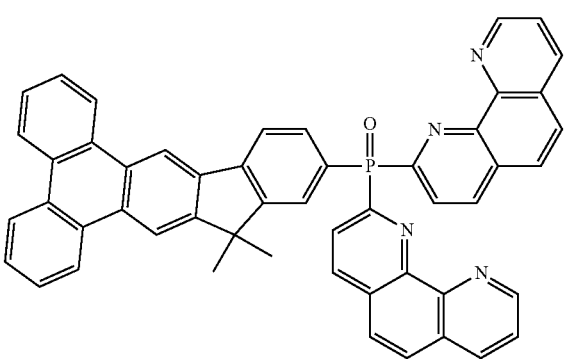
A7
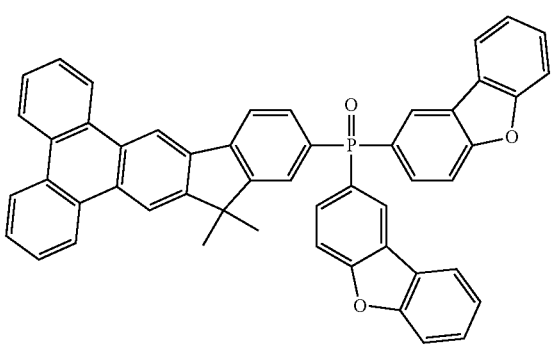
A8
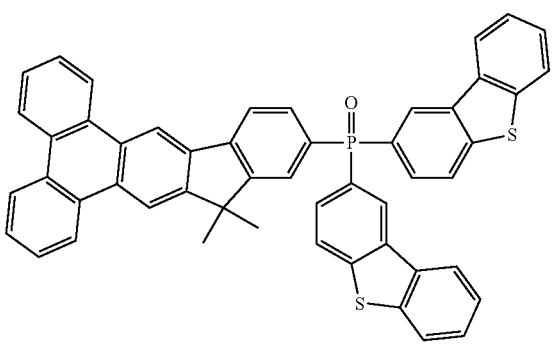

-continued
A9
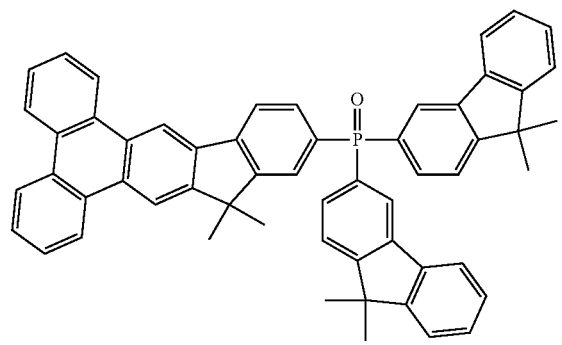
A10
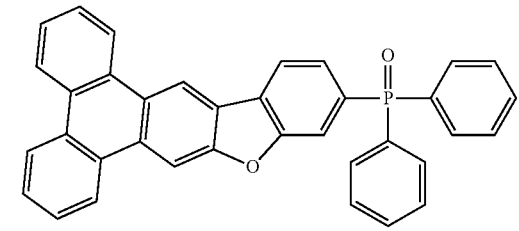
A11
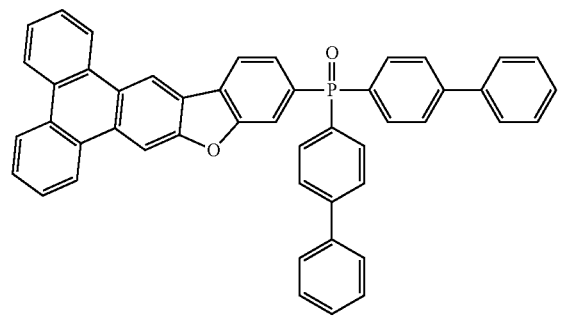
A12
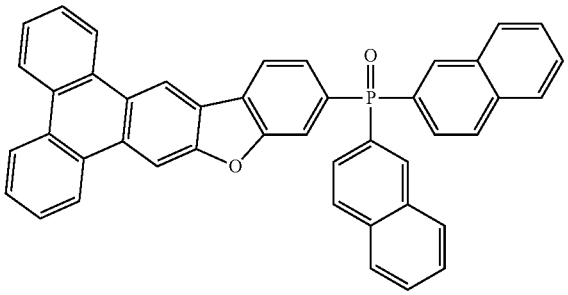
A13
-continued
A14
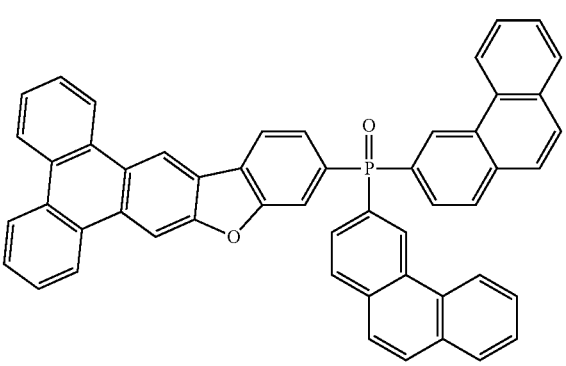
A15
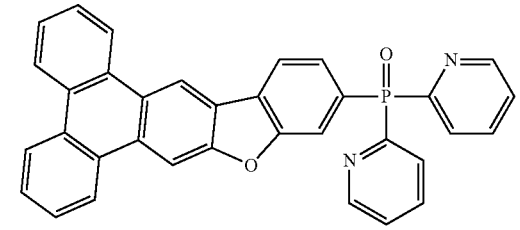
A16
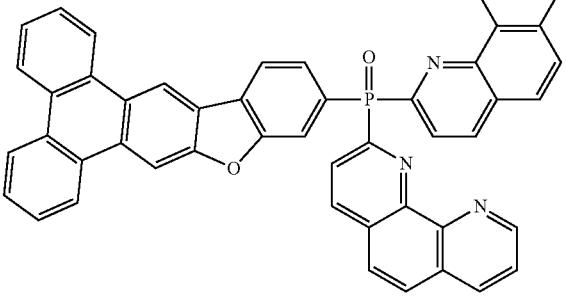
A17
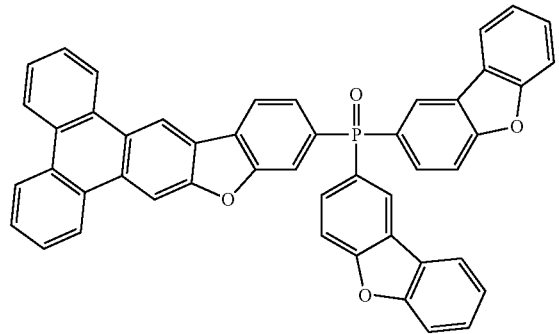

-continued
A18
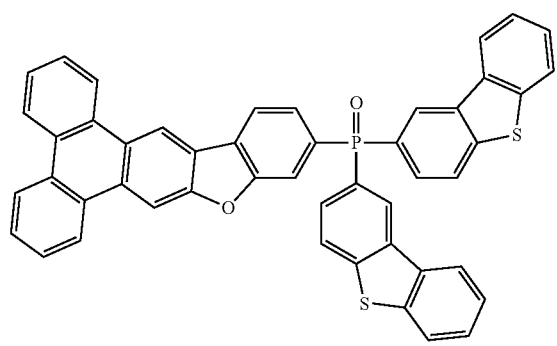
A19
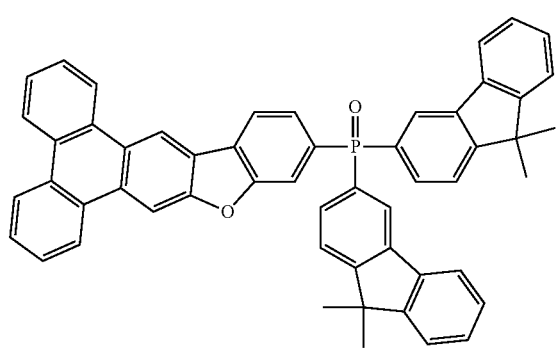
A20
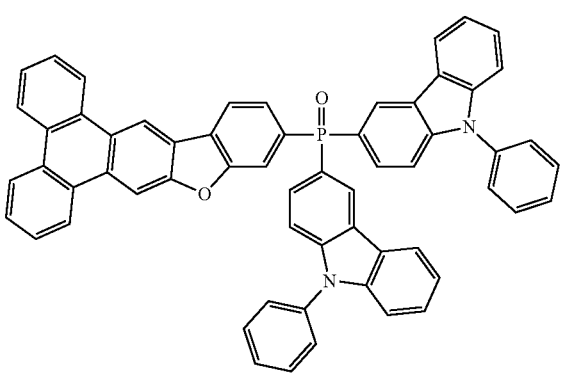
A21
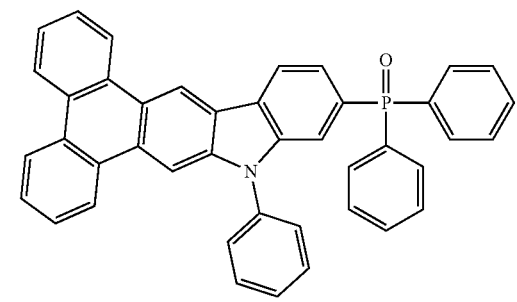
-continued
A22
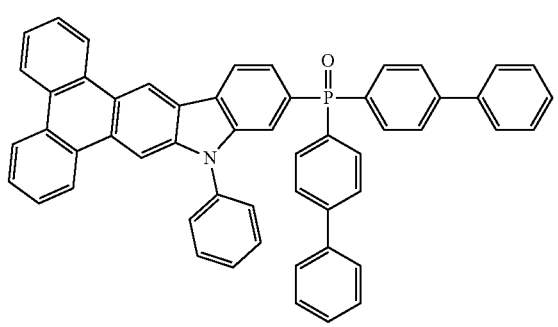
A23
A24
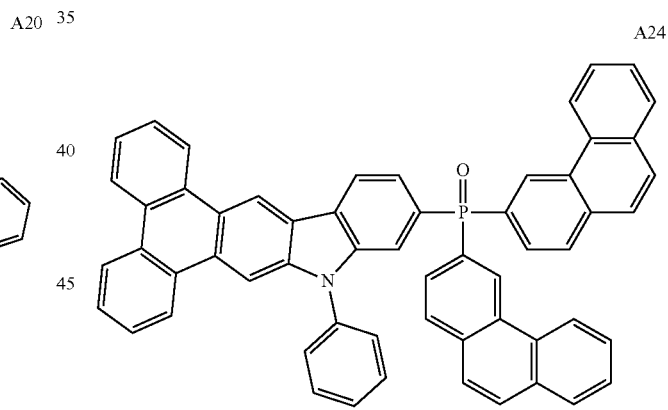
A25
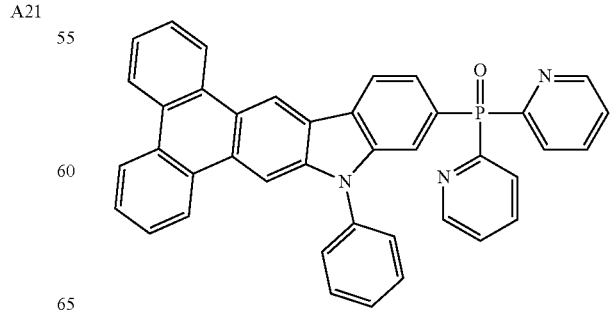

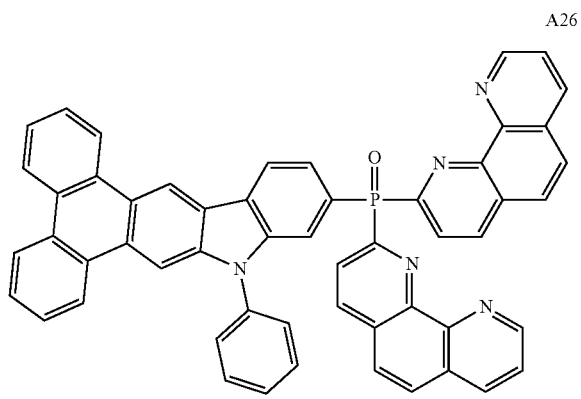
A26
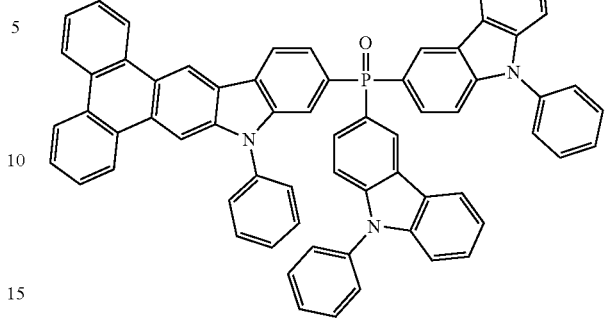
A30
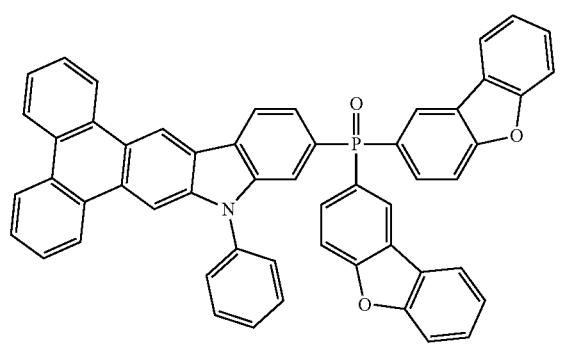
A27
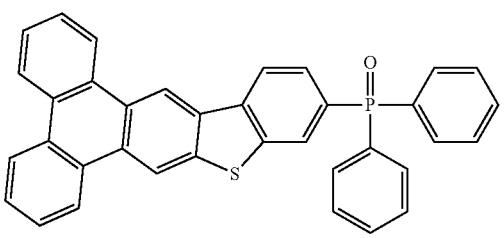
A31
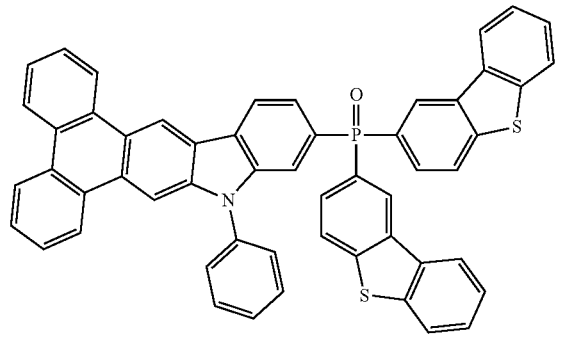
A28
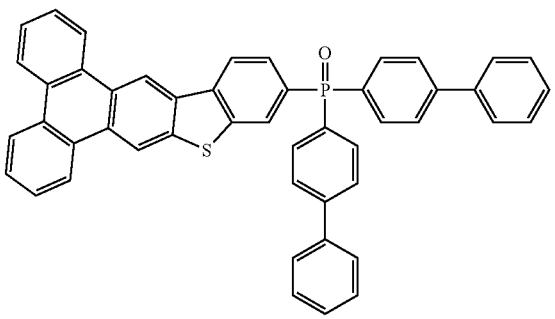
A32
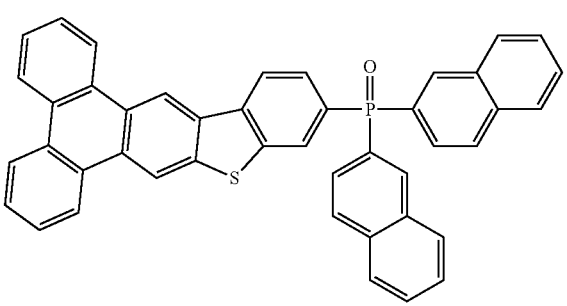
A33
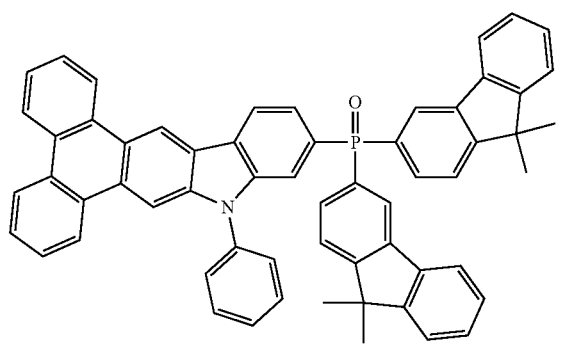
A29
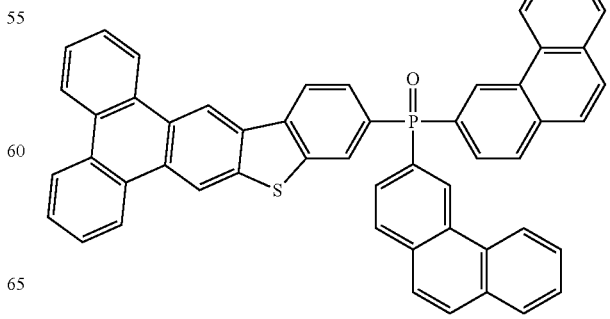
A34

A35 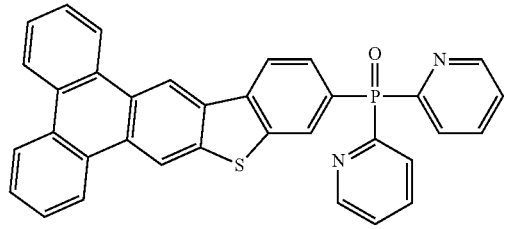
A36 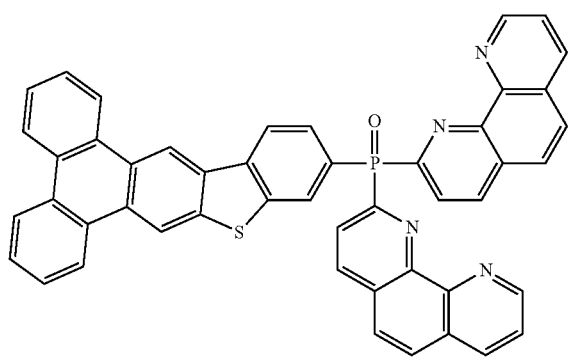
A39 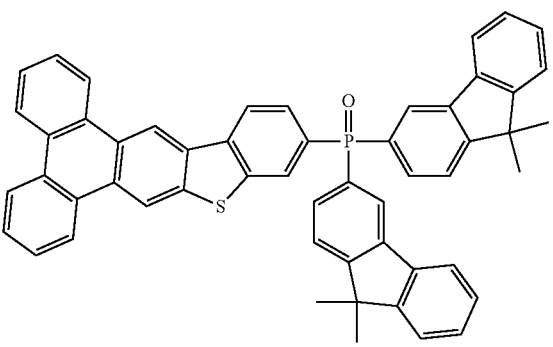
A37 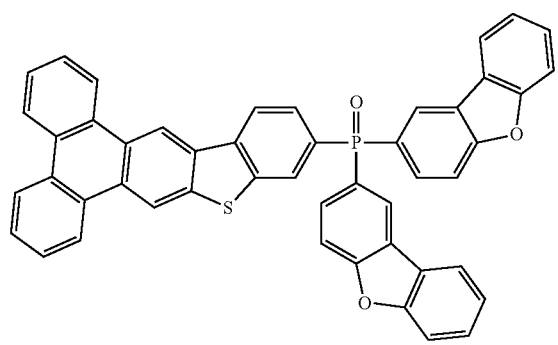
A38 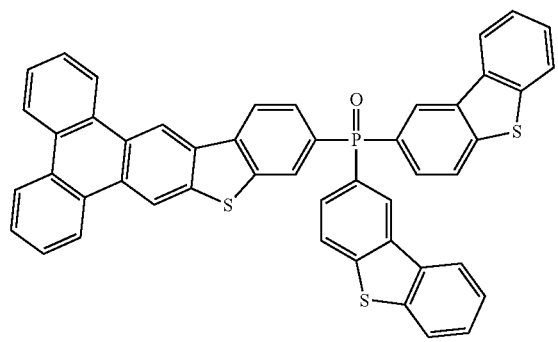
A40
A41
A42 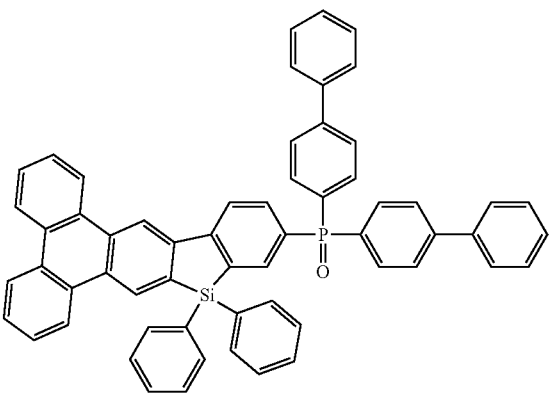

-continued
A43
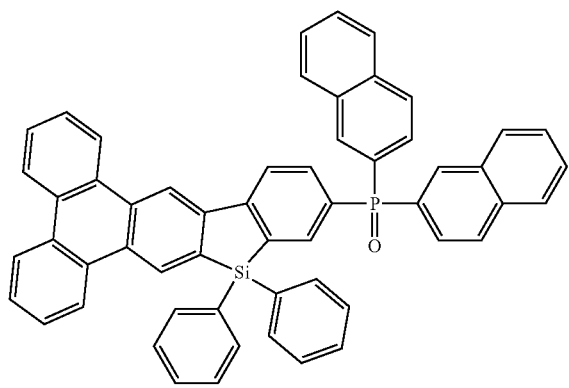
A44
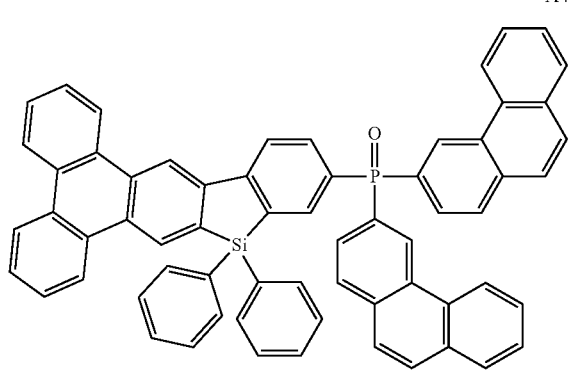
A45
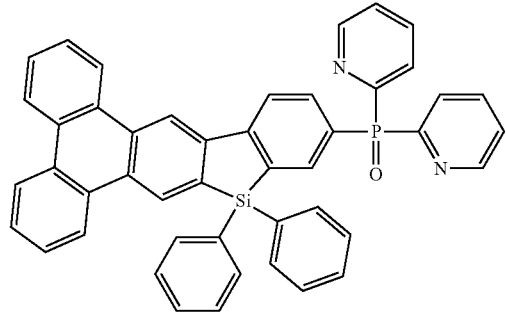
A46
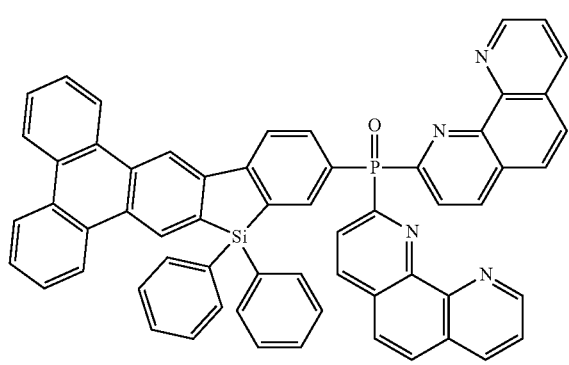
-continued
A47
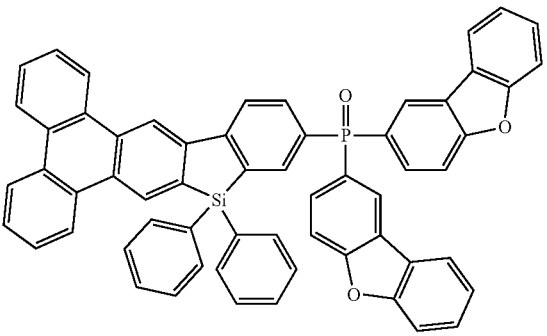
A48
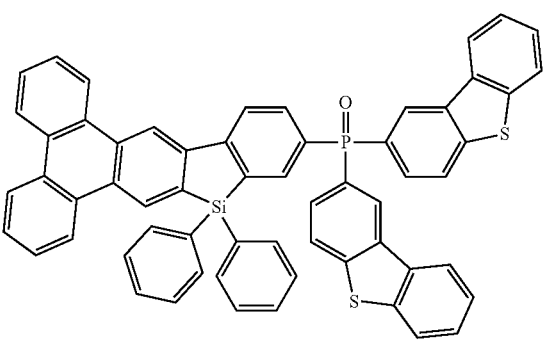
A49
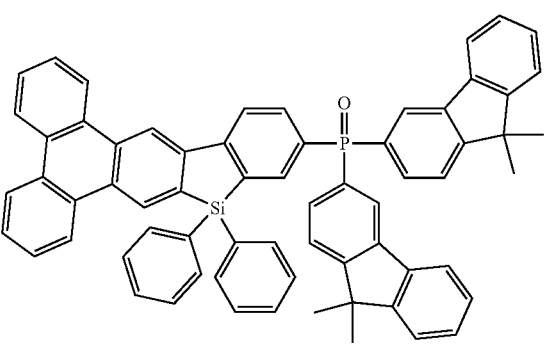
A50
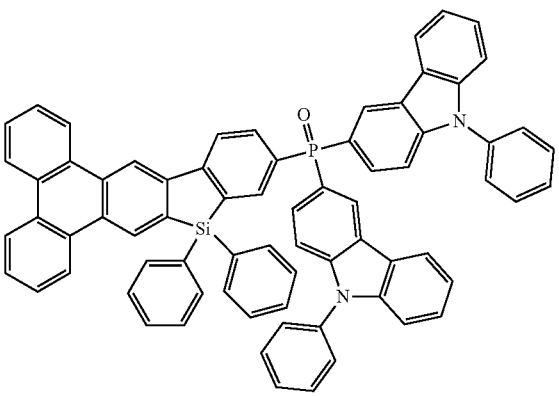

-continued
A51
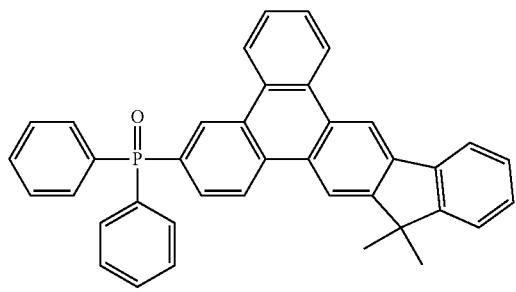
A52
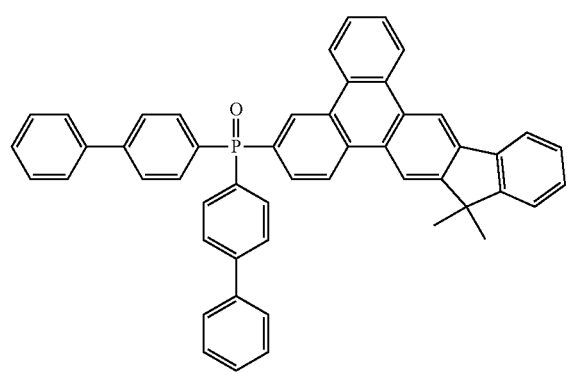
A53
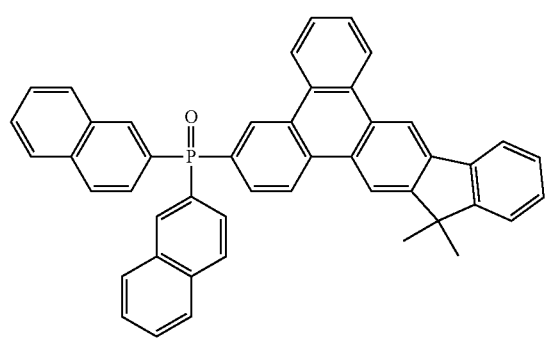
A54
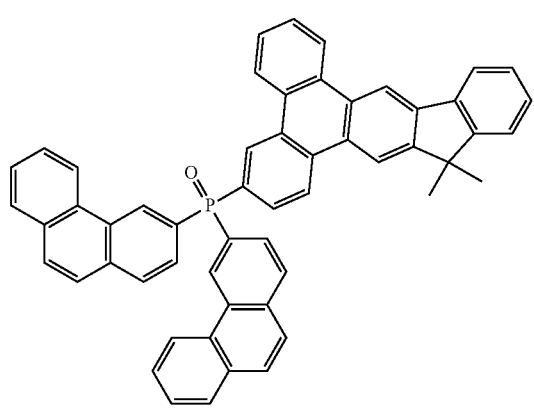
-continued
A55
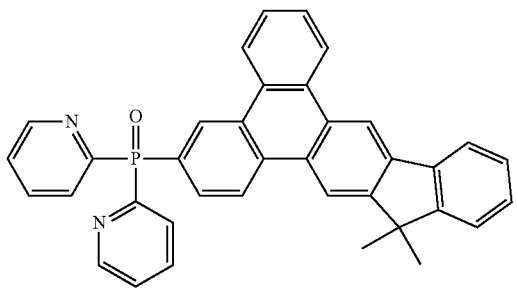
A56
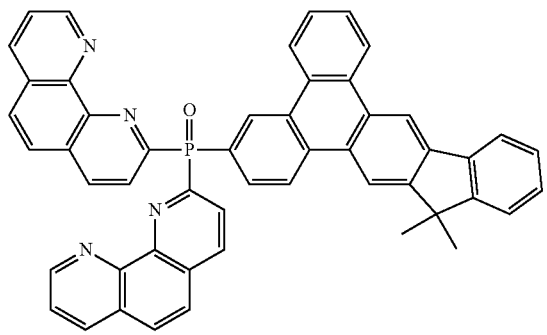
A57
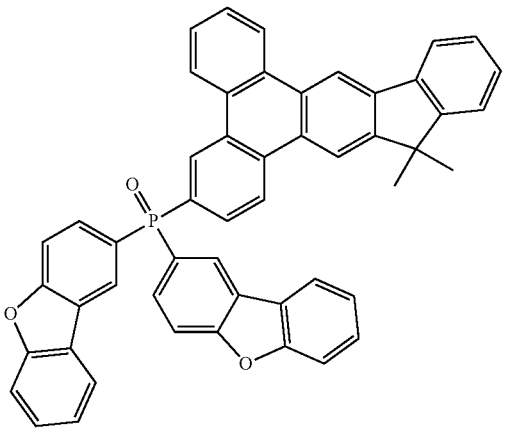
A58
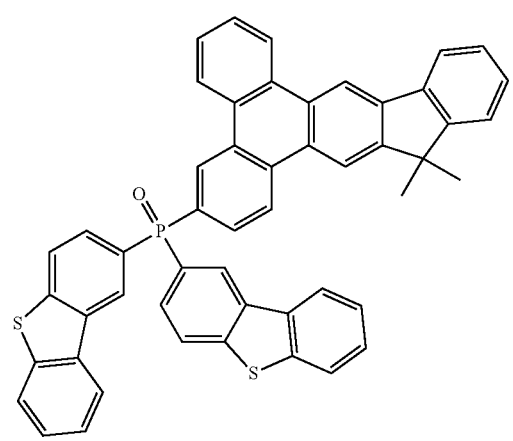

A59
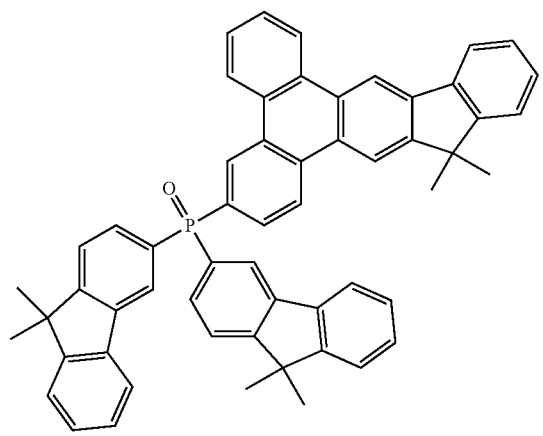
A60
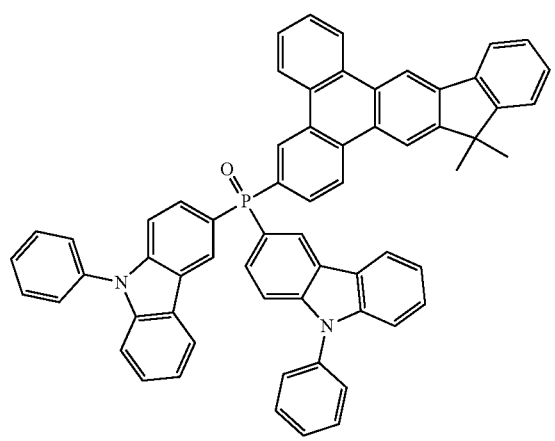
A61
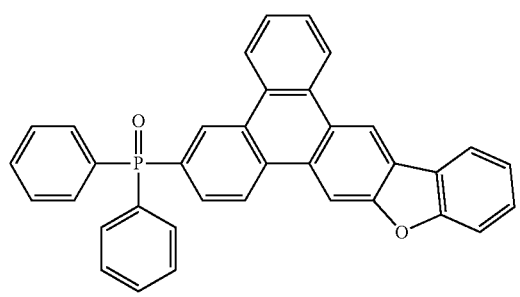
A62
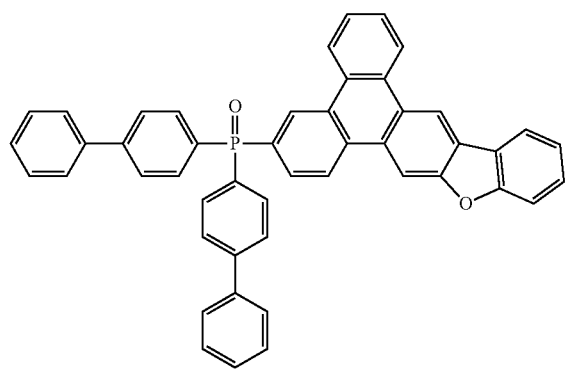
A63
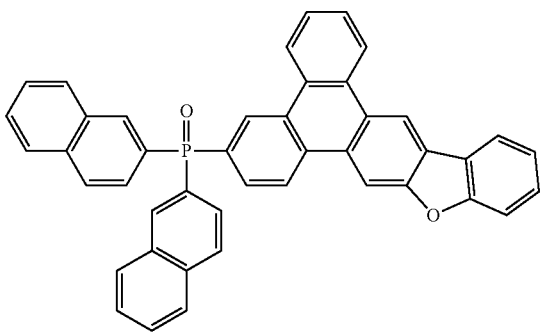
A64
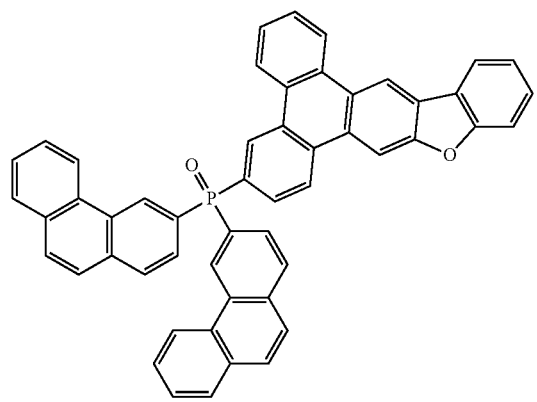
A65
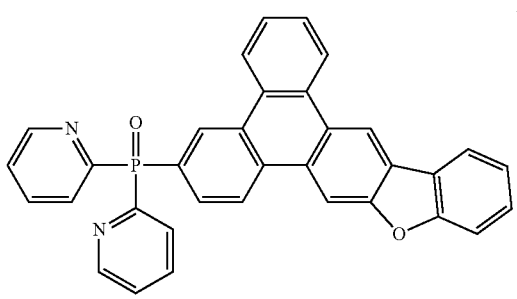
A66
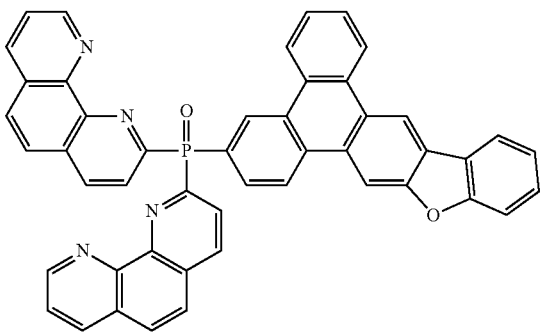

A67
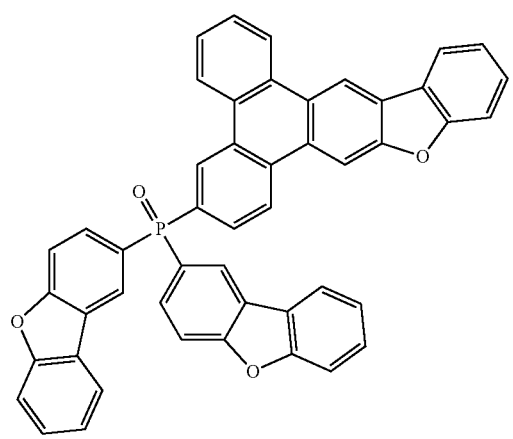
A68
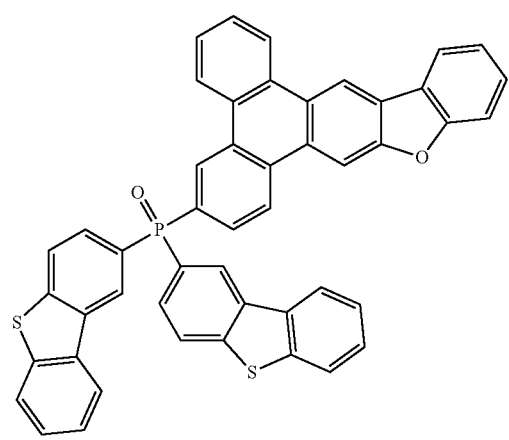
A69
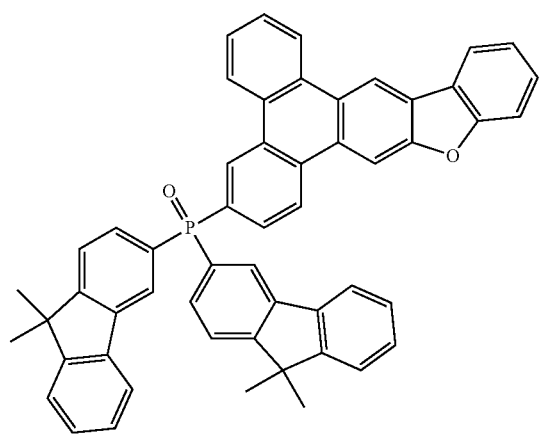
A70
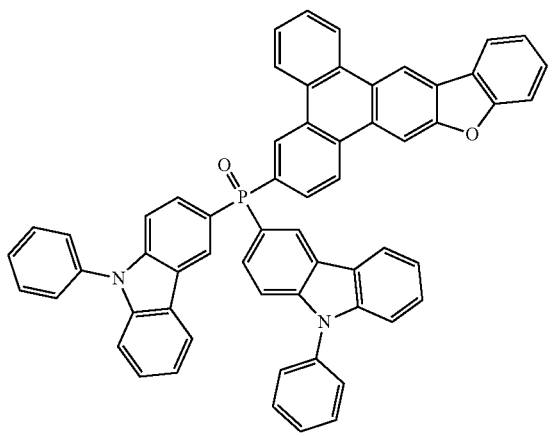
A71
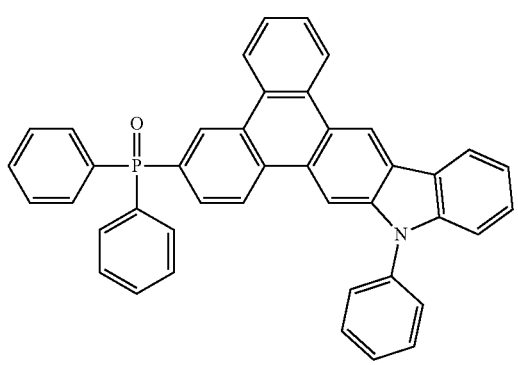
A72
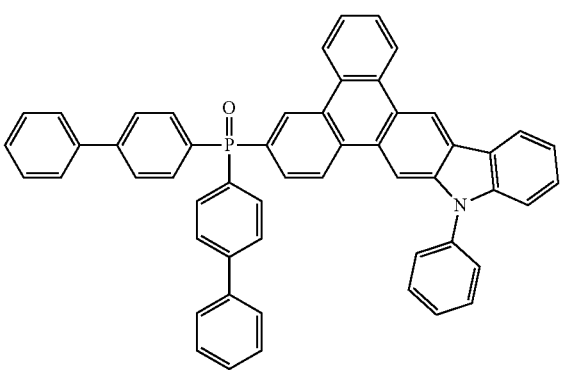
A73
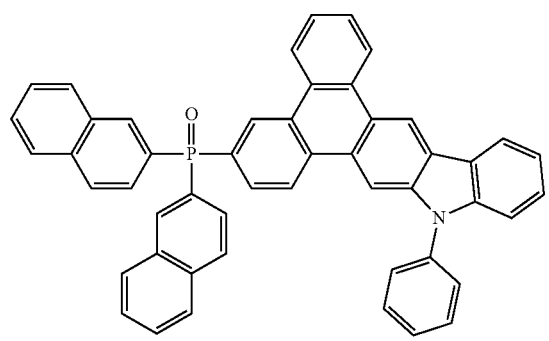

A74 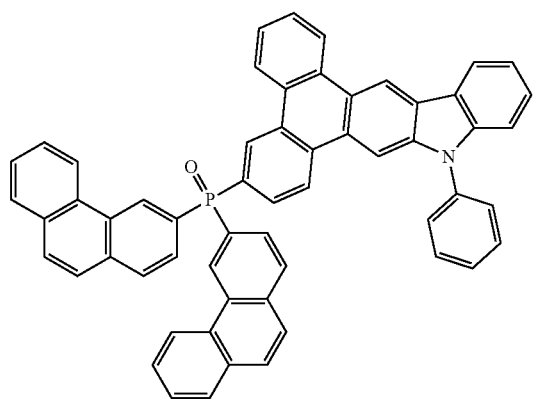
A75 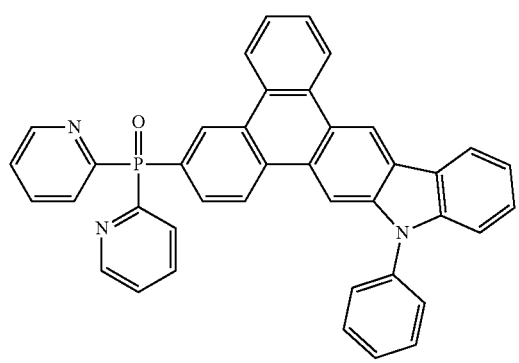
A76 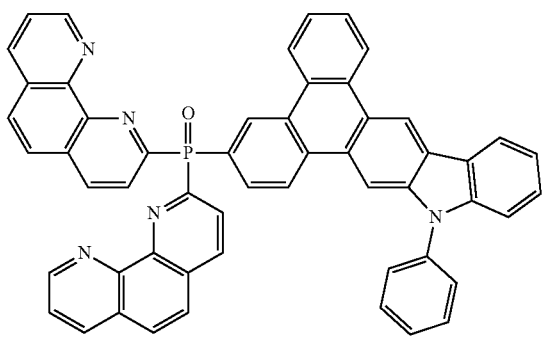
A77 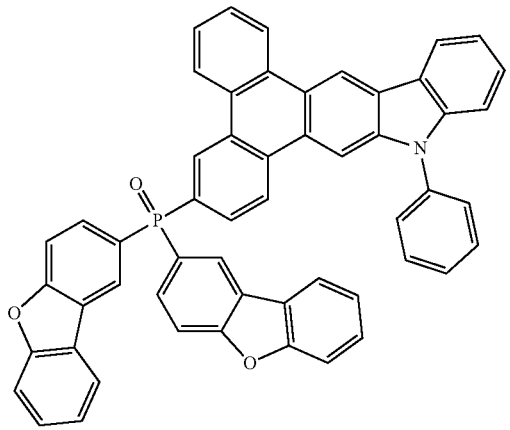
A78 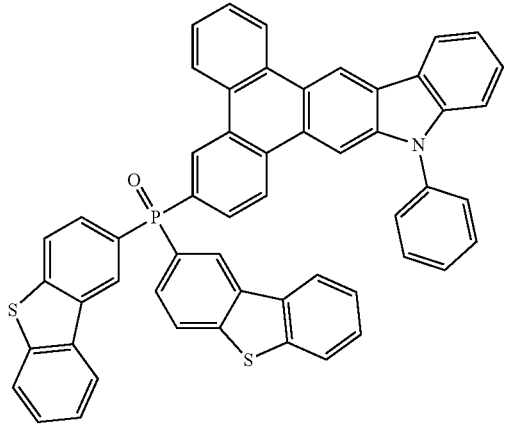
A79 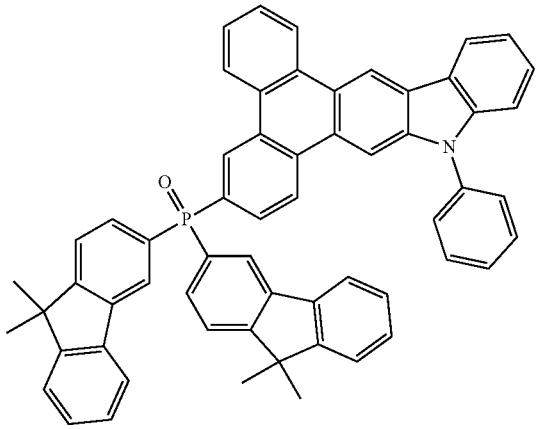
A80 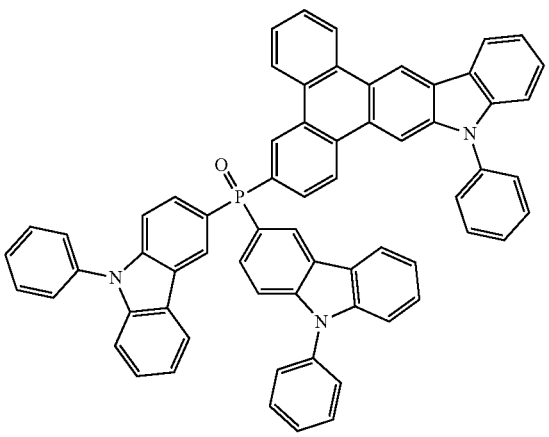
A81 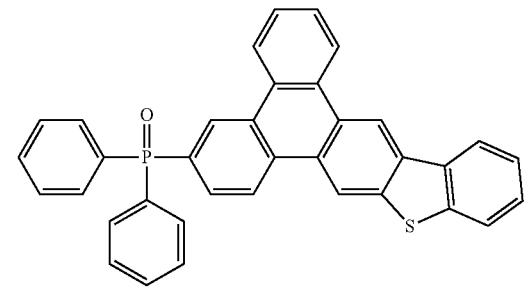

A82
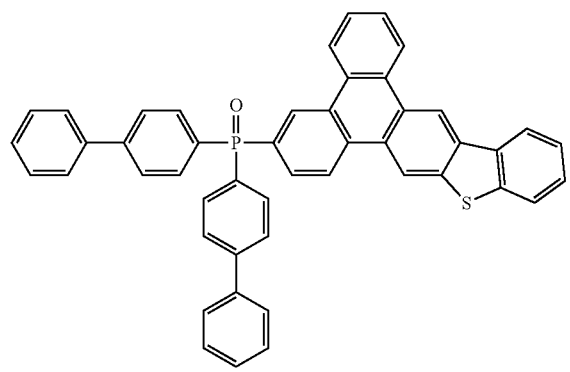
A83
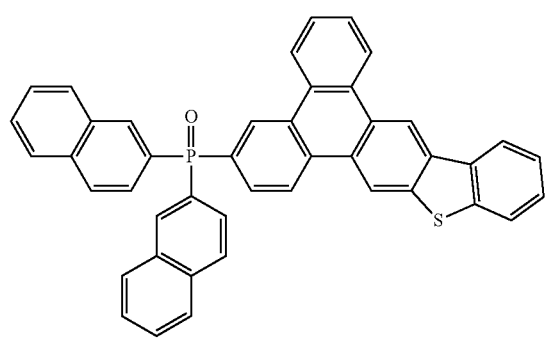
A84
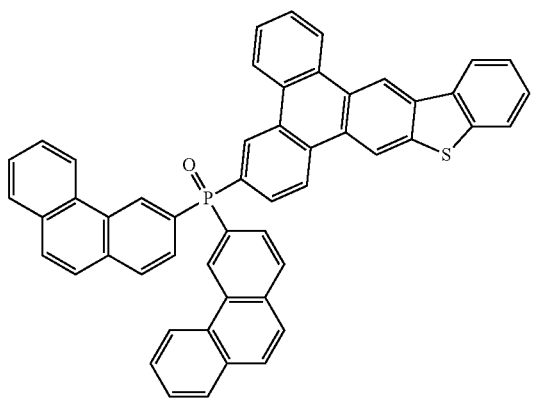
A85
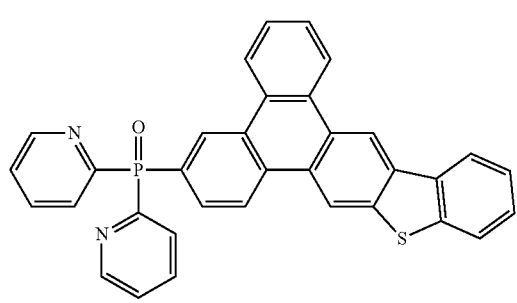
A86
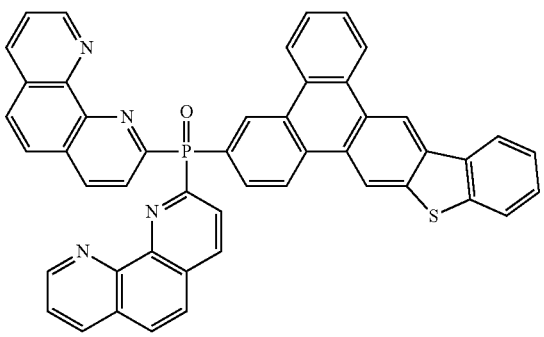
A87
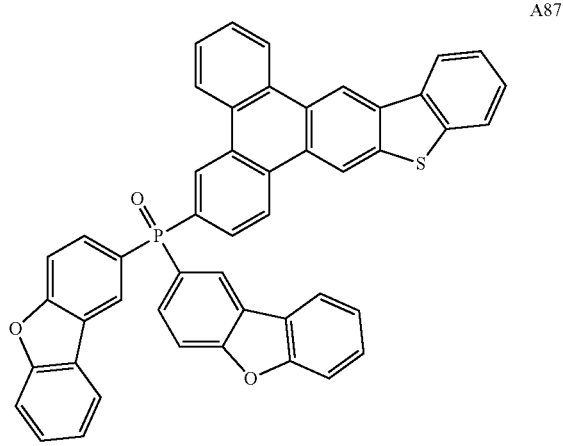
A88
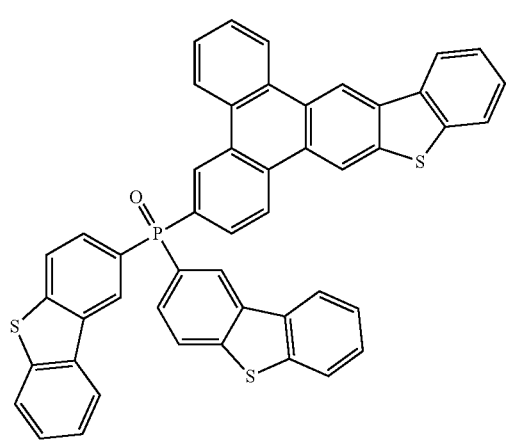

-continued
A89
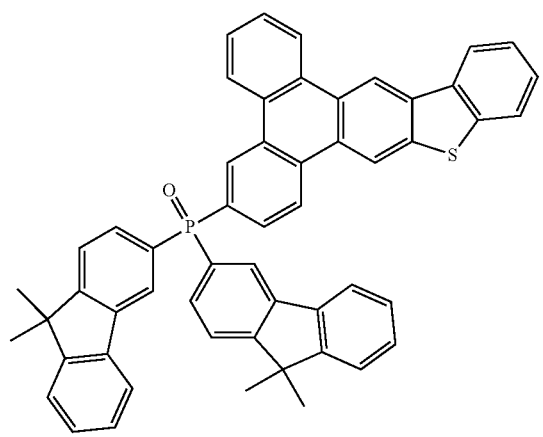
A90
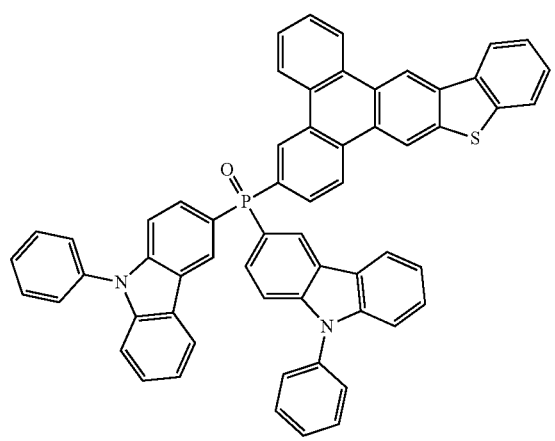
A91
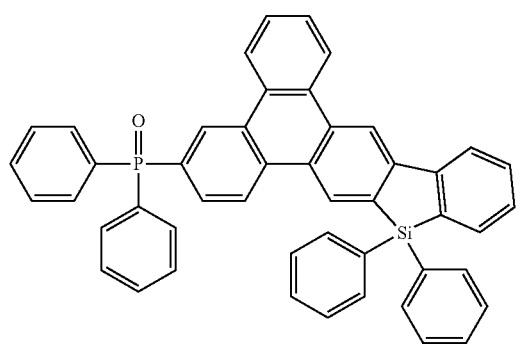
A92
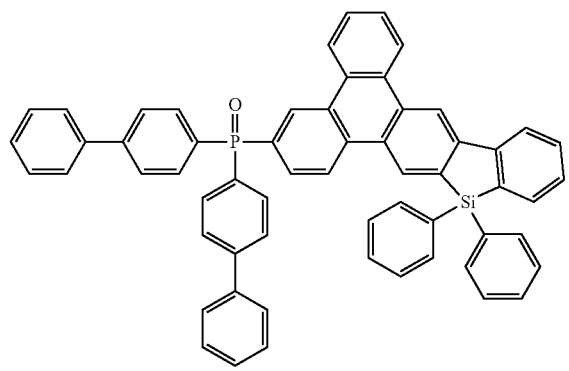
-continued
A93
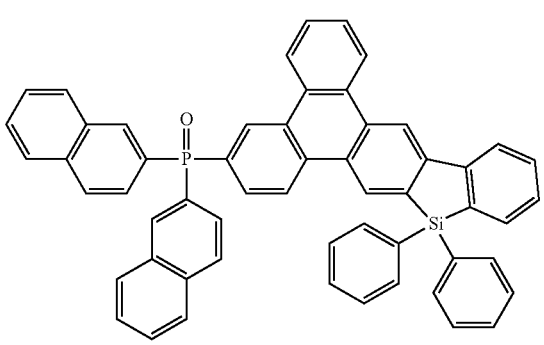
A94
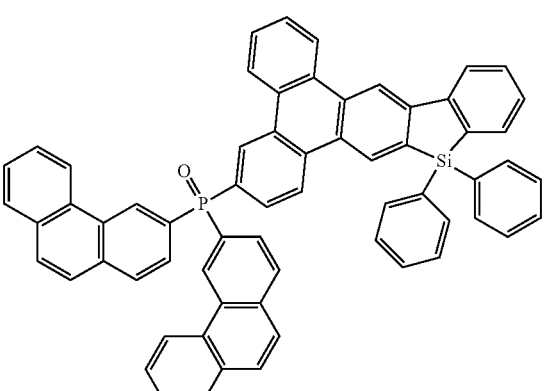
A95
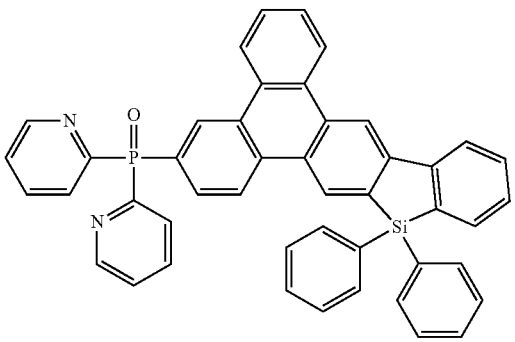
A96
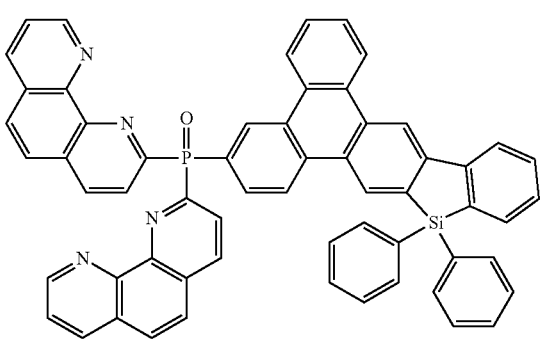

-continued
A97
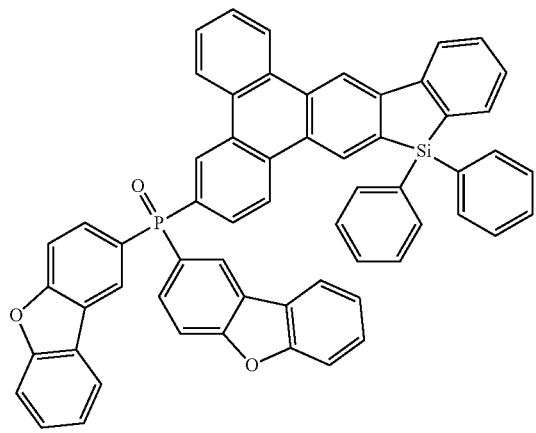
A98
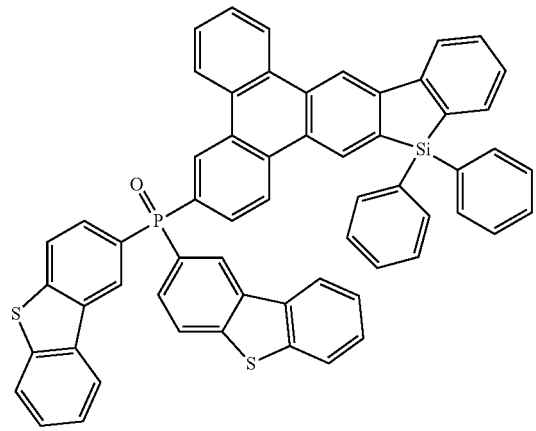
A99
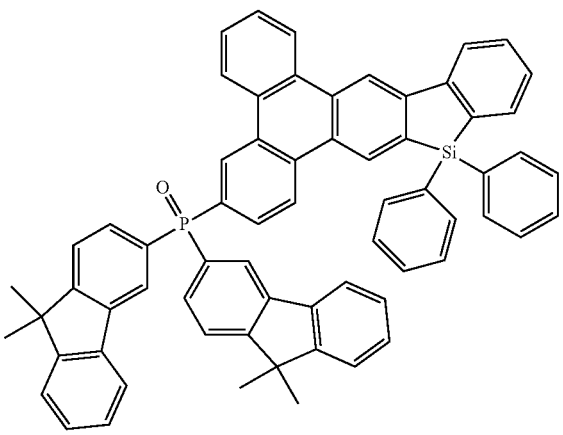
-continued
A100
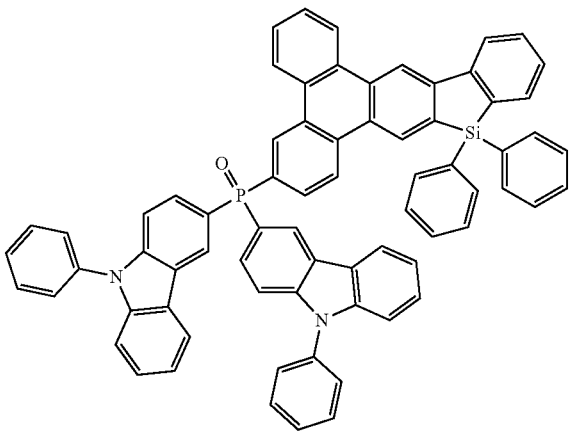
A101
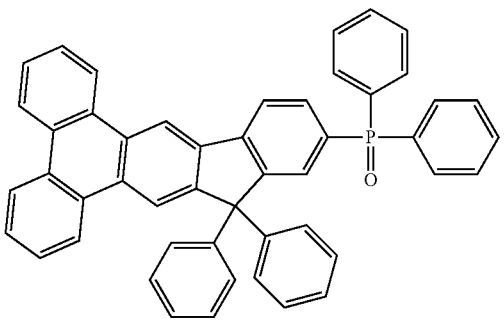
A102
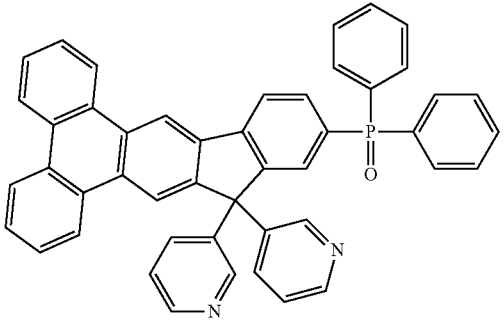
A103
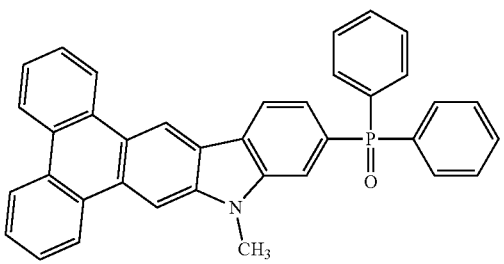

A104
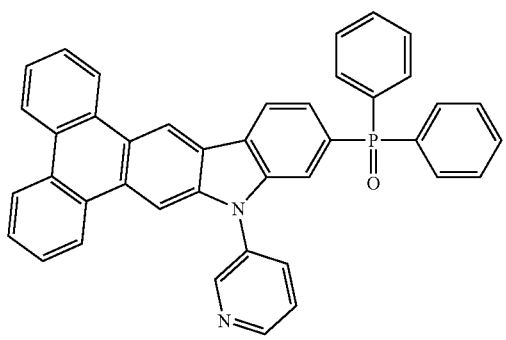
A109
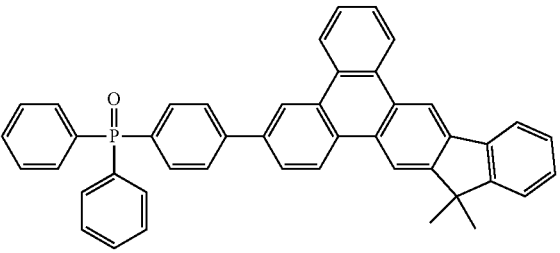
A105
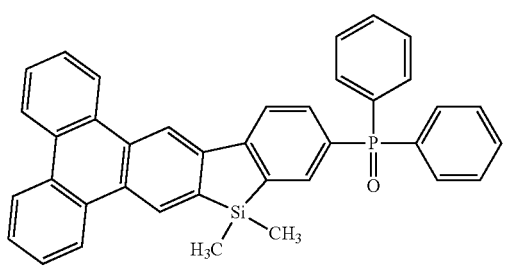
A110
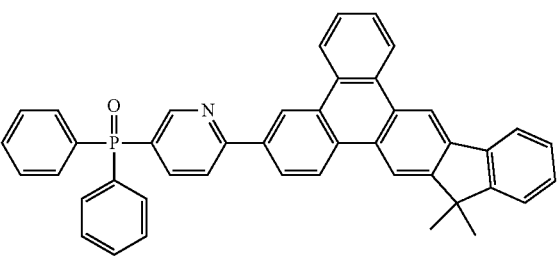
A106
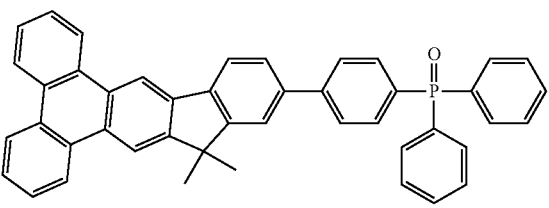
A111
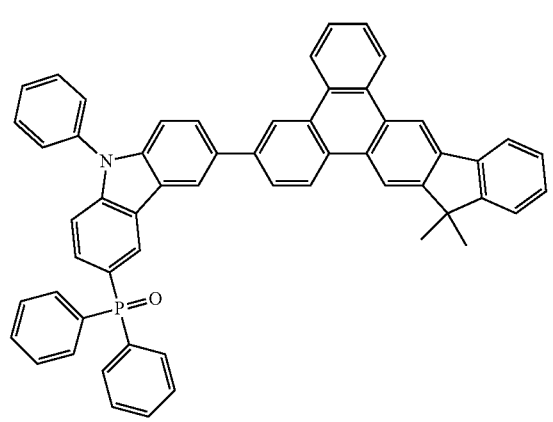
A107
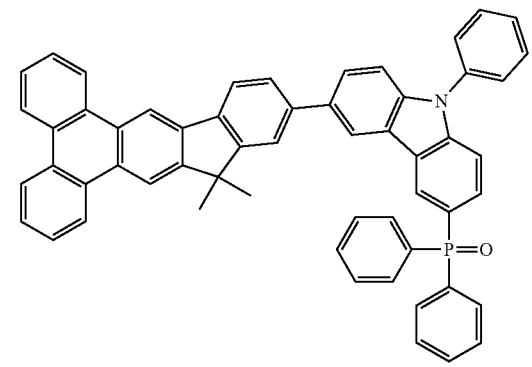
A112
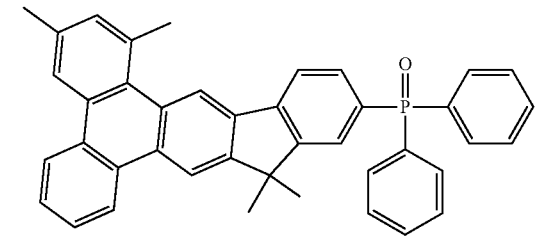
A108
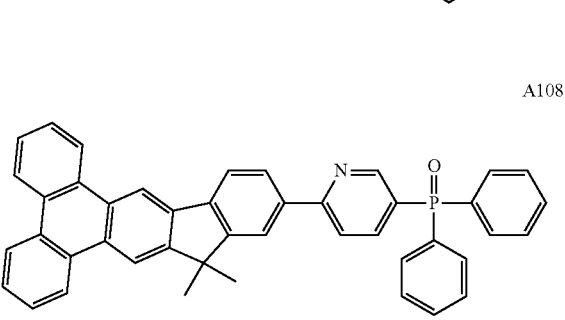
A113
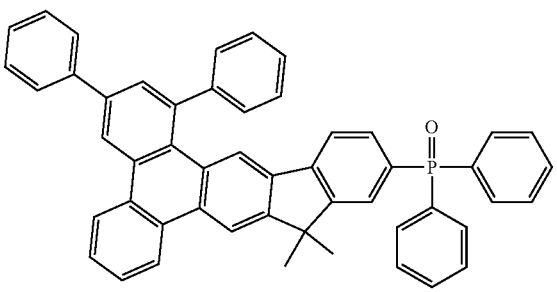

A114
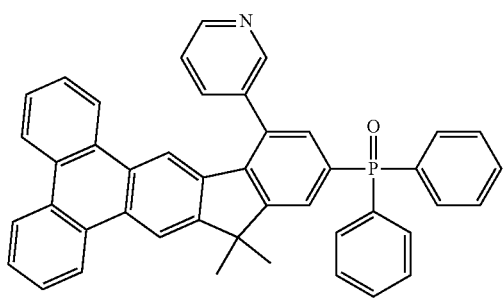
A115
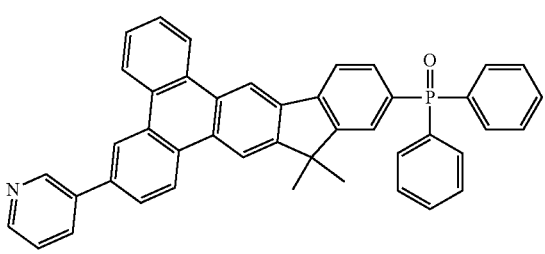
A116
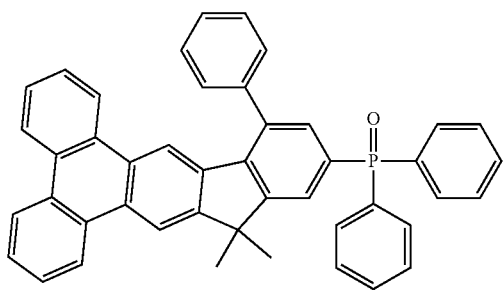
A117
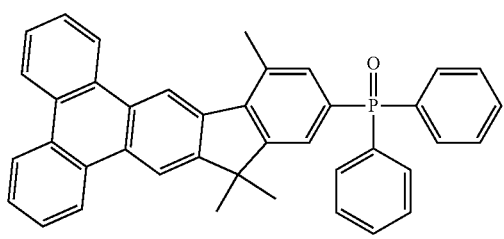
A118
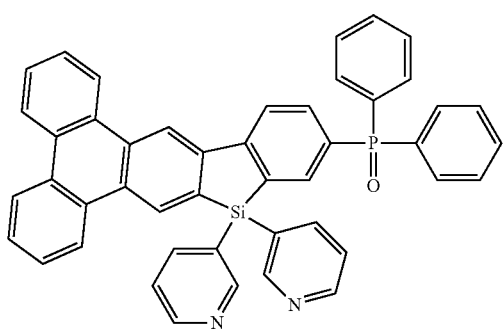
A119
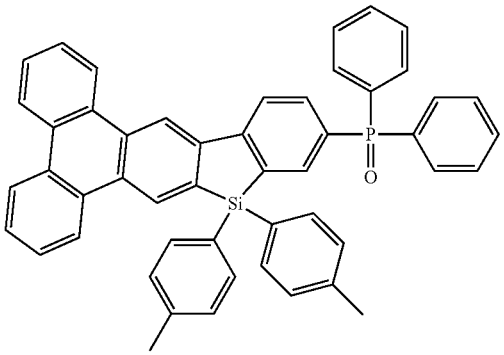
A120
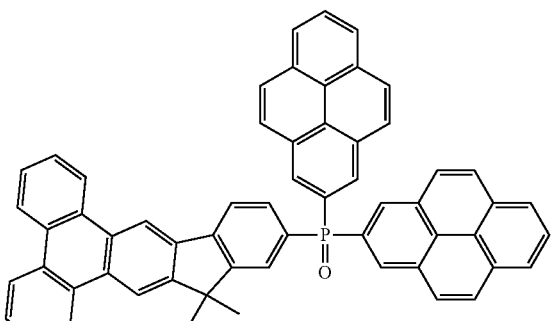
A121
A122
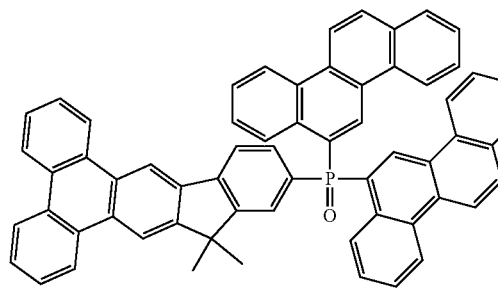

A123
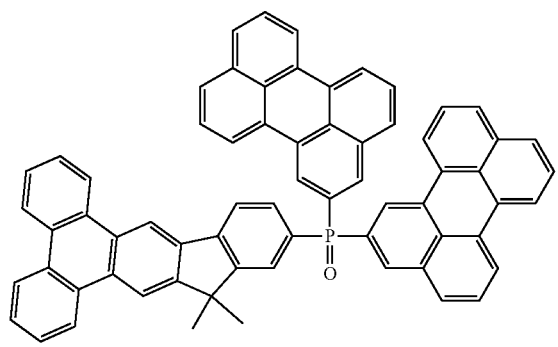
A128
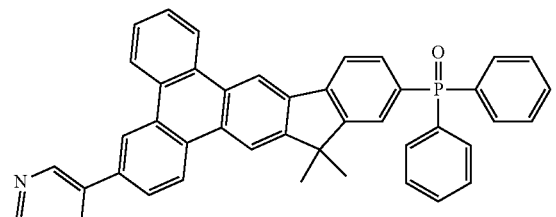
A124
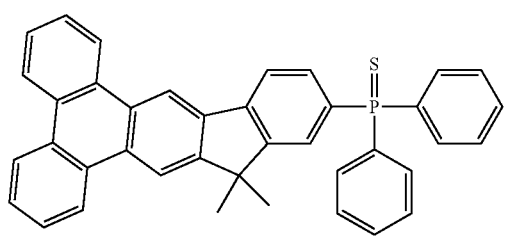
A129
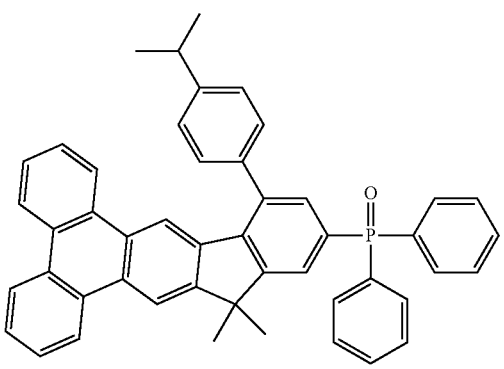
A125
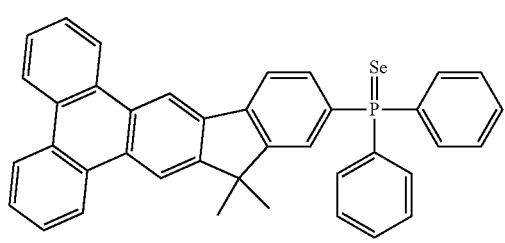
A126
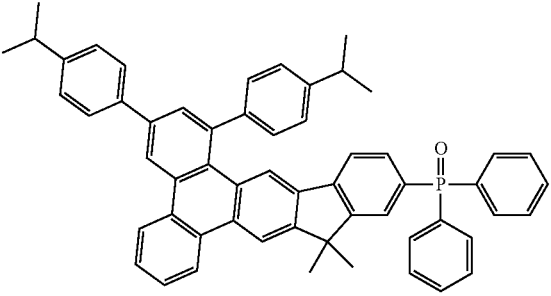
A130
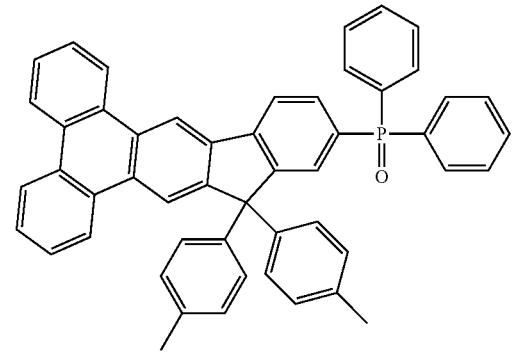
A127
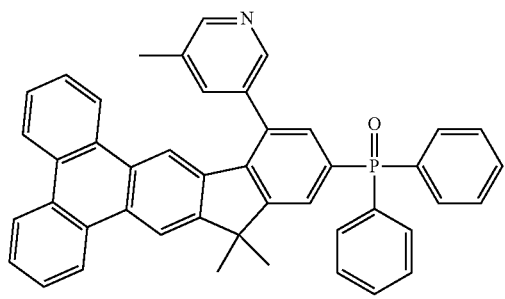
A131
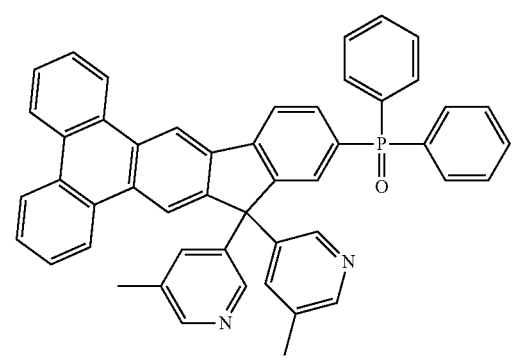

-continued
A132
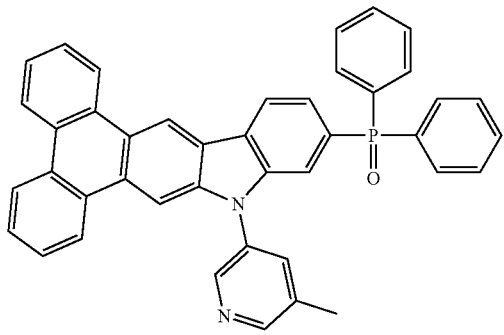
A133
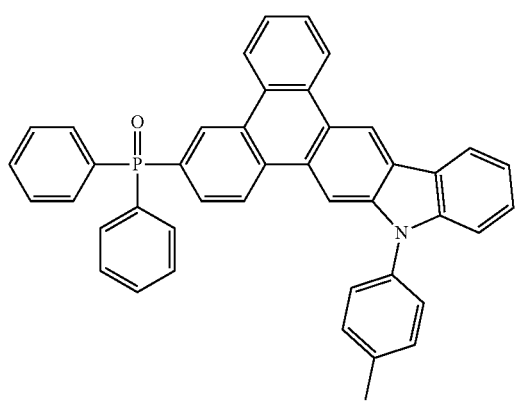
A134
A135
A136
-continued
A137
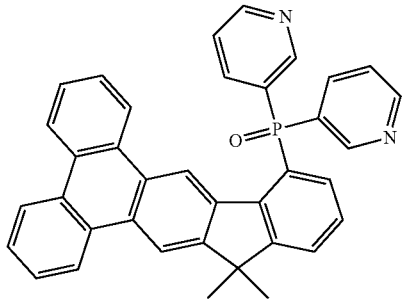
A138
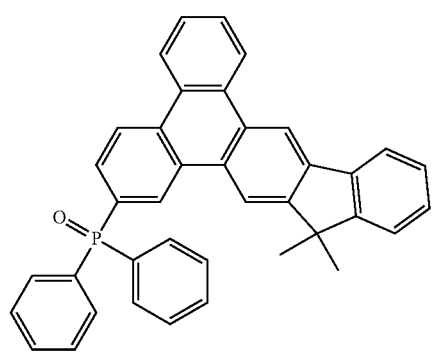
A139
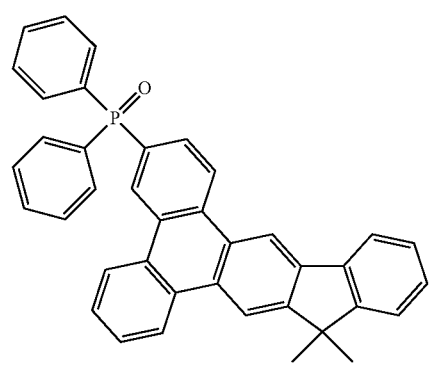
A140
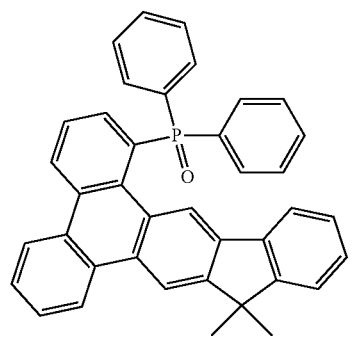

A141

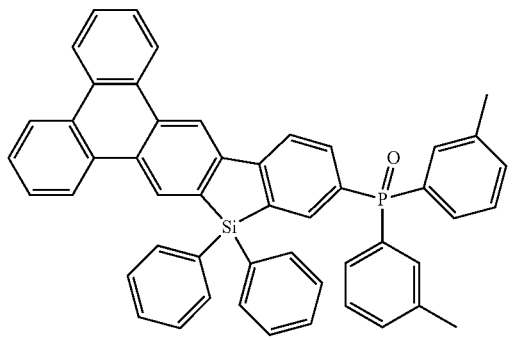

A143

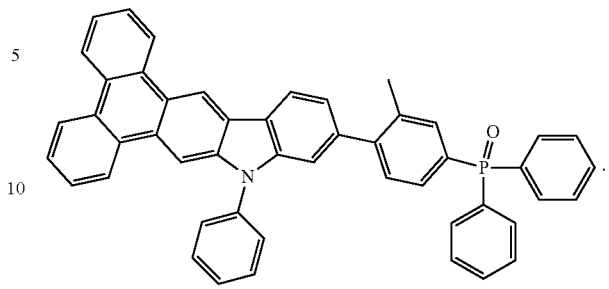

A142

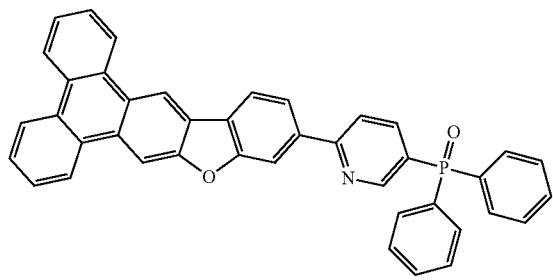

5. An organic electroluminescence device, comprising a pair of electrodes composed of a cathode and an anode, and a light emitting layer and one or more organic thin film layers between the pair of electrodes, wherein at least one of the light emitting layer and the organic thin film layer comprises the indenotriphenylene derivative of claim 1.

6. The organic electroluminescence device of claim 5, wherein the light emitting layer comprising the indenotriphenylene derivative of formula (A) is a phosphorescent host material.

7. The organic electroluminescence device of claim 6, wherein the light emitting layer further comprises a phosphorescent dopant material.

8. The organic electroluminescence device of claim 7, wherein the phosphorescent dopant material is an iridium (Ir) complex.

9. The organic electroluminescence device of claim 5, wherein the organic thin film layer comprising the indenotriphenylene derivative of formula (A) is an electron transporting layer.

10. The organic electroluminescence device of claim 5, wherein the organic thin film layer comprising the indenotriphenylene derivative of formula (A) is a hole blocking layer.

11. The organic electroluminescence device of claim 5, wherein the organic electroluminescence device is a lighting panel.

12. The organic electroluminescence device of claim 5, wherein the organic electroluminescence device is a backlight panel.

* * * * *